United States Patent [19]

Haviv et al.

[11] Patent Number: 5,502,035
[45] Date of Patent: Mar. 26, 1996

[54] N-TERMINUS MODIFIED ANALOGS OF LHRH

[75] Inventors: Fortuna Haviv, Deerfield, Ill.; Timothy D. Fitzpatrick, Boulder, Colo.; Rolf E. Swenson, Grayslake, Ill.; Charles J. Nichols, Greendale, Wis.; Nicholas A. Mort, Waukegan, Ill.

[73] Assignee: Tap Holdings Inc., Abbott Park, Ill.

[21] Appl. No.: 279,677

[22] Filed: Jul. 27, 1994

Related U.S. Application Data

[63] Continuation-in-part of Ser. No. 103,474, Aug. 6, 1993, abandoned.

[51] Int. Cl.$^6$ ..................................................... C07K 14/59
[52] U.S. Cl. ........................... 514/15; 530/313; 530/327; 530/328
[58] Field of Search ..................................... 530/327, 328, 530/313; 514/15

[56] References Cited

U.S. PATENT DOCUMENTS

| | | |
|---|---|---|
| 4,317,815 | 3/1982 | Coy et al. . |
| 4,409,208 | 10/1983 | Rivier et al. . |
| 4,444,759 | 4/1984 | Rivier et al. . |
| 4,569,927 | 2/1986 | Rivier et al. . |
| 4,619,914 | 10/1986 | Vale, Jr. et al. ............................ 514/15 |
| 4,628,044 | 12/1986 | Loozen ........................................ 514/15 |
| 4,652,550 | 3/1987 | Rivier et al. . |
| 4,661,472 | 4/1987 | Rivier et al. . |
| 4,677,193 | 6/1987 | Rivier et al. . |
| 4,800,191 | 1/1989 | Schally et al. ............................. 514/15 |
| 5,110,904 | 5/1992 | Haviv et al. ............................... 530/313 |
| 5,171,835 | 12/1992 | Janaky et al. ............................. 530/313 |
| 5,198,533 | 3/1993 | Schally et al. ............................ 530/313 |

FOREIGN PATENT DOCUMENTS

| | | |
|---|---|---|
| 0182262 | 5/1986 | European Pat. Off. . |
| 0413209 | 2/1991 | European Pat. Off. . |
| 9106543 | 5/1991 | WIPO . |
| 9213883 | 8/1992 | WIPO . |
| 9217025 | 10/1992 | WIPO . |
| 9222322 | 12/1992 | WIPO . |

*Primary Examiner*—Howard E. Schain
*Attorney, Agent, or Firm*—Jerry F. Janssen

[57] ABSTRACT

Decapaptide and undecapaptides substituted on the N-terminal nitrogen atom by acyl groups which include furo-2-yl, isonicotinyl, nicotinyl, 2-, 3-, and 4-quinolinecarbonyl, shikimyl, dihydroshikimyl, and tetrahydrofur-2-oyl are potent antagonists of LHRH and are useful for suppressing the levels of sex hormones in mammals.

8 Claims, No Drawings

N-TERMINUS MODIFIED ANALOGS OF LHRH

CROSS-REFERENCE TO RELATED APPLICATIONS

This application is a continuation-in-part of application Ser. No. 08/103,474 filed Aug. 6, 1993, abandoned.

TECHNICAL FIELD

The present invention relates to organic compounds having biological activity, to compositions containing the compounds, and to medical methods of treatment. More particularly, the present invention concerns certain N-terminus modified deca- and undecapeptides having LHRH antagonist activity, pharmaceutical compositions containing the peptides, and a method of inhibiting LHRH activity in a mammal in need of such treatment.

BACKGROUND OF THE INVENTION

The gonadotropins: follicle stimulating hormone (FSH), luteinizing hormone (LH), and chorionic gonadotropin (CG), are required for ovulation, spermatogenesis, and the biosynthesis of sex steroids. A single hypothalamic hormone, gonadotropin-releasing hormone (GnRH, also known as luteinizing hormone-releasing hormone, LHRH) is responsible for regulating the secretion of both FSH and LH in mammals.

The structure of LHRH was determined by A. V. Schally, et al., *Science*, 173: 1036–1037 (1971). Early attempts to prepare peptides having LHRH-like activity centered on the synthesis of compounds which were LHRH agonists. However, in 1976 it was found that while individual doses of LHRH stimulated the release of gonadotropin, the continuous administration of small doses of LHRH or chronic administration of LHRH agonists had the opposite effect. This finding stimulated research for the discovery of both agonist and antagonist analogs of LHRH as agents useful for regulating sex steroids in mammals. A considerable number of patents and articles in the open literature disclose analogs of LHRH which either act as agonists of LHRH (i.e. act to stimulate the release of LH and FSH) or as antagonists of LHRH (i.e. act to inhibit the release of LH and FSH). For the most part, these compounds contain nine or ten aminoacyl residues, substituting naturally-occurring or non-naturally-occurring amino acid residues at one or more positions in the natural sequence of LHRH. In some cases, active antagonists of LHRH have been reported which contain fewer than ten amino acid residues.

The literature has reported that LHRH antagonists are useful for the treatment of a variety of conditions in which the suppression of sex steroids plays a key role including contraception, delay of puberty, treatment of benign prostatic hyperplasia, palliative treatment or remission of hormonal-dependent tumors of the breast and ovaries, palliative treatment or remission of hormonal-dependent tumors of the prostate, the treatment of cryptoorchidism, hirsutim in women, gastric motility disorders, dysmenorrhea, and endometriosis.

SUMMARY OF THE INVENTION

The present invention provides, in its principle embodiment, a class of deca- and undecapeptide antagonist analogs of LHRH which have been modified at the N-terminus by addition of either an acyl functional group or an acyl functional group together with an additional aminoacyl residue. The compounds of the present invention inhibit the secretion of gonadotropins by the pituitary gland and inhibit the release of steroids by the gonads.

In particular, the peptides of the present invention have the structure:

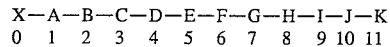

where the letters A through K represent aminoacyl residues and X represents an N-terminus-modifying acyl group. In accordance with the present invention, the residues are selected from the following:

X is an acyl group selected from the group consisting of (a) dihydroshikimyl, (b) 2-furoyl, (c) 3-furoyl, (d) tetrahydrofuro-2-yl, (e) tetrahydrofuro-3-yl, (f) (thien-2-yl)carbonyl, (g) (thien-3-yl)carbonyl, (h) (tetrahydrothien-2-yl)carbonyl, (i) (tetrahydrothien-3-yl)carbonyl, (j) pyrrol-2-yl)carbonyl, (k) (pyrrol-3-yl)carbonyl, (l) prolyl, (m) N-acetyl-prolyl, (n) 3-(indolin-3-yl)propionyl, (o) (indolin-3-yl)acetyl, (p) (indolin-2-yl)carbonyl, (q) (indolin-3-yl)carbonyl, (r) benzo[b]fur-2-yl)carbonyl, (s) (dihudrobenzo[b]fur-2-yl)carbonyl, (t) (tetrahydropyran-2-yl)carbonyl, (u) (tetrahydropyran-3-yl)carbonyl, (v) (piperidin-3-yl)carbonyl, (w) (N-acetylpiperidin-3-yl)carbonyl, (x) nicotinyl, optionally substituted with alkyl of from one to six carbon atoms, alkoxy of from one to six carbon atoms, halogen, or hydroxy, (y) isonicotinyl, optionally substituted with alkyl of from one to six carbon atoms, alkoxy of from one to six carbon atoms, halogen, or hydroxy, (z) picolinyl, (aa) 2-, 3- or 4-quinolinecarbonyl, optionally substituted with alkyl of from one to six carbon atoms, alkoxy of from one to six carbon atoms, halogen, or hydroxy; (bb) salicyl, (cc) shikimyl, and (dd) p-toluenesulfonyl.

A is absent or is an aminoacyl residue selected from the group consisting of β-alanyl, D-alanyl, 3-aminopropionyl, 4-aminobutyryl, 5-aminovaleryl, 6-aminohexanoyl, 7-aminoheptanoyl, 8-aminooctanoyl, 11-aminoundecanoyl, azaglycyl, glycyl, sarcosyl, and D-seryl.

B is an aminoacyl residue selected from the group consisting of D-phenylalanyl, D-3-(4-chlorophenyl)alanyl, D-3-(4-fluorophenyl)alanyl, D-3-(quinolin-3-yl)alanyl, sarcosyl, glycyl, azaglycyl, D-3,3-diphenylalanyl, $N^\alpha$-methyl-D-3-(naphth-2-yl)alanyl, and D-3-(naphth-2-yl)alanyl.

C is an aminoacyl residue selected from the group consisting of D-3-(4-chlorophenyl)alanyl, D-3,3-diphenylalanyl, D-3-(4-fluorophenyl)alanyl, D-3-(naphth-2-yl)alanyl, D-phenylalanyl, and D-3-(quinolin-3-yl)alanyl.

D is an aminoacyl residue selected from the group consisting of D-alanyl, D-3-(benzo[b]thien-2-yl)alanyl, glycyl, D-3-(naphth-1-yl)alanyl, D-3-(pyrid-3-yl)alanyl, D-3-(quinolin-3- yl)alanyl, and D-3-(thiazol-2-yl)alanyl.

E is an aminoacyl residue selected from the group consisting of glycyl, L-seryl, L-homoseryl, L-seryl(O-benzyl), and $N^\alpha(R^1)$-L seryl where $R^1$ is alkyl of from one to four carbon atoms.

F is an aminoacyl residue selected from the group consisting of $N^\alpha(R^1)$-alanyl, $N^\alpha(R^1)$-(3-(4-(3-amino-1,2,4-triazol-5-yl)amino)phenyl)alanyl, $N^\alpha((R^1)$-(3-(4-((3-amino-1,2,4-triazol-5-yl)amino)methyl)phenyl)alanyl, $N^\alpha(R^1)$-(3-(4-(3-amino-1,2,4-triazol-5-yl)amino)cyclohexyl)alanyl, $N^\alpha(R^1)$-(3-(4-(nicotinyl)amino)cyclohexyl)alanyl, $N^\alpha(R^1)$-(N-ε-nicotinyl)lysyl, $N^\alpha(R^1)$-(N-ε-(3-amino-1,2,4-triazol-5-yl))lysyl, $N^\alpha(R^1)$-3-(4-nitrophenyl)alanyl, $N^\alpha(R^1)$-3-(4-aminophenyl)alanyl, $N^\alpha(R^1)$-3-(4-aminocyclohexyl)alanyl, $N^\alpha(R^1)$-tyrosyl, $N^\alpha(R^1)$-tyrosyl(O-methyl), $N^\alpha(R^1)$-phenylalanyl, $N^\alpha(R^1)$-cyclohexylalanyl, $N^\alpha(R^1)$-glycyl, $N^\alpha(R^1)$- arginyl; N^α(R¹)-histidyl, and N^α(R¹)-homoarginyl; where R¹ is hydrogen or alkyl of from one to four carbon atoms.

G is an aminoacyl residue selected from the group consisting of glycyl, D-citrullyl, D-homocitrullyl, β-alanyl, and an aminoacyl residue of the structure

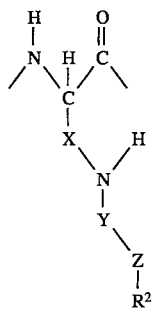

where X is selected from the group consisting of —(CH$_2$)$_n$— where n is one to six and

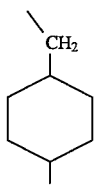

Y is absent or is an aminoacyl residue selected from the group consisting of D-alanyl, L-alanyl, 4-aminobutyryl, 5-aminopentanoyl, 6-aminohexanoyl, 7-aminoheptanoyl, 8-amino-octanoyl, 11-aminoundecanoyl, azaglycyl, D-3-(benzo[b]thien-2-yl)alanyl, L-3-(benzo[b]thien-2-yl)alanyl, D-3-(4-chlorophenyl)alanyl, D-cyclohexylanalyl, glycyl, D-histidyl, D-histidyl(benzyl), D-leucyl, D-3-(naphth-2-yl)alanyl, D-phenylalanyl, D-3-(pyrid-3-yl)alanyl, sarcosyl, seryl, D-seryl, D-threonyl, D-3-(thiazol-4-yl)alanyl, D-tryptyl, D-tyrosyl, D-tryosyl(O-methyl), and D-valyl.

Z is either absent or is an aminoacyl residue selected from the group consisting of D-alanyl, L-alanyl, azaglycyl, D-cyclohexylalanyl, glycyl, D-histidyl, D-phenylalanyl, 3-((4-(3-amino-1,2,4-triazol-5-yl)amino)phenyl)alanyl, (3-(4-((3-amino-1,2,4-triazol-5-yl)amino)methyl)phenyl)alanyl, sarcosyl, D-seryl, L-seryl, and

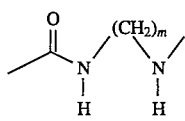

where m is an integer of from one to twelve, inclusive.

R² is 3-amino-1,2,4-triazol-5-yl or is an acyl group selected from the group consisting of acetyl; (4-acetylpiperazin-1-yl)carbonyl; (adamant-1-yl)carbonyl; benzoyl, optionally substituted with a group selected from alkyl of one to four carbon atoms, alkoxy of one to four carbon atoms, and halogen; butyryl; cycolhexylcarbonyl; dihydroshikimyl; formyl; nicotinyl; 2-furoyl; 2- and 6-hydroxynicotinyl; (indol-2-yl)carbonyl; isonicotinyl; (4-methylpiperazin-1-yl)carbonyl; (morphilin-1-yl)carbonyl; 2- and 6-methylnicotinyl; 1- and 2-naphthoyl optionally substituted with a group selected from alkyl of one to four carbon atoms, alkoxy of one to four arbon atoms, and halogen; picolyl; (piperazin-1-yl)carbonyl; propionyl, pyrazinoyl; pyridylacetyl; (pyrrolyl)carbonyl; (quinolinyl)carbonyl; salicyl; shikimyl; 2-(tetrahydrofuroyl), and (thien-2-yl)carbonyl.

H is an aminoacyl residue selected from the group consisting of L-leucyl; N(R¹)-L-leucyl; glycyl; sarcosyl; prolyl; L-valyl; L-cyclohexylalanyl; and N^α(R¹)-L-cyclohexylalanyl; where R¹ is hydrogen or alkyl of from one to six carbon atoms.

I is an aminoacyl residue selected from the group consisting of L-citrullyl; L-homocitrullyl; L-histidyl; L-(N-ε-isopropyl)lysyl; L-arginyl; and N^α(R¹)-L-arginyl; L-homoarginyl; L-2-amino-6-N^g-ethylguanidinohexanoyl; and L-2-amino-6-N^g, N^g-diethylguanidinohexanoyl.

J is an aminoacyl residue selected from the group consisting of L-prolyl;4-hydroxy-L-prolyl; L-pipecolyl; L-azetidinyl; L-2,8-tetrahydroisoquinoline-2-carbonyl, N(R¹)-L-leucyl; sarcosyl; glycyl; and N(R¹)-L-alanyl; where R¹ is hydrogen or alkyl of from one to six carbon atoms.

K is —NH(CH$_2$CH$_3$) or is an aminoacyl residue selected from the group consisting of D-alanylamide, D-alanyl(OH), D-glutamyl(OH), L-glutamyl(OH), N(R¹)-L-alanylamide, N(R¹)-D-alanylamide, sarcosamide, D-serylamide, and azaglycylamide, glycylamide, where R¹ is as defined above and with the proviso that when K is —NH(CH$_2$CH$_3$) then J is L-prolyl.

In another embodiment of the present invention there are provided pharmaceutical formulations for use in suppressing levels of sex hormones in a mammal comprising a sex hormone suppressing effective amount of a compound as defined above in combination with a pharmaceutically acceptable carrier.

In yet another embodiment of the present invention there is provided a method of suppressing levels of sex hormones in a mammal comprising administering to a mammal in need of such treatment a therapeutically effective amount of a compound as defined above.

DETAILED DESCRIPTION

As used throughout this specification and the mended claims, the term "halide" as used herein refers to bromo (Br), chloro (Cl), fluoro (F) or iodo (I).

The terms "resin" or "peptide resin" as used herein refer to resins of the type commonly used in the art of synthetic peptide preparation. Examples of such resins include, but are not limited to, methyl benzhydrylamine (MBHA) or benzhydrylamine (BHA) or Merrifield resin (i.e. chloromethylated polystyrene).

The term "alkyl" as used herein refers to divalent straight or branched group derived from a saturated hydrocarbon by the removal of a single hydrogen atom. Examples of alkyl include, but are not limited to methyl, ethyl, propyl, iso-propyl, butyl, sec-butyl, iso-butyl, tert-butyl, pentyl, hexyl, and the like.

The term "alkylene" refers to a straight or branched divalent group derived from a saturated hydrocarbon by the removal of two hydrogen atoms. Examples of alkylene include —CH$_2$—, —CH$_2$CH$_2$—, —CH(CH$_3$)CH$_2$— and the like.

The term "azetidinyl" refers to the cyclic aminoacyl residue derived from azetidine-2-carboxylic acid.

The term "cycloalkyl" refers to a monovalent cyclic hydrocarbon group derived from a cyclic saturated hydrocarbon group by the removal of a single hydrogen atom. Examples of cycloalkyl groups include cyclopropyl, cycobutyl, cyclohexyl, cycloheptyl, bicyclo[2.2.2]octane, and the like.

The term "cycloalkylene" refers to a divalent group derived from a saturated cyclic hydrocarbon by the removal to two hydrogens. Examples include cyclopentylene, cycohexylene, and the like.

The term "isonicotinyl" means the acyl group derived from isonicotinic acid, i.e. pyridine-4-carboxylic acid.

The term "nicotinyl" denotes the acyl group derived from nicotinic acid, i.e. pyridine-3-carboxylic acid.

"Picolinoyl" refers to the acyl group derived from picolinic acid, i.e. 2-pyridinecarboxylic acid.

"Shikimyl" denotes the acyl residue derived from shikimic acid or [3R-( 3α,4α,5β)-3,4,5-trihydroxy-1-cyclohexene-1-carboxylic acid and "dihydroshikimyl" refers to the fully saturated analog of shikimic acid.

Unless indicated otherwise by a "D" prefix, the stereochemistry of the alpha-carbon atom of the amino acids and aminoacyl residues in peptides described in this specification and the appended claims is the natural or "L" configuration. The Cahn-Ingold-Prelog "R" and "S" designations are used to specify the stereochemistry of chiral centers in certain of the acyl substituents at the N-terminus of the peptides of this invention. The designation "R,S" is meant to indicate a racemic mixture of the two enantiomeric forms. This nomenclature follows that described in R. S. Cahn, C. K. Ingold, and V. Prelog, *Angew. Cem., Int. Ed. Engl.*, 5:385–415 (1966).

For the most part, the names of naturally-occuring and non-naturally-occuring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)," *Biochemistry*, 14(2): 1975). To the extent that the names and abbreviations of amino acids and aminoacyl residues employed in this specification and appended claims differ from those suggestions, they will be made clear to the reader by the following.

"Atz" or "Atza" means the substituent group 3-amino-1,2,4-triazol-5-yl. "Bal" stands for 3-(benzo[b]thien-2-yl)alanine, with "Thial" and "Thiaz" representing 3-(thien-2-yl)alanine and 3-(thiazolyl)alanine, respectively.

"Cha" represents 3-cyclohexylalanine and various amino acids derived from phenylalanine by substitution of the phenyl group are represented by abbreviations such as "D4ClPhe," "D4FPhe," "D4NO$_2$Phe," and "D4NH$_2$Phe" which represent D-3-( 4-chlorophenyl)alanine, D-3-(4-fluorophenyl)alanine, D-3-(4-nitrophenyl)alanine, and D-3-(4-aminophenyl)alanine, respectively.

"Cit" and "HCit" stand for citrullyl and homocitrullyl (or L-2-amino-(6-aminocarbonylamino)hexanoic acid), respectively.

"Cha(4AmPyz)" represents a 3-((4-aminopyrazin-2-carbonyl)cyclohexyl)alanyl aminoacyl residue.

"DLys(Nic)" or "D-Lys(N-epsilon nicotinyl)" represents a D-lysine amino acid or aminoacyl residue substituted on the epsilon nitrogen atom of the side chain by a nicotinyl acyl group. Similarly, "DLys(Isonic)," "DLys(Shik)," "DLys(Fur)," and "DLys(THF)" represent D-lysine acylated on the epsilon nitrogen atom by an isonicotinyl, shikimyl, fur-2-oyl, or tetrahydrofur-2-oyl group. "DLys(Isp)," "DLys(Nisp)" or "D-Lys(N-epsilon isopropyl)" stand for a lysine substituted on the epsilon amino group of the lysine side-chain by an isopropyl group.

"Harg" stands for homoarginyl or L-2-amino-6-guanidinohexanoyl). "HargEt" and "HargEt$_2$" represent L-2-amino-6-N$^g$-ethylguanidinohexanoic acid and L-2-amino-6-N$^g$, N$^g$-diethylguanidinohexanoic acid, respectively.

"Aha" represents 4-aminoheptanboic acid; "Aca" represents 6-aminocaproic acid.; "Gaba" denotes 4-aminobutyric acid; and "Bala" represents beta-aminoalanine or 3-aminopropionic acid.

"D1Nal" and "D2Nal" represent D-3-(naphth-1-yl)alanine and D-3-(naphth-2-yl)alanine, respectively. "D3Pal" represents D-3-(pyrid-3-yl)alanine and "D3Qal" or "D3Qual" stands for D-3-(quinol-3-yl)alanine. "D-(4-Atza-)Phe" or "DAtzPhe" means D-3-(4-(3-amino-1H-1,2,4-triazol-5-yl)amino)phenyl)alanine and "D-(4-Atzame)Phe" or "D-(AtzMe)Phe" represents D-3-(4-(((3-amino-1H-1,2,4'-triazol- 5yl)amino)methyl)phenyl)alanine.

"Sar" and "SarNH$_2$" mean sarcosine or the amide of sarcosine, respectively.

The term "Aze" represents L-2-azetidinylcarbonyl, while "4-(p-OMeBzOl)Hala" stands for 4-(4-methoxybenzoyl)homoalanyl and "DLys(COdiAmpropShik)" refers to a D-Lysyl(N-ε-carbonyl-N',N"-diaminopropaneshikimyl)aminoacyl residue.

By the term "pharmaceutically acceptable salt" is meant salts recognized in the pharmaceutical formulation arts as non-toxic and sutable for use in formulations intended for use in human and animal treatment. Suitable acids and bases useful for this purpose are listed, for example, in the review article, "Pharmaceutical Salts" by S. N. Berge, et al., *J. Pharm. Sci.*, 66: 1–19(1977).

Representative examples of compounds contemplated as falling within the scope of the present invention include, but are not limited to the following:

N-Dihydroshikimyl-Gly-D2Nal-D4ClPhe-D3Pal-Ser-NMeTyr-DLys(N-epsilon-Nicotinyl)-Leu-Lys(N-epsilon-Isopropyl) -Pro-DAlaNH$_2$;

N-2-Furoyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-3Furoyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-Picolyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-Nicotinyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-Isonicotinyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-Salicyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N[(R,S )-Tetrahydrofur-2-oyl]-Gly-D2 Nal-D4ClPhe-D3Pal-Ser-NMeTyr-D Lys(Nicotinyl)-Leu-Lys(N-epsilon-Isopropyl)-Pro-DAlaNH$_2$;

N[(S)-Tetrahydrofur-2-oyl]-Gly-D2Nal-D4ClPhe-D3Pal-Ser-NMeTyr-DLys(Nicotinyl) -Leu-Lys(N-epsilon-Isopropyl)-Pro-DAlaNH$_2$;

N[(R) Tetrahydrofur-2-oyl]-Gly-D2Nal-D4ClPhe-D3Pal-Ser-NMeTyr-DLys(Nicotinyl) -Leu-Lys(N-epsilon-Isopropyl)-Pro-DAlaNH$_2$;

N-Nicotinyl-3Aminopropionyl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-Shikimyl-3 Aminopropionyl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-Nicotinyl-4Aminobutyryl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Shikimyl-4Aminobutyryl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Nicotinyl-5Aminovaleryl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Shikimyl-5Aminovaleryl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Shikimyl-DSer-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Nicotinyl-Gly-D2Nal-D4ClPhe-D3Pal-Ser-NMeTyr-DLys(Gly-Nicotinyl)-Leu-Lys(N-epsilon-Isopropyl)-Pro-DAlaNH$_2$;

N-Nicotinyl-Gly-D2Nal-D4ClPhe-D3Pal-Ser-NMeTyr-DLys(Azagly-Nicotinyl)-Leu-Lys(N-epsilon-Isopropyl)-Pro-DAlaNH$_2$;

N-Nicotinyl-Gly-D2Nal-D4ClPhe-D3Pal-Ser-NMeTyr-DLys(Azagly-2Furoyl)-Leu-Lys(N-epsilon-Isopropyl)-Pro-DAlaNH$_2$;

N-(R,S)Tetrahydrofur-2-oyl-Gly-D2Nal-D4ClPhe-D3Pal-Ser-NMeTyr-DLys(Azagly-Nicotinyl)-Leu-Lys(N-epsilon-Isopropyl)-Pro-DAlaNH$_2$;

N-(R,S)Tetrahydrofur-2-oyl-D2Nal-D4ClPhe-D3Pal-Ser-NMeTyr-DLys(Gly-Nicotinyl)-Leu-Lys(N-epsilon-Isopropyl)-Pro-DAlaNH$_2$;

N-(R,S)-Tetrahydro-Fur-2-oyl-Gly-D2Nal-D4ClPhe-D3Pal-Ser-NMeTyr-DCit-Leu-Arg-Pro-DAlaNH$_2$;

N-(R,S)-Tetrahydro-Fur-2-oyl-Gly-D2Nal-D4ClPhe-D3Pal-Ser-NMeTyr-DLys(AzaGly-2-furoyl)-Leu-Lys(N-epsilon-Isopropyl)-Pro-DAlaNH$_2$;

N-Shikimyl-Gly-D2Nal-D4ClPhe-D3Pal-Ser-NMeTyr-DCit-Leu-Arg-Pro-DAlaNH$_2$;

N-Nicotinyl-Gly-D2Nal-D4ClPhe-D3Pal-Ser-NMeTyr-DCit-Leu-Arg-Pro-DAlaNH$_2$;

N-Succinyl-Gly-D2Nal-D4ClPhe-D3Pal-Ser-NMeTyr-DCit-Leu-Arg-Pro-DAlaNH$_2$;

N-Shikimyl-DAla-D2Nal-D4ClPhe-D3Pal-Ser-NMeTyr-DCit-Leu-Arg-Pro-DAlaNH$_2$;

N-Shikimyl-DSer-D2Nal-D4ClPhe-D3Pal-Ser-NMeTyr-DCit-Leu-Arg-Pro-DAlaNH$_2$;

N-Nicotinyl-Sar-D2Nal-D4ClPhe-D3Pal-Ser-NMeTyr-DLys(Shik)-Leu-Arg-Pro-DAlaNH$_2$;

N-Shikimyl-Sar-D2Nal-D4ClPhe-D3Pal-Ser-NMeTyr-DLys(Shik)-Leu-Arg-Pro-DAlaNH$_2$;

N-Nicotinyl-DAla-D2Nal-D4ClPhe-D3Pal-Ser-NMeTyr-DLys(Shik)-Leu-Arg-Pro-DAlaNH$_2$;

N-Shikimyl-DAla-D2Nal-D4ClPhe-D3Pal-Ser-NMeTyr-DLys(Shik)-Leu-Arg-Pro-DAlaNH$_2$;

N-Nicotinyl-DSer-D2Nal-D4ClPhe-D3Pal-Ser-NMeTyr-DLys(Shik)-Leu-Arg-Pro-DAlaNH$_2$;

N-Shikimyl-DSer-D2Nal-D4ClPhe-D3Pal-Ser-NMeTyr-DLys(Shik)-Leu-Arg-Pro-DAlaNH$_2$;

N-Nicotinyl-DLys(Nic)-DSer-D2Nal-D4ClPhe-D3Pal-Ser-NMeTyr-DLys(Shik)-Leu-Arg-Pro-DAlaNH$_2$;

N-Shikimyl-DLys(Nic)-D2Nal-D4ClPhe-D3Pal-Ser-NMeTyr-DLys(Shik)-Leu-Arg-Pro-DAlaNH$_2$;

N-Nicotinyl-DLys(Shik)-DSer-D2Nal-D4ClPhe-D3Pal-Ser-NMeTyr-DLys(Shik)-Leu-Arg-Pro-DAlaNH$_2$;

N-Shikimyl-DLys(Shik)-D2Nal-D4ClPhe-D3Pal-Ser-NMeTyr-DLys(Shik)-Leu-Arg-Pro-DAlaNH$_2$;

N-Nicotinyl-Gly-D2Nal-D4ClPhe-D3Pal-Ser-NMeTyr-DLys(Shik)-Leu-Arg-Pro-DAlaNH$_2$;

N-(S)-Tetrahydrofur-2-oyl-Gly-D2Nal-D4ClPhe-D3Pal-Ser-NMeTyr-DLys(Shik)-Leu-Arg-Pro-DAlaNH$_2$;

N-(R)-Tetrahydrofur-2-oyl-Gly-D2Nal-D4ClPhe-D3Pal-Ser-NMeTyr-DLys(Shik)-Leu-Arg-Pro-DAlaNH$_2$;

N-Shikimyl-Gly-D2Nal-D4ClPhe-D3Pal-Ser-NMeTyr-DLys(Gly-Nic)-Leu-Arg-Pro-DAlaNH$_2$;

N-Shikimyl-Gly-D2Nal-D4ClPhe-D3Pal-Ser-NMeTyr-DLys(DSer-Nic)-Leu-Arg-Pro-DAlaNH$_2$;

N-Shikimyl-Gly-D2Nal-D4ClPhe-D3Pal-Ser-NMeTyr-DLys(Gly-Shik)-Leu-Arg-Pro-DAlaNH$_2$;

N-Shikimyl-Gly-D2Nal-D4ClPhe-D1Nal-Ser-NMeTyr-DLys(Shik)-Leu-Arg-Pro-DAlaNH$_2$;

N-Shikimyl-Gly-D2Nal-D4ClPhe-D3Pal-Ser-NMePhe-DLys(Shik)-Leu-Arg-Pro-DAlaNH$_2$;

N-Shikimyl-Gly-D2Nal-D4ClPhe-D3Pal-Ser-NMeTyr-DLys(Shik)-Ile-Arg-Pro-DAlaNH$_2$;

N-Shikimyl-Gly-D2Nal-D4ClPhe-D3Pal-Ser-NMeTyr-DLys(Shik)-NMeLeu-Arg-Pro-DAlaNH$_2$;

N-Shikimyl-Gly-D2Nal-D4ClPhe-D3Pal-Ser-NMeTyr-DLys(Shik)-Leu-Arg-Aze-DAlaNH$_2$;

N-Shikimyl-Gly-D2Nal-D4ClPhe-D3Pal-Ser-NMeTyr-DLys(GlyGlyNic)-Leu-Arg-Pro-DAlaNH$_2$;

N-(L-Gulonyl)-Gly-D2Nal-D4ClPhe-D3Pal-Ser-NMeTyr-DLys(Gly-L-Gulonyl)-Leu-Arg-Pro-DAlaNH$_2$;

N-Nicotinyl-Gly-D2Nal-D4ClPhe-D3Pal-Ser-NMeTyr-DLys(Gly-Shik)-Leu-Arg-Pro-DAlaNH$_2$;

N-Nicotinyl-Gly-D2Nal-D4ClPhe-D3Pal-Ser-NMeTyr-DLys(Shik)-Ile-Arg-Pro-DAlaNH$_2$;

Nicotinyl-Gly-D2Nal-D4ClPhe-D3Pal-Ser-NMeTyr-DLys(Shikimyl)-NMeLeu-Arg-Pro-DAlaNH$_2$;

N-Nicotinyl-Gly-D2Nal-D4ClPhe-D3Pal-Ser-NMeTyr-DLys(Shikimyl)-Leu-Arg-Aze-DAlaNH$_2$;

N-Nicotinyl-DSer-D2Nal-D4ClPhe-D3Pal-Ser-NMeTyr-DLys(Shikimyl)-Leu-Harg-Pro-DAlaNH$_2$;

N(2-Furoyl)-Gly-D2Nal-D4ClPhe-D3Pal-Ser-NMeTyr-DLys(Shik)-Leu-Harg-Pro-DAlaNH$_2$;

N-Shikimyl-Gly-D2Nal-D4ClPhe-D3Pal-Ser-NMeTyr-DLys(Shik)-Leu-Harg-Pro-DAlaNH$_2$;

N-Nicotinyl-Gly-D2Nal-D4ClPhe-D3Pal-Ser-NMeTyr-DLys(Gly-Shik)-Leu-Harg-Pro-DAlaNH$_2$;

N-Nicotinyl-Gly-D2Nal-D4ClPhe-D3Pal-Ser-NMeTyr-DLys(Nicotinyl)-Leu-Harg-Pro-DAlaNH$_2$; N-(3-Quinolinyl)-Gly-D2Nal-D4ClPhe-D3Pal-Ser-NMeTyr-DLys(Shikimyl)-Leu-Harg-Pro-DAlaNH$_2$;

N-Nicotinyl-Gly-D2Nal-D4ClPhe-D3Pal-Ser-NMePhe-DLys(Shik)-Leu-Harg-Pro-DAlaNH$_2$;

N-Nicotinyl-Gly-D2Nal-D4ClPhe-D3Pal-Ser-NMe-Phe(NO$_2$)-DLys(Shik)-Leu-Harg-Pro-DAlaNH$_2$;

N-Shikimyl-Gly-D2Nal-D4ClPhe-D3Pal-Ser-NMe-Phe(NO$_2$)-DLys(Shik)-Leu-Harg-Pro-DAlaNH$_2$;

N-Nicotinyl-Gly-D2Nal-D4ClPhe-D3Pal-Ser-NMeTyr-DLys(Nic)-Leu-Arg-Pro-DAlaNH$_2$;

N-(R,S)-Tetrahydrofur-2oyl-Gly-D2Nal-D4ClPhe-D3Pal-Ser-NMeTyr-DLys(Gly-Nic)-Leu-Arg-Pro-DAlaNH$_2$;

N-Shikimyl-Gly-D2Nal-D4ClPhe-D3Pal-Ser-NMeTyr-DLys(Nic)-Leu-Arg-Aze-DAlaNH$_2$;

N-Nicotinyl-3-Aminopropionyl-D2Nal-D4ClPhe-D3Pal-Ser-NMeTyr-DLys(Shikimyl)-Leu-Arg-Pro-DAlaNH$_2$;

N-Shikimyl-3-Aminopropionyl-D2Nal-D4ClPhe-D3Pal-Ser-NMeTyr-DLys(Shik)-Leu-Arg-Pro-DAlaNH$_2$;

N-Nicotinyl-3-Aminopropionyl-D2Nal-D4ClPhe-D3Pal-Ser-NMeTyr-DLys(Shik)-Leu-Harg-Pro-DAlaNH$_2$;

N-Shikimyl-D4ClPhe-D3Pal-Ser-NMeTyr-DLys(GlyNic)-Leu-Lys(Isp)-Pro-DAlaNH$_2$;

N-Nicotinyl-Azagly-D2Nal-D4ClPhe-D3Pal-Ser-NMeTyr-DLys(Azagly-Nic)-Leu-Lys(Isp)-Pro-DAlaNH$_2$;

N-Nicotinyl-Azagly-D4ClPhe-DBal-Ser-NMeTyr-DLys(Nic)-Leu-Lys(Isp)-Pro-DAlaNH$_2$;

N-(2-Furoyl)-Azagly-D4ClPhe-DBal-Ser-NMeTyr-DLys(Nic)-Leu-Lys(Isp)-Pro-DAlaNH$_2$;

N-Isonicotinyl-Azagly-D4ClPhe-DBal-Ser-NMeTyr-DLys(Nic)-Leu-Lys(Isp)-Pro-DAlaNH$_2$;

N-Nicotinyl-Azagly-D4ClPhe-D1Nal-Ser-NMeTyr-DLys(Nic)-Leu-Lys(Isp)-Pro-DAlaNH$_2$;

N-Nicotinyl-Sar-D4ClPhe-DBal-Ser-NMeTyr-DLys(Nic)-Leu-Lys(Isp)-Pro-DAlaNH$_2$;

Nic-Gly-Sar-D4ClPhe-D1Nal-Ser-NMeTyr-DLys(Nic)-Leu-Lys(Isp)-Pro-DAlaNH$_2$;

Nic-Gly-Sar-D4ClPhe-DBal-Ser-NMeTyr-DLys(Nic)-Leu-Lys(Isp)-Pro-DAlaNH$_2$;

N-Nicotinyl-3-Aminopropionyl-D2Nal-D4ClPhe-DBal-Ser-NMeTyr-DLys(N-epsilon-Nicotinyl) -Leu-Lys(N-epsilon-Isopropyl)-Pro-DAlaNH$_2$;

N-Nicotinyl-Azagly-D2Nal-D4ClPhe-D3Pal-Ser-NMeTyr-DLys(Nic)-Leu-Lys(Isp)-Pro-DAlaNH$_2$;

N-Salicyl-Azagly-D2Nal-D4ClPhe-D3Pal-Ser-NMeTyr-DLys(Nic)-Leu-Lys(Isp)-Pro-DAlaNH$_2$;

N-Isonicotinyl-Azagly-D2Nal-D4ClPhe-D3Pal-Ser-NMeTyr-DLys(Nic)-Leu-Lys(Isp)-Pro-DAlaNH$_2$;

N-Tosyl-Azagly-D2Nal-D4ClPhe-D3Pal-Ser-NMeTyr-DLys(Nic)-Leu-Lys(Isp)-Pro-DAlaNH$_2$;

N-(R,S)-Tetrahydrofur-2-oyl-Gly-D2Nal-D4ClPhe-D3Pal-Ser-Tyr-DLys(Nicotinyl)-Leu-Lys(Isp)-Pro-SarNH$_2$;

N-(R,S)-Tetrahydrofur-2-oyl-Gly-D2Nal-D4ClPhe-D3Pal-Ser-Lys(Nic)-DLys(Nicotinyl)-Leu-Lys(Isp)-Pro-SarNH$_2$;

N-(R,S)-Tetrahydrofur-2-oyl-Gly-D2Nal-D4ClPhe-D3Pal-Ser-Tyr-DCit-Leu-Arg-Pro-SarNH$_2$;

N-(R,S) Tetrahydrofur-2-oyl-Gly-D2Nal-D4ClPhe-D3Pal-Ser-Tyr-DHcit-Leu-Arg-Pro-SarNH$_2$;

N-(R,S) Tetrahydrofur-2-oyl-Gly-D2Nal-D4ClPhe-D3Pal-Ser-Tyr-DHcit-Leu-Lys(Isp)-Pro-SarNH$_2$;

N-(R,S) Tetrahydrofur-2-oyl-Gly-D2Nal-D4ClPhe-D3Pal-Ser-Arg-D-4(pOMeBzol)Hala-Leu-Arg-Pro-SarNH$_2$;

N-(R,S)-Tetrahydrofur-2-oyl-Gly-D2Nal-D4ClPhe-D3Pal-Ser-Tyr-DHarg(Et$_2$)-Leu-Harg(Et$_2$)-Pro-SarNH$_2$;

N-(R,S)-Tetrahydrofur-2-oyl-Gly-D2Nal-D4ClPhe-D3Pal-Ser-NMePhe(Atz)-DPhe(Atz)-Leu-Lys(Isp)-Pro-SarNH$_2$;

N-(R,S)-Tetrahydrofur-2-oyl-Gly-D2Nal-D4ClPhe-D3Pal-Ser-Phe(Atz)-DPhe(Atz)-Leu-Lys(Isp)-Pro-SarNH$_2$;

N-(R,S)-Tetrahydrofur-2-oyl-Gly-D2Nal-D4ClPhe-D3Pal-Ser-NMeTyr-DLys(Azagly-2Fur)-Leu-Lys(Isp)-Pro-SarNH$_2$;

N-(R,S)-Tetrahydrofur-2-oyl-Gly-D2Nal-D4ClPhe-D3Pal-Ser-NMeTyr-DLys(Azagly-Nic)-Leu-Lys(Isp)-Pro-SarNH$_2$;

N-(R,S)-Tetrahydrofur-2-oyl-Gly-D2Nal -D4ClPhe-D3Pal-Ser-NMeTyr-DLys(Gly-Nic)-Leu-Lys(Isp)-Pro-SarNH$_2$;

N-Nicotinyl-Gly-D2Nal-D4ClPhe-D3Pal-Ser-NMeTyr-DLys(Shik)-Leu-Harg-Pro-DAlaNH$_2$;

N-(R,S)-Tetrahydrofur-2-oyl-Gly-D2Nal-D4ClPhe-D3Pal-Ser-NMeTyr-DLys(Shik)-Leu-Harg-Pro-DAlaNH$_2$;

N-(R,S)-Tetrahydrofur-2-oyl-Gly-D2Nal-D4ClPhe-D3Pal-Ser-NMeTyr-DLys(Shik)-Leu-Harg-Pro-SarNH$_2$;

N-Shikimyl-Gly-D2Nal-D4ClPhe-D3Pal-Ser-NMeTyr-DLys(Shik)-Leu-Harg-Pro-SarNH$_2$;

N-Nicotinyl-Gly-D2Nal-D4ClPhe-D3Pal-Ser-NMePhe(Atz)-DLys(Shik)-Leu-Harg-Pro-DAlaNH$_2$;

N-Nicotinyl-Gly-D3Qal-D4ClPhe-D3Pal-Ser-NMeTyr-DLys(Shik)-Leu-Harg-Pro-DAlaNH$_2$;

N-Nicotinyl-Gly-D2Nal-D4ClPhe-D3Pal-Ser-NMeTyr-DLys(COdiAmpropShik)-Leu-Harg-Pro-SarNH$_2$;

N-(R,S)-Tetrahydrofur-2-oyl-Gly-D2Nal-D4ClPhe-D3Pal-Ser-NMeTyr-DLys(COdiAmpropShik)-Leu-Harg-Pro-SarNH$_2$;

N-(R,S)-Tetrahydrofur-2-oyl-Gly-D2Nal-D4ClPhe-D3Pal-Ser-NMeTyr-DLys(COdiAmpropShik)-Leu-Lys(Isp)-Pro-DAlaNH$_2$;

N-(R,S)-Tetrahydrofur-2-oyl-Gly-D2Nal-D4ClPhe-D3Pal-Ser-NMeTyr-DLys(COdiAmpropShik)-Leu-Lys(Isp)-Pro-SarNH$_2$;

N-Nicotinyl-Gly-D3Qal-D4ClPhe-D3Pal-Ser-cis-Cha(4AmPrz)-DLys(Pic)-Leu-Arg-Pro-DAlaNH$_2$;

NShikimyl-Gly-D2Nal-D4ClPhe-D3Pal-Ser-NMeTyr-DLys(N-epsilon-Nicotinyl )-Leu-Lys(N-epsilon-Isopropyl)-Pro-SarNH$_2$;

N-Dihydroshikimyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$;

N-2Furoyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$;

N-3Furoyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-Picolyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$;

N-Nicotinyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$;

N-Isonicotinyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$;

N-Salicyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$;

N-Tosyl-D2Nal-D4ClPhe-D3Pal-Ser-NMeTyr-DCit-Leu-Arg-Pro-DAlaNH$_2$;

N-(S)-Tetrahydrofur-2-oyl-D2Nal-D4ClPhe-D3Pal-Ser-NMeTyr-DLys(Nic)-Leu-Lys(Isp)-Pro-DAlaNH$_2$;

N-(R)-Tetrahydrofur-2-oyl-D2Nal-D4ClPhe-D3Pal-Ser-NMeTyr-DLys(Nic)-Leu-Lys(Isp)-Pro-DAlaNH$_2$;

N-(S)-Tetrahydrofur-3-oyl-D2Nal-D4ClPhe-D3Pal-Ser-NMeTyr-DLys(Nic)t-Leu-Lys(Isp)-Pro-DAlaNH$_2$;

N-(R)-Tetrahydrofur-3-oyl-D2Nal-D4ClPhe-D3Pal-Ser-NMeTyr-DLys(Nic)t-Leu-Lys(Isp)-Pro-DAlaNH$_2$;

N-Shikimyl-D2Nal-D4ClPhe-D3Pal-Ser-NMeTyr-DLys(Nic)t-Leu-Lys(Isp)-Pro-DAlaNH$_2$;

N-2-Furoyl-D2Nal-D4ClPhe-D3Pal-Ser-NMeTyr-DLys(Nic)-Leu-Lys(Isp)-Pro-DAlaNH$_2$;

N-3-Furoyl-D2Nal-D4ClPhe-D3Pal-Ser-NMeTyr-DLys-(Nic)-Leu-Lys(Isp)-Pro-DAlaNH$_2$;

N-Thienyl-2-carbonyl-D2Nal-D4ClPhe-D3Pal-Ser-NMeTyr-DLys(Nic)-Leu-Lys(Isp)-Pro-DAlaNH$_2$;

N-Nicotinyl-D2Nal-D4ClPhe-D3Pal-Ser-NMeTyr-DLys-(Nic)-Leu-Lys(Isp)-Pro-DAlaNH$_2$;

N-Picolinoyl-D2Nal-D4ClPhe-D3Pal-Ser-NMeTyr-DLys(Nic)-Leu-Lys(Isp)-Pro-DAlaNH$_2$;

N-(6-Hydroxy)nicotinyl-D2Nal-D4ClPhe-D3Pal-Ser-NMeTyr-DLys(Nic)-Leu-Lys(Isp)-Pro-DAlaNH$_2$;

N-Isonicotinyl-D2Nal-D4ClPhe-D3Pal-Ser-NMeTyr-DLys(Nic)-Leu-Lys(Isp)-Pro-DAlaNH$_2$;

N-(3-Pyridylacetyl)-D2Nal-D4ClPhe-D3Pal-Ser-NMeTyr-DLys(Nic)-Leu-Lys(Isp)-Pro-DAlaNH$_2$;

N-Shikimyl-D2Nal-D4ClPhe-D3Pal-Ser-Lys(Nic)-DLys-(Nic)-Leu-Lys(Isp)-Pro-DAlaNH$_2$;

N-Nicotinyl-D2Nal-D4ClPhe-D3Pal-Ser-Lys(Nic)-DLys(Nic)-Leu-Lys(Isp)-Pro-DAlaNH$_2$;

N-Shikimyl-D2Nal-D4ClPhe-D3Pal-Ser-Tyr-DLys(Nic)-Leu-Lys(Isp)-Pro-DAlaNH$_2$;

N-(S)-Tetrahydofur-2-oyl-D2Nal-D4ClPhe-D3Pal-Ser-NMeTyr-DCit-Leu-Arg-Pro-DAlaNH$_2$;

N-(R)-Tetrahydofur-2-oyl-D2Nal-D4ClPhe-D3Pal-Ser-NMeTyr-DCit-Leu-Arg-Pro-DAlaNH$_2$;

N-(R)-5-Oxo-tetrahydorofur-2-oyl-D2Nal-D4ClPhe-D3Pal-Ser-NMeTyr-DCit-Leu-Arg-Pro-DAlaNH$_2$;

N-(S)-5-Oxo-tetrahydorofur-2-oyl-D2Nal-D4ClPhe-D3Pal-Ser-NMeTyr-DCit-Leu-Arg-Pro-DAlaNH$_2$;

N-Shikimyl-D2Nal-D4ClPhe-D3Pal-Ser-NMeTyr-DCit-Leu-Arg-Pro-DAlaNH$_2$;

N-2-Furoyl-D2Nal-D4ClPhe -D3Pal-Ser-NMeTyr-DCit-Leu-Arg-Pro-DAlaNH$_2$;

N-Isonicotinyl-D2Nal-D4ClPhe-D3Pal-Ser-NMeTyr-DCit-Leu-Arg-Pro-DAlaNH$_2$;

N-Picolinoyl-D2Nal-D4ClPhe-D3Pal-Ser-NMeTyr-DCit-Leu-Arg-Pro-DAlaNH$_2$;

N-Nicotinyl-D2Nal-D4ClPhe-D3Pal-Ser-NMeTyr-DCit-Leu-Arg-Pro-DAlaNH$_2$;

N-(3-Pyridylacetyl)-D2Nal-D4ClPhe-D3Pal-Ser-NMeTyr-DCit-Leu-Arg-Pro-DAlaNH$_2$; and N-Shikimyl-D2Nal-D4ClPhe-D3Pal-Ser-NMeTyr-DLys(Shik)-Leu-Harg-Pro-DAlaNH$_2$.

In one embodiment of the present invention, the aminoacyl residue A is absent, and the peptides of the present invention are decapapetides modified at the N-terminus with an acyl function and possess the structure $$X-B-C-D-E-F-G-H-I-J-K$$
$$0\ \ 1\ \ 2\ \ 3\ \ 4\ \ 5\ \ 6\ \ 7\ \ 8\ \ 9\ \ 10$$

where X, B, C, D, E, F, G, H, I, J, and K are as defined above.

Preferred compounds of the present invention have the structure

where X is an acyl group selected from the group consisting of tetrahydrofur-3-oyl, (tetrahydrothien-2-yl)carbonyl, (pyrrol-2-yl)carbonyl, prolyl, (indolin-2-yl)carbonyl, 3-(indolin-3-yl)propionyl, (dihydrobenzo[b]fur-2-yl)carbonyl, and (tetrahydropyran-2-yl)carbonyl.

AA$^6$ is an aminoacyl residue selected from the group consisting of tyrosyl, arginyl, N$^\alpha$-methyltyrosyl, lysyl(N-epsilon-(3'-amino-1H-1',2',4'-triazol-5-yl)), and N$^\alpha$-methyl-3-(4-(3'-amino-1H-1',2',4'-triazol-5-ylmethyl)phenyl)alanyl.

AA$^7$ is an aminoacyl residue selected from the group consisting of D-citrullyl, D-homocitrullyl, D-lysyl(N-epsilon nicotinyl), D-lysyl(N-epsilon glycyl nicotinyl), D-lysyl(N-epsilon azaglycyl nicotinyl), D-lysyl(N-epsilon shikimyl), D-lysyl(N-epsilon glycyl shikimyl), D-lysyl(N-epsilon azaglycyl shikimyl), D-lysyl(N-epsilon dihydroshikimyl), D-lysyl(N-epsilon glycyl dihydroshikimyl), D-lysyl(N-epsilon azaglycyl dihydroshikimyl), D-lysyl(N-epsilon fur-2-oyl), D-lysyl(N-epsilon glycyl fur-2-oyl), D-lysyl(N-epsilon azaglycyl fur-2-oyl), D-lysyl(N-epsilon tetrahydrofur-2-oyl), D-lysyl(N-epsilon glycyl tetrahydrofur-2-oyl), and D-lysyl(N-epsilon azaglycyl tetrahydrofur-2-oyl).

AA$^9$ is an aminoacyl group selected from the group consisting of lysyl(N-epsilon isopropyl), arginyl, L-(N$^g$, N$^g$-diethylhomoarginyl), and homoarginyl.

AA$^{11}$ is an aminoacyl residue selected from the group consisting of D-alanylamide, and D-sarcosamide.

Examples of compounds of this type include
N-Shikimyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-(R,S)-Tetrahydrofur-2-oyl-Gly-D2Nal-D4ClPhe-D3Pal-Ser-NMeTyr-DLys(Azagly-Nicotinyl) -Leu-Lys(N-epsilon-Isopropyl)-Pro-DAlaNH$_2$;

N-(R,S)-Tetrahydrofur-2-oyl-D2Nal-D4ClPhe-D3Pal-Ser-NMeTyr-DLys(Gly-Nicotinyl) -Leu-Lys(N-epsilon-Isopropyl)-Pro-DAlaNH$_2$;

N-(R,S)-Tetrahydro-Fur-2-oyl-Gly-D2Nal-D4ClPhe-D3Pal-Ser-NMeTyr-DCit-Leu-Arg-Pro-DAlaNH$_2$;

N-Shikimyl-Gly-D2Nal-D4ClPhe-D3Pal-Ser-NMeTyr-DCit-Leu-Arg-Pro-DAlaNH$_2$;

N-Shikimyl-Gly-D2Nal-D4ClPhe-D3Pal-Ser-NMeTyr-DLys(Shik)-Leu-Arg-Pro-DAlaNH$_2$; and N-Nicotinyl-Gly-D2Nal-D4ClPhe-D3Pal-Ser-NMeTyr-DLys(Shik)-Leu-Harg-Pro-DAlaNH$_2$.

In a particularly preferred embodiment, compounds of this invention have the structure:

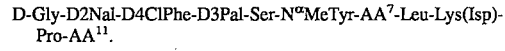

where X is an acyl group selected from the group consisting of tetrahydrofuro-2-yl furo-2-yl, nicotinyl, isonicotinyl, shikimyl, dihydroshikimyl, (tetrahydrothien-2-yl)carbonyl, pyrrol-2-yl)carbonyl, prolyl, (indol-2-yl)carbonyl, 3-(indol-3lyl)pripionyl, (dihydrobenzo[b]-fur-2-yl)carbonyl, and (tetrahydropyran-2-yl)carbonyl.

AA$^7$ is an aminoacyl residue selected from the group consisting of D-citrullyl, D-lysyl(N-epsilon nicotinyl), D-lysyl(N-epsilon glycyl nicotinyl), D-lysyl(N-epsilon azaglycyl nicotinyl), D-lysyl(N-epsilon shikimyl), D-lysyl(N-epsilon glycyl shikimyl), D-lysyl(N-epsilon azaglycyl shikimyl), D-lysyl(N-epsilon dihydroshikimyl), D-lysyl(N-epsilon glycyl dihydroshikimyl), D-lysyl(N-epsilon azaglycyl dihydroshikimyl), D-lysyl(N-epsilon fur-2-oyl), D-lysyl(N-epsilon glycyl fur-2-oyl), D-lysyl(N-epsilon azaglycyl fur-2-oyl), D-lysyl(N-epsilon tetrahydrofur-2-oyl), D-lysyl(N-epsilon glycyl tetrahydrofur-2-oyl), and D-lysyl(N-epsilon azaglycyl tetrahydrofur-2-oyl).

AA$^{11}$ is an aminoacyl residue selected from the group consisting of D-alanylamide, and D-sarcosamide.

Specific compounds of this embodiment are
N[(R,S)-Tetrahydrofur-2-oyl]-Gly-D2Nal-D4ClPhe-D3Pal-Ser-NMeTyr-DLys(Nicotinyl) -Leu-Lys(N-epsilon-Isopropyl)-Pro-DAlaNH$_2$;

N[(S)-Tetrahydrofur-2-oyl]-Gly-D2Nal-D4ClPhe-D3Pal-Ser-NMeTyr-DLys(Nicotinyl) -Leu-Lys(N-epsilon-Isopropyl)-Pro-DAlaNH$_2$;

N[(R) Tetrahydrofur-2-oyl]-Gly-D2Nal-D4ClPhe-D3Pal-Ser-NMeTyr-DLys(Nicotinyl) -Leu-Lys(N-epsilon-Isopropyl)-Pro-DAlaNH$_2$;

N-(R,S)-Tetrahydrofur-2-oyl-Gly-D2Nal-D4ClPhe-D3Pal-Ser-NMeTyr-DLys(Azagly- 2Fur)-Leu-Lys(Isp)-Pro-DAlaNH$_2$;

N-Shik-D2Nal-D4ClPhe-D3Pal-Ser-NMeTyr-DLys(Azagly-Nic)-Leu-Lys(Isp)-Pro-DAlaNH$_2$;

N-Shik-D2Nal-D4ClPhe-D3Pal-Ser-NMeTyr-DLys(Azagly-2Fur)-Leu-Lys(Isp)-Pro-DAlaNH$_2$;

N-(2-Furoyl)-Azagly-D2Nal-D4ClPhe-D3Pal-Ser-NMeTyr-DLys(-Nic)-Leu-Lys(Isp)-Pro-DAlaNH$_2$;

N-(R,S) Tetrahydrofur-2-oyl-Gly-D2Nal-D4ClPhe-D3Pal-Ser-NMeTyr-DLys(Nicotinyl)-Leu-Lys(Isp)-Pro-SarNH$_2$;

N-(S)-Tetrahydrofur-2-oyl-Gly-D2Nal-D4ClPhe-D3Pal-Ser-NMeTyr-DLys(Nicotinyl) -Leu-Lys(Isp)-Pro-SarNH$_2$;

N-(R)-Tetrahydrofur-2-oyl-Gly-D2Nal-D4ClPhe-D3Pal-Ser-NMeTyr-DLys(Nicotinyl) -Leu-Lys(Isp)-Pro-SarNH$_2$;

N-(R,S)-Tetrahydrofur-2-oyl-Gly-D2Nal-D4ClPhe-D3Pal-Ser-NMePhe(Me-Atz)-DPhe(Me-Atz)-Leu-Lys(Isp)-Pro-SarNH$_2$;

N-(R,S)-Tetrahydrofur-2-oyl-Gly-D2Nal-D4ClPhe-D3Pal-Ser-Lys(Atz)-DLys(Atz)-Leu-Lys(Isp)-Pro-SarNH$_2$;

N-(R,S)-Tetrahydrofur-2-oyl-Gly-D2Nal-D4ClPhe-D3Pal-Ser-Tyr-DLys(Nicotinyl)-Leu-Lys(Isp)-Pro-DAlaNH$_2$;

N-(R,S)-Tetrahydrofur-2-oyl-Gly-D2Nal-D4ClPhe-D3Pal-Ser-Lys(Nic)-DLys(Nicotinyl)-Leu-Lys(Isp)-Pro-DAlaNH$_2$;

N-(R,S)-Tetrahydrofur-2-oyl-Gly-D2Nal-D4ClPhe-D3Pal-Ser-Tyr-DCit-Leu-Arg-Pro-DAlaNH$_2$;

N-(R,S)-Tetrahydrofur-2-oyl-Gly-D2Nal-D4ClPhe-D3Pal-Ser-Tyr-DHcit-Leu-Arg-Pro-DAlaNH$_2$;

N-(R,S) Tetrahydrofur-2-oyl-Gly-D2Nal-D4ClPhe-D3Pal-Ser-Tyr-DHcit-Leu-Lys(Isp)-Pro-DAlaNH$_2$;

N-(R,S)-Tetrahydrofur-2-oyl-Gly-D2Nal-D4ClPhe-D3Pal-Ser-Arg-D-4(pOMeBzol)Hala-Leu-Arg-Pro-DAlaNH$_2$;

N-(R,S)-Tetrahydrofur-2-oyl-Gly-D2Nal-D4ClPhe-D3Pal-Ser-Tyr-DHarg(Et$_2$)-Leu-Harg(Et $_2$)-Pro-DAlaNH$_2$;

N-(R,S)-Tetrahydrofur-2-oyl-Gly-D2Nal-D4ClPhe-D3Pal-Ser-NMePhe(Atz)-DPhe(Atz)-Leu-Lys(Isp)-Pro-DAlaNH$_2$;

N-(R,S)-Tetrahydrofur-2-oyl-Gly-D2Nal-D4ClPhe-D3Pal-Ser-Phe(Atz)-DPhe(Atz)-Leu-Lys(Isp)-Pro-DAlaNH$_2$;

N-(R,S)-Tetrahydrofur-2-oyl-Gly-D2Nal-D4ClPhe-D3Pal-Ser-NMePhe(Me-Atz)-DPhe(Me-Atz)-Leu-Lys(Isp)-Pro-DAlaNH$_2$;

N-(R,S)-Tetrahydrofur-2-oyl-Gly-D2Nal-D4ClPhe-D3Pal-Ser-Lys(Atz)-DLys(Atz)-Leu-Lys(Isp)-Pro-DAlaNH$_2$;

N-(S)-2-Tetrahydrofuroyl-Gly-2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-(S)-2-Tetrahydrofuroyl-Gly-2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-(S)-2-Tetrahydrofuroyl-Gly-D2Nal-D4ClPhe-D3Pal-DSer-NMeTyr-DLys(N-epsilon-Nicotinyl) -Leu-Lys(N-epsilon-Isopropyl)-Pro-DAlaNH$_2$;

N-(S)-2-Tetrahydrofuroyl-Gly-D2Nal-D4ClPhe-3Pal-Ser-NMeTyr-DLys(N-epsilon-Nicotinyl) -Leu-Lys(N-epsilon-Isopropyl)-Pro-DAlaNH$_2$;

N-(S)-2-Tetrahydrofuroyl-Gly-D2Nal-D4ClPhe-D3Pal-Ser-NMeTyr-DLys(N-epsilon-Nicotinyl) -Leu-Lys(N-epsilon-Isopropyl)-Pro-DAlaOH;

N-(S)-2-Tetrahydrofuroyl-Gly-D2Nal-D4ClPhe-D3Pal-Ser-NMeTyr-Lys(N-epsilon-Nicotinyl) -Leu-Lys(N-epsilon-Isopropyl)-Pro-DAlaNH$_2$;

N-(S)-2-Tetrahydrofuroyl-Gly-D2Nal-4ClPhe-D3Pal-Ser-NMeTyr-DLys(N-epsilon-Nicotinyl) -Leu-Lys(N-epsilon-Isopropyl)-Pro-DAlaNH$_2$;

N-(S)-2-Tetrahydrofuroyl-Gly-D2Nal-D4ClPhe-3DPal-Ser-NMeTyr-DLys(N-epsilon-Nicotinyl) -DLeu-Lys(N-epsilon-Isopropyl)-Pro-DAlaNH$_2$;

N-(S)-2-Tetrahydrofuroyl-Gly-D2Nal-D4ClPhe-D3Pal-Ser-NMeTyr-DLys(N-epsilon-Nicotinyl) -Leu-Lys(N-epsilon-Isopropyl)-DPro-DAlaNH$_2$;

N-(S)-2-Tetrahydrofuroyl-Gly-D2Nal-D4ClPhe-D3Pal-Ser-NMeTyr-DLys(N-epsilon-Nicotinyl) -Leu-DLys(N-epsilon-Isopropyl)-Pro-DAlaNH$_2$;

N-(S)-2-Tetrahydrofuroyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-(R,S)-2-Tetrahydrofuroyl-Gly-D2Nal-D4ClPhe-D3Pal-Ser-Tyr-DLys(N-epsilon-Nicotinyl) -Leu-Lys(N-epsilon-Isopropyl)-Pro-DAlaNH$_2$;

N-(S)-2-Tetrahydrofuroyl-Gly-D2Nal-D4ClPhe-D3Pal-Ser-NMeTyr-DHcit-Leu-Lys(N-epsilon-Isopropyl)-Pro-DAlaNH$_2$;

N-(S)-2-Tetrahydrofuroyl-Gly-D2Nal-D4ClPhe-D3Pal-Ser-Tyr-DHcit-Leu-Lys(N-epsilon-Isopropyl)-Pro-DAlaNH$_2$;

N-(S)-2-Tetrahydrofuroyl-Gly-D2Nal-DPhe-D3Pal-Ser-NMeTyr-DLys(Nic)-Leu-Lys(N-epsilon-Isopropyl)-Pro-DAlaNH$_2$;

N-(S)-2-Tetrahydrofuroyl-Gly-D2Nal-D4ClPhe-D3Pal-Ser-Tyr-DHcit-Leu-Arg-Pro-DAlaNH$_2$;

N-(S)-2-Tetrahydrofuroyl-Bala-D2Nal-D4ClPhe-D3Pal-Ser-NMeTyr-DLys(Nic)-Leu-Lys(Isp)-Pro-DAlaNH$_2$;

N-(S)-2-Tetrahydrofuroyl-Gaba-D2Nal-D4ClPhe-D3Pal-Ser-NMeTyr-DLys(Nic)-Leu-Lys(Isp)-Pro-DAlaNH$_2$;

N-(S)-2-Tetrahydrofuroyl-Aha-D2Nal-D4ClPhe-D3Pal-Ser-NMeTyr-DLys(Nic)-Leu-Lys(Isp)-Pro-DAlaNH$_2$;

N-(S)-2-Tetrahydrofuroyl-Sar-D2Nal-D4ClPhe-3DPal-Ser-NMeTyr-DLys(Nic)-Leu-Lys(Isp)-Pro-DAlaNH$_2$;

N-(S)-2-Tetrahydrofuroyl-Gly-DAla-D4ClPhe-D3Pal-Ser-NMeTyr-DLys(Nic)-Leu-Lys(Isp)-Pro-DAlaNH$_2$;

N-(S)-2-Tetrahydrofuroyl-Gly-Sar-D4ClPhe-D3Pal-Ser-NMeTyr-DLys(Nic)-Leu-Lys(Isp)-Pro-DAlaNH$_2$; and N-(S)-2-Tetrahydrofuroyl-Aca-D2Nal-D4ClPhe-D3Pal-Ser-NMeTyr-DLys(Nic)-Leu-Lys(Isp)-Pro-DAlaNH$_2$.

LHRH Antagonist Activity

Representative compounds of the present invention were evaluated in an in vitro test for LHRH antagonist potency (pA$_2$). The test employed the method detailed in F. Haviv, et al. *J. Med. Chem.*, 32:2340–2344 (1989). The values of pA$_2$ are the negative logarithms of the concentration of the particular antagonist test compound required to shift the response curve produced by the agonist leuprolide to two-fold higher concentration. (Leuprolide is the LHRH agonist having the structure 5-oxo-Pro[1] -His[2]-Trp[3]-Ser[4]-Tyr[5]-D-Leu[6]-Leu[7]-Arg[8]-Pro[9]-NHEt and is disclosed and claimed in U.S. Pat. No. 4,005,063.) Typically pA$_2$ values of 9.5 or greater are indicative of good LHRH antagonist potency, with values of 10.0 or greater being preferred.

The results of these tests for representative compounds in accordance with this invention are presented in Table 1.

TABLE 1

| Example No. | pA$_2$ |
|---|---|
| 1 | 10.75 |
| 2a | 10.55 |
| 2b | 10.3 |
| 2c | 11.1 |
| 2d | 10.9 |
| 2e | 10.7 |
| 2f | 11.05 |
| 2g | 11.15 |
| 2h | 11 |
| 3 | 10.8 |
| 4 | 11.1 |
| 5 | 10.67 |
| 6a | 11.05 |
| 6b | 10.8 |
| 6c | 10.65 |
| 6d | 10.9 |
| 6e | 11.02 |
| 6f | 10.59 |
| 7 | 10.58 |
| 8 | 10.69 |
| 9 | 10.46 |
| 10 | 10.41 |
| 11 | 10.42 |
| 12 | 10.36 |
| 13a | 11.35 |
| 13b | 11.02 |
| 13c | 11.45 |
| 13d | 10.39 |
| 13e | 10.5 |
| 13f | 10.75 |
| 14a | 10.88 |
| 14b | 9.98 |
| 14c | 11.27 |
| 14d | 11.05 |
| 14e | 10.71 |
| 14f | 10.45 |
| 14g | 9.96 |
| 14h | 11.38 |
| 14i | 9.47 |
| 14j | 9.12 |
| 14k | 11 |
| 14l | 10.7 |
| 14m | 10.75 |
| 14n | 11.17 |
| 15a | 10.2 |
| 15b | 10.68 |
| 15c | 11 |
| 15d | 10.75 |
| 16 | 10.54 |
| 17 | 10.95 |
| 18a | 10.78 |
| 18b | 11.04 |
| 19 | 10.39 |
| 20 | 10.58 |
| 21 | 10.5 |
| 22 | 11.47 |
| 23a | 10.71 |
| 23b | 10.73 |
| 24 | 10.55 |
| 25a | 10.85 |
| 25b | 11.1 |
| 25c | 11.77 |
| 25d | 10.47 |
| 25e | 11.47 |
| 25f | 10.63 |
| 25g | 10.49 |
| 26a | 10.56 |
| 26b | 10.36 |
| 26c | 11.62 |
| 27a | 11.11 |
| 27b | 10.87 |
| 27c | 10.01 |
| 27d | 11.75 |
| 27e | 10.46 |
| 28 | 11.01 |
| 29 | 10.59 |
| 30a | 10.32 |

TABLE 1-continued

| Example No. | pA$_2$ |
|---|---|
| 30b | 10.53 |
| 30c | 10.42 |
| 31 | 10.71 |
| 32 | 10.85 |
| 33a | 11.2 |
| 33b | 10.7 |
| 33c | 11.3 |
| 34 | 9.95 |
| 35a | 10 |
| 35b | 10.1 |
| 36 | 10.65 |
| 37a | 11.2 |
| 37b | 10.8 |
| 37c | 10.6 |
| 37d | 9.9 |
| 37e | 10.65 |
| 38 | 10.51 |
| 39 | 10.81 |
| 66 | 8.58 |
| 67 | 10.6 |
| 68 | 10.85 |
| 69 | 10.7 |
| 70 | 10.9 |
| 71 | 11.15 |
| 72a | 11 |
| 72b | 10.07 |
| 72c | 10.7 |
| 72d | 11.06 |
| 72e | 10.85 |
| 72f | 11 |
| 72g | 10.7 |
| 72h | 11.2 |
| 73 | 10.35 |
| 74 | 10.25 |
| 75 | 10.95 |
| 76 | 10.45 |
| 77 | 10.85 |
| 78a | 10.98 |
| 78b | 11.08 |
| 78c | 10.88 |
| 78d | 11.1 |
| 78e | 10.79 |
| 78f | 10.5 |
| 78g | 11.15 |
| 78h | 10.5 |
| 79 | 10.71 |
| 80 | 10.9 |
| 81 | 9.05 |
| 82 | 8.95 |
| 83 | 10.95 |
| 84 | 10.42 |
| 85 | 10.95 |
| 86 | 9.85 |
| 87 | 9.57 |
| 88 | 9.8 |
| 89 | 9.88 |
| 90 | 9.34 |
| 91 | 11.66 |
| 92 | 10.98 |
| 93 | 11.23 |
| 94 | 11.08 |
| 95 | 11.12 |
| 96 | 10.56 |
| 97 | 10.47 |
| 98 | 10.44 |
| 99 | 10.93 |
| 100 | 7.66 |
| 101 | 7.37 |
| 102 | 10.24 |

The compounds of the present invention to act as LHRH antagonism and are useful for suppressing levels of gonadotropins and androgens in mammals.

In the practice of the method of this invention an amount of a compound of the invention or a pharmaceutical composition containing the antagonists, effective to suppress levels of sex hormones in a mammal, is administered to the host in need of such treatment. These compounds or compositions may be administered by any of a variety of routes depending upon the specific end use, including orally, parenterally (including subcutaneous, intramuscular and intraveneous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 0.01 and 10 mg/kg body weight per day, preferably between about 0.1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intraveneous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Druq Delivery Systems, J. R. Robinson ed., Marcel Dekker, Inc., New York, 1978. Particular reference with respect to LHRH type compounds may be found, for example, in U.S. Pat. No. 4,010,125.

Synthesis of the Compounds of the Invention

In general, the compounds of the present invention are synthesized by techniques known to those skilled in the art as, for example, by so-called "solid phase" peptide synthesis or by usual methods of solution phase chemistry. A summary of available solid phase peptide synthetic techniques may be found in J. M. Stewart and J. D. Young, Solid Phase Peptide Synthesis, W. H. Freeman Co., San Francisco, 1963 and J. Meienhofer, Hormonal Proteins and Peptides, Vol. 2., p.46, Academic Press (New York), 1973. For classical solution synthesis see G. Schroder and K. Lupke, The Peptides, vol. 1, Academic Pres (New York), 1965.

In general, these methods comprise the sequential addition of one or more amino acids or suitably protected amino acids to a growing peptide chain bound to a suitable resin. The starting amino acids are commercially available or, where novel in the compounds of this invention, are synthesized by methods detailed below from readily available starting materials.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conducive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing peptides involves solid phase peptide synthesis. In this method of preparing peptides, the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha, alpha)-dimethyl-3,5dimethoxybenzyloxycarbonyl, o-nitrophenylsulfenyl, 2-cyano-t-butyloxycarbonyl, 9-fluorenylmethyloxycarbonyl and the like. The t-butyloxycarbonyl ("BOC" or "t-BOC") protecting group is preferred.

Particularly preferred side chain protecting groups are, for side-chain amino groups as in lysine and arginine: nitro, p-toluene-sulfonyl, 4-methoxybenzenesulfonyl, Cbz, BOC and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tetrahydropyranyl; for histidine: benzyl, Cbz, p-toluenesulfonyl and 2,4-dinitrophenyl; for tryptophan: formyl.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. Chloromethyl-polystyrene-1% divinylbenzene polymer is especially preferred. For the special case where the C-terminus of the compound is glycinamide, a particularly useful support is the benzhydrylamino-polystyrene-divinylbenzene polymer described by P. Rivaille, et al, *Helv. Chim. Acta.*, 54, 2772 (1971). The coupling to the chloromethyl polystyrene-divinylbenzene type of resin is made by means of the reaction of the alpha-N-protected amino acid, especially the BOC-amino acid, as its cesium, tetramethylammonium, triethylammonium, 1,5-diazabicyclo-[5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40° and 60° C., for from about 12 to 48 hours. Preferred reagents and reaction conditions involve the coupling of an alpha-N-BOC amino acid cesium salt with the resin in DMF at about 50° C. for about 24 hours. The alpha-N-BOC-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBt), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours, preferably about 12 hours at a temperature of between about 10° and 50° C., most preferably 25° C. in a solvent such as dichloromethane or DMF, preferably dichloromethane. The coupling of the carboxyl group to the N-methyl-Ser(OBzl) attached to the peptide resin requires catalysis by 4-dimethylaminopyridine (DMAP), in addition to the carbodiimide reagent.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBt, N-hydroxysuccinimide, other N-hydroxyimides or oximes. Alternately, protected amino acid active ester (e.g. p-nitrophenyl, pentafluorophenyl and the like) or symmetrical anhydrides may be used.

The side-chain modifications of the peptides of the present invention are carried out by methods detailed below in Preparations A–B.

PREPARATION A

N-(t-Butoxycarbonyl)-N-Methyl-(4-FMOC-aminomethyl)Phenylalanine

A mixture of N-trifluoroacetyl-N-methyl-phenylalanine (1 equivalent) and zinc chloride (0.9 to 2.2 equivalents) in chloromethylether is heated at 65° C. for 10–24 hr. The excess reagent is removed in vacuo and the residue is dissoved in $CH_2Cl_2$, washed with saturated $NaHCO_3$ solution, then with saturated sodium chloride solution. The organic phase is dried ($Na_2SO_4$) and concentrated. The crude product is purified by column chromatography to yield the 4-(chloromethyl)phenylalanine methyl ester. This is treated with aqueous hydrochloric acid to cleave the methyl ester. The N-methyl-(4-chloromethyl)phenylalanine hydrochloride is treated with di-t-butylcarbonate (1.2 equivalents) in the presence of triethylamine (1 equivalent) in THF at 0° C. for 1 hr. After work-up and purification BOC-N-methyl-(4-chloromethyl)phenylalanine is obtained.

BOC-N-Me-(4-chloromethyl)phenylalanine is heated under reflux for 4 to 24 hr with excess of sodium azide and catalytic amount of sodium iodide in methanol. The residue is treated with dilute hydrochloric acid to pH 6 and extracted with ethyl acetate. The organic extracts are dried and concentrated to yield BOC-N-methyl-(4-azidomethyl)phenylalanine. This is hydrogenated over Pd/C catalyst in methanol to afford BOC-N-methyl-(4-aminomethyl)phenylalanine. The last compound is treated with 9-fluorenylmethyl chlorocarbonate under basic conditions as described in page 24 of "The Practice of Peptide Synthesis" by M. Bodanszky and A. Bodanszky. After work-up and purification N-(t-butoxycarbonyl)-N-methyl-(4-FMOC-aminomethyl)phenylalanine is obtained (see Scheme 1).

SCHEME 1

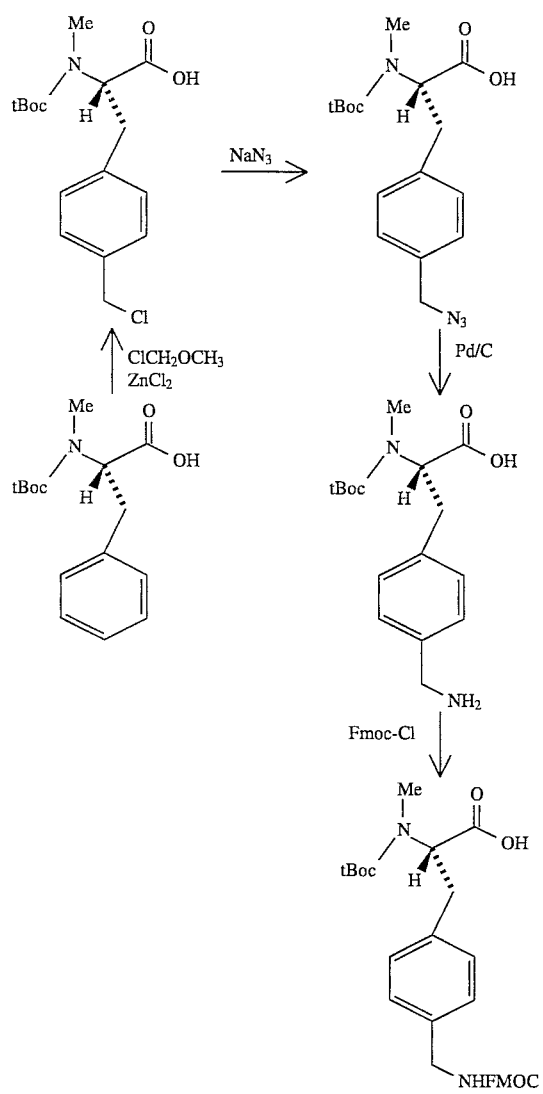

PREPARATION B

N-(t-Butoxycarbonyl)-D-(4-FMOC-aminomethyl) Phenylalanine

BOC-D-(4-chloromethyl)phenylalanine is synthesized according to Preparation A described above. The product is first treated with sodium azide in methanol, using analogous conditions to those previously described, and then hydrogenated to yield N-BOC-D-(4-aminomethyl)phenylalanine which is substituted with FMOC, as previously described, to afford N-(t-Butoxycarbonyl)-D-(4-FMOC-aminomethyl)Phenylalanine.

The Atz or 3-amino-1,2,4-triazol-5-yl group can be attached to the 4-amino group of 3-(4-aminophenyl)alanine or the terminal amino group the omega-aminoalkyl side chain of any alpha,omega-diaminocarboxylic acid amino acid by the method detailed below in Scheme 2 which illustrates the process for $N^\alpha$-methyl-3-(4-aminophenyl)alanine.

As shown in Scheme 2 below, upon the completion of the synthesis of a peptide-resin containing an $N^\alpha$-methyl-3-(4-aminophenyl)alanine residue, the peptide resin is treated with 30% piperidine/DMF for 2 to 24 hr, to cleave the FMOC group from the N-4-amino position of the N-Me-Phe residue. The peptide-resin is washed, 3 times with methylene chloride, 3 times with DMF, and reacted with 10-to 20-fold excess of diphenylcyanocarboimidate in DMF overnight (see Scheme 2 below), washed, 3 times with methylene chloride, 3 times with DMF, and then reacted with 20- to 100-fold excess of hydrazine in DMF overnight. The peptide-resin is washed, as previously described, dried over $P_2O_5$ overnight, and treated with HF/anisole as above.

SCHEME 2

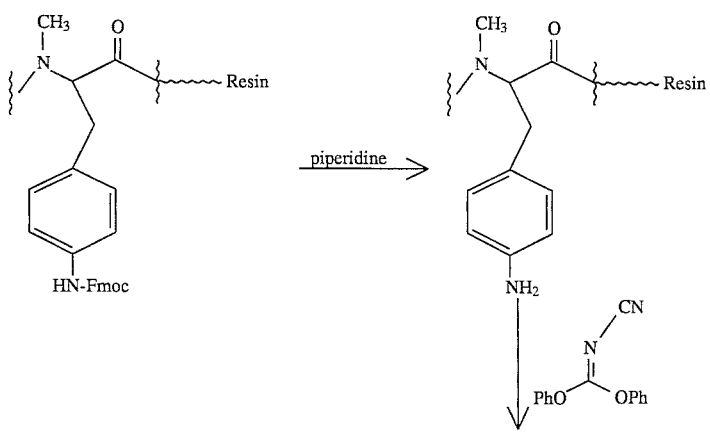

-continued
SCHEME 2

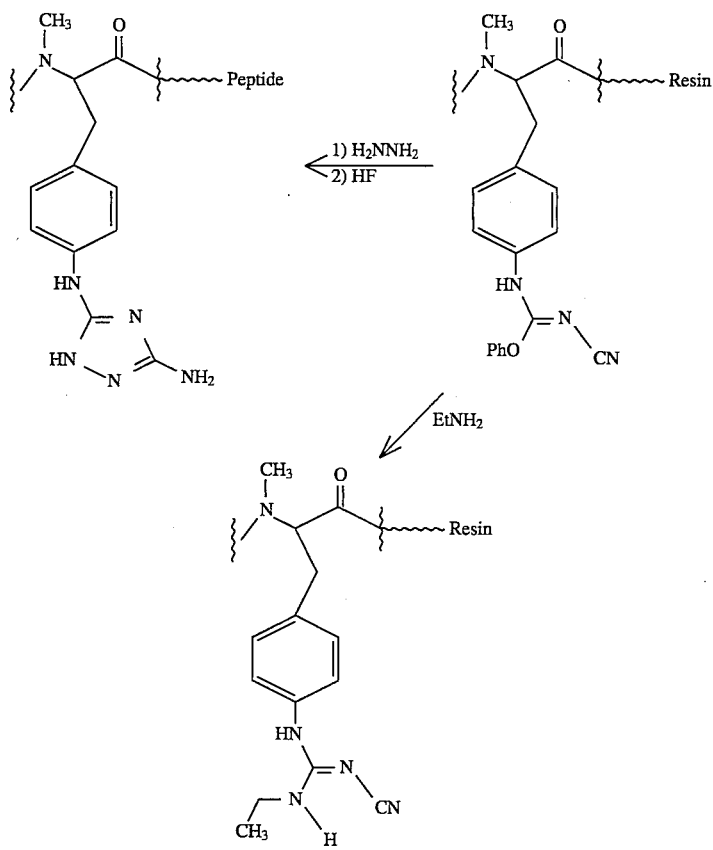

The process of Scheme 2 above is similarly used for the attachment of the Atz group to, for example, the epsilon-amino group in the side chain of lysine or similar aminoacyl residue having an omega-aminoalkyl side chain group.

EXAMPLE 1

N-Ac-DTyr-D2Nal-D4ClPhe-D3Pal-Ser-NMeTyr-DLys(Nicotinyl)-Leu-Lys(N-epsilon-Isopropyl)-Pro-DAlaNH$_2$ (Compound 1)

In the reaction vessel of a Milligen-Biosearch 9500 peptide synthesizer was placed 1 g (0.6 mmol) of-D-Ala-NH-resin (4-methyl-benzhydrylamine resin). Amino acids were added sequentially according to the following synthetic cycle:

1. Deblocking, to remove the t-BOC group from the alpha-amino function of the peptide, is carried out using a solution of 45% trifluoroacetic acid (TFA), 2.5% anisole, 2.0% dimethyl phosphite, and 50.5% methylene chloride. The resin is prewashed with the deblocking solution for one minute and then the deblocking reaction is run for 20 minutes.
2. Base wash, to remove and neutralize the TFA used for deprotection, is carried out using a solution of 10% N,N'-diisopropylethylamine in methylene chloride. The resin is washed with base three times for one minute each time after a deblocking step.
3. Coupling reaction is carried out using a 3-fold molar excess of 0.3M DMF solution of a t-BOC protected amino acid derivative along with a 3-fold molar excess of 0.3M methylene chloride solution of diisopropylcarbodiimide as activator. The activated amino acid is then coupled to the free alpha amino group of the peptide-resin. The reaction time is as described in the synthesis protocol.
4. Wash, each reaction step is followed by three washes of one minute each: one of methylene chloride, one of (1:1) methylene chloride/DMF, and one of DMF.

Synthesis Protocol:

The amino protected amino acids are coupled to the resin according the following order, number, and duration of couplings:

| # Amino Acid | Coupling |
|---|---|
| 1. BOC—Pro | two-1h |
| 2. BOC—Lys(N-epsilon-Cbz, Isopropyl) | two-1h |
| 3. BOC—Leu | two-1h |
| 4. BOC—D—Lys(N-epsilon-Nicotinyl) | two-1h |
| 5. BOC—NMe—Tyr(O-2,6-diCl—Bzl) | two-1h |
| 6. BOC—Ser(OBzl) | two-1h |
| 7. BOC—D-3Pal | two-6h |
| 8. BOC—D-4ClPhe | two-2h |
| 9. BOC—D2Nal | two-2h |
| 10. BOC—DTyr(O-2,6-diCl—Bzl) | two-2h |
| 11. acetic acid | two-2h |

Upon completion of the synthesis the resin is dried overnight over P$_2$O$_5$ under vacuum and then treated with dry HF in the presence of anisole at 0° C. for 1 h to cleave the peptide from the resin. The excess of reagent is removed in vacuo. The resin is washed first with ether, then stirred at room temperature with a solution of (1:1:0.1) water/acetonitrile/acetic acid (50 ml) for 15 minutes, and filtered. The filtrate is lyophilized to give the crude peptide as a fluffy powder. This is purified by HPLC using a (25×2.5 cm) Dynamax C-18 column (8 micron) with solvent mixtures varying in a gradient ranging from 89% $H_2O$/11% $CH_3CN$/ 0.1% TFA over a period of 20 minutes. The UV detector is set at 260 nm. The product is eluted at 37.80 min as a single peak, collected and lyophilized to give pure NAc-DTyr-D2Nal-D4ClPhe-D 3Pal-Ser-NMeTyr-DLys(N-epsilon-Nicotinyl)-Leu-Lys(N-epsilon-Isopropyl)-Pro-DAlaNH$_2$ (1) as the trifluoroacetate salt. FAB Mass spec. m/e 1697 (M+H)$^+$. Amino Acid Anal: 1.01 Ala; 0.99 Pro; 0.99 Lys; 1.01 Leu; 0.99 NMeTyr; 0.49Ser; 0.94 Tyr.

EXAMPLE 2

The following compounds were prepared by the procedure described in Example 1 was used but substituting BOC-Gly for BOC-DTyr(O-2,6-diCl-Bzl) and the appropriate carboxylic acids instead of acetic acid. After work-up, lyophilization, and HPLC purification the following compounds were obtained:

Example 2a N-Shikimyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 26); $R_t$=23.17 min; FAB Mass spec. m/e 1705 (M+H)$^+$. Amino Acid Analysis: 1.00 Ala; 1.01 Pro; 1.04 Lys(Isp); 1.00 Leu; 0.99 Lys; 0.78 NMeTyr; 0.54 Ser; 0.99 3Pal; 1.06 4ClPhe; 0.99 Gly.

Example 2b N-Dihydroshikimyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 27); $R_t$=17.45 min; FAB Mass spec. m/e 1707 (M+H)$^+$. Amino Acid Analysis: 1.03 Ala; 0.88 Pro; 0.96 Lys(Isp); 0.93 Leu; 0.98 Lys; 0.40 NMeTyr; 0.56 Ser; 0.80 3Pal; 0.97 4ClPhe; 1.22 Gly.

Example 2c N-2-Furoyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 28); $R_t$=28.57 min; FAB Mass spec. m/e 1643 (M+H)$^+$. Amino Acid Analysis: 1.05 Ala; 0.97 Pro; 0.95 Lys(Isp); 0.97 Leu; 1.00 Lys; 0.56 NMeTyr; 0.44 Ser; 0.74 3Pal; 0.91 4ClPhe; 1.02 Gly.

Example 2d N-3Furoyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 29); $R_t$=28.82 min; FAB Mass spec. m/e 1643 (M+H)$^+$. Amino Acid Analysis: 1.06 Ala; 1.00 Pro; 0.90 Lys(Isp); 1.00 Leu; 0.97 Lys; 0.60 NMeTyr; 0.46 Ser; 0.72 3Pal; 0.72 4ClPhe; 0.95 Gly.

Example 2e N-Picolyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 30); $R_t$=29.25 min; FAB Mass spec. m/e 1654 (M+H)$^+$. Amino Acid Analysis: 1.00 Ala; 1.04 Pro; 1.01 Lys(Isp); 1.01 Leu; 0.96 Lys; 1.03 NMeTyr; 0.50 Ser; 1.01 3Pal; 1.07 4ClPhe; 0.98 Gly.

Example 2f N-Nicotinyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 31); $R_t$=26.65 min; FAB Mass spec. m/e 1654 (M+H)$^+$. Amino Acid Analysis: 1.03 Ala; 1.01 Pro; 0.88 Lys(Isp); 1.01 Leu; 0.96 Lys; 0.99 NMeTyr; 0.45 Ser; 1.08 3Pal; 1.16 4ClPhe; 1.00 Gly.

Example 2g N-Isonicotinyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 32); $R_t$=22.77 min; FAB Mass spec. m/e 1654 (M+H)$^+$. Amino Acid Analysis: 1.00 Ala; 1.02 Pro; 0.97 Lys(Isp); 1.03 Leu; 0.97 Lys; 1.02 NMeTyr; 0.43 Ser; 1.01 3pal; 1.04 4ClPhe; 0.97 Gly.

Example 2h N-Salicyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 33); $R_t$=31.25 min; FAB Mass spec. m/e 1669 (M+H)$^+$. Amino Acid Analysis: 1.01 Ala; 1.02 Pro; 0.99 Lys(Isp); 1.02 Leu; 0.98 Lys; 1.10 NMeTyr; 0.47 Ser; 0.98 3Pal; 1.02 4ClPhe; 0.98 Gly.

EXAMPLE 3

N-(R,S)-Tetrahydrofur-2-oyl-Gly-D2Nal-D4ClPhe-D3Pal-Ser-NMeTyr-DLys(Nicotinyl) -Leu-Lys(N-epsilon-Isopropyl)-Pro-DAlaNH$_2$ (Compound 23)

The title compound was prepared by the procedure described in Example 1 was used but substituting BOC-Gly for BOC-DTyr(O-2,6-diCl-Bzl) and (R,S) tetrahydro-2-furoyl for acetic acid. After work-up, lyophilization, and HPLC purification N[(R,S) Tetrahydrofur-2-oyl]-D2Nal-D4ClPhe-D3Pal-Ser-NMeTyr-DLys(Nicotinyl)-Leu-Lys(N-epsilon-Isopropyl) -Pro-DAlaNH$_2$ (23) was obtained as trifluoroacetate salt; $R_t$=26.95min; FAB Mass spec. m/e 1647 (M+H)$^+$. Amino Acid Analysis: 1.00 Ala; 1.04 Pro; 0.94 Lys(Isp); 1.02 Leu; 0.96 Lys; 1.10 NMeTyr; 0.49 Ser; 1.00 3Pal; 1.07 4ClPhe; 0.98 Gly.

EXAMPLE 4

N-(S)-Tetrahydrofur-2-oyl-Gly-D2Nal-D4ClPhe-D3Pal-Ser-NMeTyr-DLys(Nicotinyl) -Leu-Lys(N-epsilon-Isopropyl)-Pro-DAlaNH$_2$ (Compound 24)

The title compound was prepared by the procedure described in Example 3 substituting (S)-tetrahydro-2-furoic acid for (R,S)-tetrahydro-2-furoic acid. After work-up, lyophilization, and HPLC purification N[(S) Tetrahydro-fur-2-oyl]-D2Nal-D 4ClPhe-D3Pal-Ser-NMeTyr-DLys(Nicotinyl)-Leu-Lys(N-epsilon-Isopropyl)-Pro-DAlaNH$_2$ (24) was obtained as trifluoroacetate salt; $R_t$=27.08 min; FAB Mass spec. m/e 1647 (M+H)$^+$. Amino Acid Analysis: 1.00 Ala; 0.99 Pro; 0.93 Lys(Isp); 0.99 Leu; 1.03 Lys; 0.90 NMeTyr; 0.55 Ser; 0.98 3Pal; 1.00 4ClPhe; 1.00 Gly.

EXAMPLE 5

N-(R) Tetrahydrofur-2-oyl-Gly-D2Nal-D4ClPhe-D3Pal-Ser-NMeTyr-DLys(Nicotinyl) -Leu-Lys(N-epsilon-Isopropyl)-Pro-DAlaNH$_2$ (Compound 25)

The title compound was prepared by the procedure described in Example 3 substituting (R)-tetrahydro-2-furoic acid for (R,S)-tetrahydro-2-furoic acid. After work-up, lyophilization, and HPLC purification N[(R) Tetrahydro-fur-2-oyl]-D2Nal-D 4ClPhe-D3Pal-Ser-NMeTyr-DLys(Nicotinyl)-Leu-Lys(N-epsilon-Isopropyl)-Pro-DAlaNH$_2$ (25) was obtained as trifluoroacetate salt; $R_t$=18.32 min; FAB Mass spec. m/e 1647 (M+H)$^+$. Amino Acid Analysis: 0.96 Ala;

0.98 Pro; 1.01 Lys(Isp); 0.99 Leu; 1.07 Lys; 0.93 NMeTyr; 0.67 Ser; 1.16 3Pal; 1.11 4ClPhe; 1.13 Gly.

EXAMPLE 6

The following compounds were prepared by the procedure described in Example 1 was used but substituting the appropriate BOC-amino acids for BOC-DTyr(O-2,6-diCl-Bzl) and the appropriate carboxylic acids instead of acetic acid. After work-up, lyophilization, and HPLC purification the following compounds were obtained:

Example 6a N-Nicotinyl-3Aminopropionyl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 35); R$_t$=22.32 min; FAB Mass spec. m/e 1668 (M+H)$^+$. Amino Acid Analysis: 0.99 Ala; 1.02 Pro; 0.92 Lys(Isp); 1.02 Leu; 0.95 Lys; 1.04 NMeTyr; 0.40 Ser; 1.00 3Pal; 1.05 4ClPhe.

Example 6b N-Shikimyl-3Aminopropionyl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 36); R$_t$=22.25 min; FAB Mass spec. m/e 1719 (M+H)$^+$. Amino Acid Analysis: 1.00 Ala; 1.00 Pro; 1.02 Lys(Isp); 1.00 Leu; 1.00 Lys; 0.71 NMeTyr; 0.50 Ser; 1.00 3Pal; 1.00 4ClPhe.

Example 6c N-Nicotinyl-4Aminobutyryl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 38); R$_t$=22.75 min; FAB Mass spec. m/e 1682 (M+H)$^+$. Amino Acid Analysis: 1.02 Ala; 1.00 Pro; 0.89 Lys(Isp); 1.03 Leu; 0.96 Lys; 0.89 NMeTyr; 0.44 Ser; 0.70 3Pal; 0.75 4ClPhe; 0.97 4-aminobutyric acid.

Example 6d N-Shikimyl-4-Aminobutyryl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 39); R$_t$=22.50 min; FAB Mass spec. m/e 1733 (M+H)$^+$. Amino Acid Analysis: 0.99 Ala; 0.99 Pro; 0.89 Lys(Isp); 1.05 Leu; 0.97 Lys; 0.83 NMeTyr; 0.44 Ser; 0.71 3Pal; 0.76 D4ClPhe; 0.95 4-aminobutyric acid.

Example 6e N-Nicotinyl-5Aminovaleryl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 41); R$_t$=14.02 min; FAB Mass spec. m/e 1695 (M+H)$^+$. Amino Acid Analysis: 1.03 Ala; 1.00 Pro; 0.93 Lys(Isp); 1.00 Leu; 0.96 Lys; 0.94 NMeTyr; 0.43 Ser; 0.99 3Pal; 1.06 4ClPhe; 0.76 5-aminovaleric acid.

Example 6f N-Shikimyl-5Aminovaleryl-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 42); R$_t$=13.82 min; FAB Mass spec. m/e 1747 (M+H)$^+$. Amino Acid Analysis: 1.03 Ala; 1.01 Pro; 0.93 Lys(Isp); 1.00 Leu; 0.96 Lys; 1.01 NMeTyr; 0.45 Ser; 1.01 3Pal; 1.07 4ClPhe; 0.80 5-aminovaleric acid.

EXAMPLE 7

N-Shikimyl-DSer-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 47)

The title compound was prepared by the procedure described in Example 1 was used but substituting BOC-D-Ser(OBzl) for BOC-DTyr(O-2,6-diCl-Bzl) and shikimic acid for acetic acid. After workup, lyophilization, and HPLC purification there was obtained:

N-Shikimyl-DSer-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (47); R$_t$=13.73 min; FAB Mass spec. m/e 1735 (M+H)$^+$. Amino Acid Analysis: 1.03 Ala; 0.99 Pro; 0.97 Lys(Isp); 0.98 Leu; 0.99 Lys; 0.82 NMeTyr; 0.97 Ser; 1.01 3Pal; 1.05 4ClPhe.

EXAMPLE 8

N-Nicotinyl-Gly-D2Nal-D4ClPhe-D3Pal-Ser-NMeTyr-DLys(Gly-Nicotinyl)-Leu-Lys (N-epsilon-Isopropyl)-Pro-DAlaNH$_2$ (Compound 49)

The title compound was prepared by the procedure described in Example 2 for the synthesis of NicGly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ was used but substituting BOC-DLys(N-epsilon-FMOC) instead of BOC-DLys(N-epsilon-Nicotinyl). Upon the completion of the synthesis the peptide resin was treated with 20% piperidine/DMF overnight, washed three times with methylene chloride/DMF and then coupled first with BOC-Gly and second with nicotinic acid using two-two hr coupling protocol described in Example 1. The peptide resin was dried and treated with HF/anisole as previously described. After workup, lyophilization and HPLC purification N-Nicotinyl-Gly-D2Nal-D4ClPhe-D3Pal-Ser-NMeTyr-DLys(Gly-Nicotinyl) -Leu-Lys(N-epsilon-Isopropyl)-Pro-DAlaNH$_2$ (49) was obtained; R$_t$=13.88 min; FAB Mass spec. m/e 1711 (M+H)$^+$. Amino Acid Analysis: 1.01 Ala; 0.98 Pro; 0.92 Lys(Isp); 0.98 Leu; 0.97 Lys; 0.65 NMeTyr; 0.45 Ser; 0.92 3Pal; 0.98 4ClPhe; 2.06 Gly.

EXAMPLE 9

N-Nicotinyl-Gly-D2Nal-D4ClPhe-D3Pal-Ser-NMeTyr-DLys(Azagly-Nicotinyl)-Leu-Lys(N-epsilon-Isopropyl) -Pro-DAlaNH$_2$ (Compound 50)

The title compound was prepared by the procedure described in Example 2 for the synthesis of NicGly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ was used but substituting BOC-DLys(N-epsilon-FMOC) instead of BOC-DLys(N-epsilon-Nicotinyl). Upon the completion of the synthesis the peptide resin was treated with 20% piperidine/DMF overnight, washed three times with methylene chloride/DMF and then treated with a large excess of carbonyldiimidazole in DMF for 30 minutes. The peptide resin was washed three times with a 1:1 mixture of DMF/DCM and then reacted with a large excess of nicotinyl hydrazide in DMF overnight. The peptide resin was dried and treated with HF/anisole as previously described. After workup, lyophilization and HPLC purification N-Nicotinyl-Gly-D2Nal-D4ClPhe-D3Pal-Ser-NMeTyr-DLys(Azagly-Nicotinyl) -Leu-Lys(N-epsilon-Isopropyl)-Pro-DAlaNH$_2$ (50) was obtained; R$_t$=14.05 min; FAB Mass spec. m/e 1712 (M+H)$^+$. Amino Acid Analysis: 1.00 Ala; 1.03 Pro; 0.92 Lys(Isp); 1.00 Leu; 0.96 Lys; 1.00 NMeTyr; 0.45 Ser; 0.99 3Pal; 1.03 4ClPhe; 1.01 Gly.

EXAMPLE 10

N-Nicotinyl-Gly-D2Nal-D4ClPhe-D3Pal-Ser-NMeTyr-DLys(Azagly-2Furoyl)-Leu-Lys(N-epsilon-Isopropyl) -Pro-DAlaNH$_2$ (Compound 51)

The title compound was prepared by the procedure described in Example 9 was used but substituting 2-furoyl hydrazide instead of nicotinyl hydrazide. After workup, lyophilization and HPLC purification N-Nicotinyl-Gly-D2Nal-D4ClPhe-D 3Pal-Ser-NMeTyr-DLys(Azagly-2Furoyl)-Leu-Lys(N-epsilon-Isopropyl)-Pro-DAlaNH$_2$ (51) was obtained; R$_t$=16.35 min; FAB Mass spec. m/e 1700 (M+H)$^+$. Amino Acid Analysis: 1.01 Ala; 1.00 Pro; 0.95Lys(Isp); 1.00 Leu; 0.95 Lys; 0.87 NMeTyr; 0.48 Ser; 0.97 3Pal; 1.02 4ClPhe; 1.03 Gly.

EXAMPLE 11

N-(R,S)Tetrahydrofur-2-oyl-Gly-D2Nal-D4ClPhe-D3Pal-Ser-NMeTyr-DLys(Azagly-Nicotinyl)-Leu-Lys(N-epsilon-Isopropyl)-Pro-DAlaNH$_2$ (Compound 52)

The title compound was prepared by the procedures described in Examples 3 and 9 but substituting the approriate amino acids and N-terminal acids. After workup, lyophilization and HPLC purification N-(R,S)tetrahydrofur-2-oyl-Gly-D2Nal-D 4ClPhe-D3Pal-Ser-NMeTyr-DLys(Azagly-Nicotinyl)-Leu-Lys(N-epsilon-Isopropyl)-Pro-DAlaNH$_2$ (52) was obtained; R$_t$=23.23 min; FAB Mass spec. m/e 1706 (M+H)$^+$. Amino Acid Analysis: 1.00 Ala; 0.98 Pro; 1.02 Lys(Isp); 0.98 Leu; 1.05 Lys; 0.97 NMeTyr; 0.53 Ser; 0.95 3Pal; 1.01 4ClPhe; 1.01 Gly.

EXAMPLE 12

N-(R,S)Tetrahydrofur-2-oyl-D2Nal-D4ClPhe-D3Pal-Ser-NMeTyr-DLys(Gly-Nicotinyl)-Leu-Lys(N-epsilon-Isopropyl)-Pro-DAlaNH$_2$ (Compound 53)

The title compound was prepared by the procedure described in Example 3 was used but coupling with (R,S) tetrahydro2-furoic acid after BOC-D2Nal. After workup, lyophilization and HPLC purification N-(R,S)tetrahydrofur-2-oyl-D2Nal-D 4ClPhe-D3Pal-Ser-NMeTyr-DLys(Gly-Nicotinyl)-Leu-Lys(N-epsilon-Isopropyl)-Pro-DAlaNH$_2$ (53) was obtained; R$_t$=26.70 and 26.77 min; FAB Mass spec. m/e 1704 (M+H)$^+$. Amino Acid Analysis: 1.04 Ala; 0.97 Pro; 0.93 Lys(Isp); 0.99 Leu; 0.95 Lys; 0.86 NMeTyr; 0.50 Ser; 1.05 3Pal; 1.11 4ClPhe; 2.02 Gly.

EXAMPLE 13

The following compounds were prepared by the procedure described in Example 1 was used but substituting BOC-Gly for BOC-DTyr(O-2,6diCl-Bzl), BOC-DCit for BOC-DLys(N-epsilon-FMOC), BOC-Arg(Tos) for BOC-Lys(N-epsilon-CBZ,isopropyl) and the appropriate BOC-amino acids and acids for acetic acid. After workup, lyophilization and HPLC purification the following compounds were obtained:

Example 13a N-(R,S)-Tetrahydro-Fur-2-oyl-Gly-D2Nal-D4ClPhe-D3Pal-Ser-NMeTyr-DCit-Leu-Arg-Pro-DAlaNH$_2$ (Compound 80) was obtained as the trifluoroacetate salt; R$_t$=36.10 min; FAB Mass spec. m/e 1557 (M+H)$^+$. Amino Acid Analysis: 1.01 Ala; 0.99 Pro; 0.99 Arg; 1.02 Leu; 1.03 Cit; 0.49 Ser; 1.05 Pal; 1.06 4ClPhe; 0.98 Gly.

Example 13b N-Shikimyl-Gly-D2Nal-D4ClPhe-D3Pal-Ser-NMeTyr-DCit-Leu-Arg-Pro-DAlaNH$_2$ (Compound 81) was obtained as the trifluoroacetate salt; R$_t$=32.35 min; FAB Mass spec. m/e 1615 (M+H)$^+$. Amino Acid Analysis: 1.01 Ala; 1.03 Pro; 0.96 Arg; 1.04 Leu; 0.98 Cit; 0.47 Ser; 0.69 3Pal; 0.97 4ClPhe; 0.95 Gly.

Example 13c N-Nicotinyl-Gly-D2Nal-D4ClPhe-D3Pal-Ser-NMeTyr-DCit-Leu-Arg-Pro-DAlaNH$_2$ (Compound 82) was obtained as the trifluoroacetate salt; R$_t$=32.20 min; FAB Mass spec. m/e 1565 (M+H)$^+$. Amino Acid Analysis: 1.00 Ala; 1.01 Pro; 1.00 Arg; 1.03 Leu; 1.02 Cit; 0.86 NMeTyr; 0.44 Ser; 1.03 3Pal; 1.01 4ClPhe; 0.95 Gly.

Example 13d N-Succinyl-Gly-D2Nal-D4ClPhe-D3Pal-Ser-NMeTyr-DCit-Leu-Arg-Pro-DAlaNH$_2$ (Compound 83) was obtained as the trifluoroacetate salt; R$_t$=38.05 min; FAB Mass spec. m/e 1559 (M+H)$^+$. Amino Acid Analysis: 1.01 Ala; 1.00 Pro; 0.96 Arg; 0.99 Leu; 1.00 Cit; 1.04 NMeTyr; 0.53 Ser; 0.97 3Pal; 1.04 4ClPhe; 1.05 Gly.

Example 13e N-Shikimyl-DAla-D2Nal-D4ClPhe-D3Pal-Ser-NMeTyr-DCit-Leu-Arg-Pro-DAlaNH$_2$ (Compound 848 4) was obtained as the trifluoroacetate salt; R$_t$=31.25 min; FAB Mass spec. m/e 1629 (M+H)$^+$. Amino Acid Analysis: 1.99 Ala; 1.03 Pro; 0.94 Arg; 1.03 Leu; 1.04 Cit; 1.05 NMeTyr; 0.51 Ser; 0.70 3Pal; 0.88 4ClPhe.

Example 13f N-Shikimyl-DSer-D2Nal-D4ClPhe-D3Pal-Ser-NMeTyr-DCit-Leu-Arg-Pro-DAlaNH$_2$ (Compound 85) was obtained as the trifluoroacetate salt; R$_t$=31.25 min; FAB Mass spec. m/e 1646 (M+H)$^+$. Amino Acid Analysis: 1.00 Ala; 1.04 Pro; 0.97 Arg; 1.00 Leu; 0.98 Cit; 0.90 NMeTyr; 1.02 Ser; 0.99 3Pal; 1.02 4ClPhe.

EXAMPLE 14

The following compounds were prepared by the procedure described in Example 1 was used but substituting BOC-Gly for BOC-D-Tyr(O-2,6-diCl-Bzl), BOC-Cit for BOC-DLys(N-epsilon-FMOC), BOC-Arg(Tos) for BOC-Lys(N-epsilon-Cbz,isopropyl), and the appropriate acids. After workup, lyophilization and HPLC purification the following compounds were obtained:

Example 14a N-Nicotinyl-Sar-D2Nal-D4ClPhe-D3Pal-Ser-NMeTyr-DLys(Shik)-Leu-Arg-Pro-DAlaNH$_2$ (Compoound 86) was obtained as the trifluoroacetate salt; R$_t$=31.35 min; FAB Mass spec. m/e 1705 (M+H)$^+$. Amino Acid Analysis: 1.00 Ala; 1.02 Pro; 1.01 Arg; 1.04 Leu; 0.93 Lys; 1.19 NMeTyr; 0.48 Ser; 1.14 3Pal; 1.23 4ClPhe; 0.97 Sar.

Example 14b N-Shikimyl-Sar-D2Nal-D4ClPhe-D3Pal-Ser-NMeTyr-DLys(Shik)-Leu-Arg-Pro-DAlaNH$_2$ (Compound 87) was obtained as the trifluoroacetate salt; R$_t$=31.35 min; FAB Mass spec. m/e 1757 (M+H)$^+$. Amino Acid Analysis: 0.99 Ala; 1.02 Pro; 0.99 Arg; 1.03 Leu; 0.97 Lys; 0.97 NMeTyr; 0.51 Ser; 1.12 3Pal; 1.2 4ClPhe; 0.90 Sar.

Example 14c N-Nicotinyl-DAla-D2Nal-D4ClPhe-D3Pal-Ser-NMeTyr-DLys(Shik)-Leu-Arg-Pro-DAlaNH$_2$ (Compound 88) was obtained as the trifluoroacetate salt; R$_t$=31.15 min; FAB Mass spec. m/e 1705 (M+H)$^+$. Amino Acid Analysis: 1.98 Ala; 1.02 Pro; 0.98 Arg; 1.02 Leu; 0.92 Lys; 1.10 NMeTyr; 0.47 Ser; 1.12 3Pal; 1.20 4ClPhe.

Example 14d N-Shikimyl-DAla-D2Nal-D4ClPhe-D3Pal-Ser-NMeTyr-DLys(Shik)-Leu-Arg-Pro-DAlaNH$_2$ (Compound 89) was obtained as the trifluoroacetate salt; R$_t$=30.75 min; FAB Mass spec. m/e 1756 (M+H)$^+$. Amino Acid Analysis: 1.98 Ala; 1.05 Pro; 1.00 Arg; 1.03 Leu; 0.94 Lys; 1.01 NMeTyr; 0.47 Ser; 1.11 3Pal; 1.19 4ClPhe.

Example 14e N-Nicotinyl-DSer-D2Nal-D4ClPhe-D3Pal-Ser-NMeTyr-DLys(Shik)-Leu-Arg-Pro-DAlaNH$_2$ (Compound 90) was obtained as the trifluoroacetate salt; R$_t$=31.35 min; FAB Mass spec. m/e 1722 (M+H)$^+$. Amino Acid Analysis: 0.97 Ala; 1.03 Pro; 0.96 Arg; 1.02 Leu; 0.96 Lys; 1.02 NMeTyr; 1.01 Ser; 1.10 3Pal; 1.14 4ClPhe.

Example 14f N-Shikimyl-DSer-D2Nal-D4ClPhe-D3Pal-Ser-NMeTyr-DLys(Shik)-Leu-Arg-Pro-DAlaNH$_2$ (Compound 91) was obtained as the trifluoroacetate salt; R$_t$=30.60 min; FAB Mass spec. m/e 1773 (M+H)$^+$. Amino Acid Analysis: 0.98 Ala; 1.03 Pro; 0.95 Arg; 0.99 Leu; 0.93 Lys; 1.02 NMeTyr; 0.96 Ser; 1.06 3Pal; 1.12 4ClPhe.

Example 14g N-Nicotinyl-DLys(Nic)-D2Nal-D4ClPhe-D3Pal-Ser-NMeTyr-DLys(Shik)-Leu-Arg-Pro-DAlaNH$_2$ (Compound 92) was obtained as the trifluoroacetate salt; R$_t$=29.25 min; FAB Mass spec. m/e 1867 (M+H)$^+$. Amino Acid Analysis: 0.99 Ala; 1.01 Pro; 0.97 Arg; 1.03 Leu; 1.85 Lys; 1.05 NMeTyr; 0.49 Ser; 1.13 D3Pal; 1.20 D-4ClPhe.

Example 14h N-Shikimyl-DLys(Nic)-D2Nal-D4ClPhe-D3Pal-Ser-NMeTyr-DLys(Shik)-Leu-Arg-Pro-DAlaNH$_2$ (Compound 93) was obtained as the trifluoroacetate salt; R$_t$=28.65 min; FAB Mass spec. m/e 1918 (M+H)$^+$. Amino Acid Analysis: 0.98 Ala; 1.00 Pro; 0.99 Arg; 1.02 Leu; 1.79 Lys; 1.09 NMeTyr; 0.45 Ser; 1.11 3Pal; 1.19 4ClPhe.

Example 14i N-Nicotinyl-DLys(Shik)-D2Nal-D4ClPhe-D3Pal-Ser-NMeTyr-DLys(Shik)-Leu-Arg-Pro-DAlaNH$_2$ (Compound 94) was obtained as the trifluoroacetate salt; R$_t$=29.05 min; FAB Mass spec. m/e 1918 (M+H)$^+$. Amino Acid Analysis: 1.03 Ala; 1.04 Pro; 1.01 Arg; 1.06 Leu; 1.88 Lys; 1.12 NMeTyr; 0.57 Ser; 1.16 3Pal; 1.23 4ClPhe.

Example 14j N-Shikimyl-DLys(Shik)-D2Nal-D4ClPhe-D3Pal-Ser-NMeTyr-DLys(Shik)-Leu-Arg-Pro-DAlaNH$_2$ (Compound 95) was obtained as the trifluoroacetate salt; R$_t$=28.35 min; FAB Mass spec. m/e 1969 (M+H)$^+$. Amino Acid Analysis: 0.99 Ala; 1.02 Pro; 0.96 Arg; 1.02 Leu; 1.80 Lys; 1.01 NMeTyr; 0.49 Ser; 1.12 3Pal; 1.19 4ClPhe.

Example 14k N-Nicotinyl-Gly-D2Nal-D4ClPhe-D3Pal-Ser-NMeTyr-DLys(Shik)-Leu-Arg-Pro-DAlaNH$_2$ (Compound 96) was obtained as the trifluoroacetate salt; R$_t$=30.85 min; FAB Mass spec. m/e 1691 (M+H)$^+$. Amino Acid Analysis: 0.98 Ala; 1.04 Pro; 1.00 Arg; 1.02 Leu; 0.95 Lys; 0.92 NMeTyr; 0.47 Ser; 1.03 3Pal; 1.08 4ClPhe; 0.84 Gly.

Example 14l N-Shikimyl-Gly-D2Nal-D4ClPhe-D3Pal-Ser-NMeTyr-DLys(Shik)-Leu-Arg-Pro-DAlaNH$_2$ (Compound 97) was obtained as the trifluoroacetate salt; R$_t$=30.85 min; FAB Mass spec. m/e 1743 (M+H)$^+$. Amino Acid Analysis: 0.99 Ala; 1.06 Pro; 1.00 Arg; 1.03 Leu; 0.97 Lys; 0.92 NMeTyr; 0.49 Ser; 1.05 3Pal; 1.10 4ClPhe; 0.92 Gly.

Example 14m N-(S)-Tetrahydrofur-2-oyl-Gly-D2Nal-D4ClPhe-D3Pal-Ser-NMeTyr-DLys(Shik)-Leu-Arg-Pro-DAlaNH$_2$ (Compound 98) was obtained as the trifluoroacetate salt; R$_t$=38.40 min; FAB Mass spec. m/e 1683 (M+H)$^+$. Amino Acid Analysis: 1.01 Ala; 1.02 Pro; 0.98 Arg; 1.01 Leu; 0.96 Lys; 1.02 NMeTyr; 0.52 Ser; 1.003Pal; 1.09 4ClPhe; 1.02 Gly.

Example 14n N-(R)-Tetrahydrofur-2-oyl-Gly-D2Nal-D4ClPhe-D3Pal-Ser-NMeTyr-DLys(Shik)-Leu-Arg-Pro-DAlaNH$_2$ (Compound 99) was obtained as the trifluoroacetate salt; R$_t$=41.15 min; FAB Mass spec. m/e 1683 (M+H)$^+$. Amino Acid Analysis: 1.01 Ala; 1.02 Pro; 0.98 Arg; 1.01 Leu; 0.96 Lys; 1.02 NMeTyr; 0.52 Ser; 1.00 3Pal; 1.09 4ClPhe; 1.02 Gly.

EXAMPLE 15

The following compounds were prepared by the procedure described in Example 14 was used but substituting the appropriate BOC-amino acids at position G and acids at position X for BOC-DLys(Shik). After workup, lyophilization and HPLC purification the following compounds were obtained:

Example 15a N-Shikimyl-Gly-D2Nal-D4ClPhe-D3Pal-Ser-NMeTyr-DLys(Nic)-Leu-Arg-Pro-DAlaNH$_2$ (Compound 100) was obtained as the trifluoroacetate salt; R$_t$=32.85 min; FAB Mass spec. m/e 1692 (M+H)$^+$. Amino Acid Analysis: 1.00 Ala; 1.03 Pro; 0.97 Arg; 1.03 Leu; 1.00 Lys; 1.14 NMeTyr; 0.52 Ser; 1.12 3Pal; 0.97 Gly.

Example 15b N-Shikimyl-Gly-D2Nal-D4ClPhe-D3Pal-Ser-NMeTyr-DLys(Gly-Nic)-Leu-Arg-Pro-DAlaNH$_2$ (Compound 101) was obtained as the trifluoroacetate salt; R$_t$=34.75 min; FAB Mass spec. m/e 1750 (M+H)$^+$. Amino Acid Analysis: 1.01 Ala; 1.03 Pro; 0.98 Arg; 1.01 Leu; 0.97 Lys; 1.04 NMeTyr; 0.53 Ser; 1.00 3Pal; 1.09 4ClPhe; 2.01 Gly.

Example 15c N-Shikimyl-Gly-D2Nal-D4ClPhe-D3Pal-Ser-NMeTyr-DLys(DSer-Nic)-Leu-Arg-Pro-DAlaNH$_2$ (Compound 102) was obtained as the trifluoroacetate salt; R$_t$=34.45 min; FAB Mass spec. m/e 1778 (M+H)$^+$. Amino Acid Analysis: 1.04 Ala; 1.00 Pro; 0.94 Arg; 1.00 Leu; 1.02 Lys; 1.12 NMeTyr; 1.28 Ser; 1.02 3Pal; 1.06 4ClPhe; 1.15 Gly.

Example 15d N-Shikimyl-Gly-D2Nal-D4ClPhe-D3Pal-Ser-NMeTyr-DLys(Gly-Shik)-Leu-Arg-Pro-DAlaNH$_2$ (Compound 103) was obtained as the trifluoroacetate salt; R$_t$=18.59 min; FAB Mass spec. m/e 1799 (M+H)$^+$. Amino Acid Analysis: 1.13 Ala; 0.98 Pro; 0.99 Arg; 1.03 Leu; 0.96 Lys; 0.85 NMeTyr; 0.44 Ser; 0.69 3Pal; 0.76 4ClPhe; 1.91 Gly.

EXAMPLE 16

N-Shikimyl-Gly-D2Nal-D4ClPhe-D 1Nal-Ser-NMeTyr-DLys(Shik)-Leu-Arg-Pro-DAlaNH$_2$ (Compound 104)

The title compound was prepared by the procedure described in Example 14 for N-Shikimyl-Gly-D2Nal-D4ClPhe-D3Pal-Ser-NMeTyr-DLys(Shik)-Leu-Arg-Pro-DAlaNH$_2$ was used but substituting BOC-D1Nal for BOC-D3Pal. After workup, lyophilization and HPLC purification N-Shikimyl-Gly-D2Nal-D4ClPhe-D1Nal-Ser-NMeTyr-DLys(Shik)-Leu-Arg-Pro-DAlaNH$_2$; R$_t$=40.55 min; FAB Mass spec. m/e 1791 (M+H)$^+$. Amino Acid Analysis: 1.04 Ala; 1.00 Pro; 0.94 Arg; 0.99 Leu; 0.99 Lys; 0.61 NMeTyr; 0.58 Ser; 1.06 4ClPhe; 1.02 Gly.

EXAMPLE 17

N-Shikimyl-Gly-D2Nal-D4ClPhe-D3Pal-Ser-NMePhe-DLys(Shik)-Leu-Arg-Pro-DAlaNH$_2$ (Compound 105)

The title compound was prepared by the procedure described in Example 14 for N-Shikimyl-Gly-D2Nal-D4ClPhe-D3Pal-Ser-NMeTyr-DLys(Shik)-Leu-Arg-Pro-DAlaNH$_2$ was used but substituting BOC-NMePhe for BOC-NMeTyr(O-2,6diClBzl). After workup, lyophilization and HPLC purification N-Shikimyl-Gly-D 2Nal-D4ClPhe-D1Nal-Ser-NMePhe-DLys(Shik)-Leu-Arg-Pro-DAlaNH$_2$; R$_t$=35.05 min; FAB Mass spec. m/e 1726 (M+H)$^+$. Amino Acid Analysis: 1.03 Ala; 1.02 Pro; 0.98 Arg; 1.00 Leu; 0.52 Ser; 1.03Pal; 1.07 4ClPhe; 0.97 Gly.

EXAMPLE 18

The following compounds were prepared by the procedure described in Example 14 for N-Shikimyl-Gly-D2Nal-D4ClPhe-D3Pal-Ser-NMeTyr-DLys(Shik)-Leu-Arg-Pro-DAlaNH$_2$ was used but substituting BOC-Ile and BOC- NMeLeu, respectively, for BOC-Leu. After workup, lyophilization and HPLC purification the following compounds were obtained:

Example 18a N-Shikimyl-Gly-D2Nal-D4ClPhe-D3Pal-Ser-NMeTyr-DLys(Shik)-Ile-Arg-Pro-DAlaNH$_2$; R$_t$=32.05 min; FAB Mass spec. m/e 1742 (M+H)$^+$. Amino Acid Analysis: 1.06 Ala; 1.07 Pro; 0.99 Arg; 0.93 Ile; 0.52 Ser; 1.06 3Pal; 1.06 4ClPhe; 1.00 Gly (Compound 106).

Example 18b N-Shikimyl-Gly-D2Nal-D4ClPhe-D3Pal-Ser-NMeTyr-DLys(Shik)-NMeLeu-Arg-Pro-DAlaNH$_2$; R$_t$=33.4 min; FAB Mass spec. m/e 1756 (M+H)$^+$. Amino Acid Analysis: 1.09 Ala; 1.02 Pro; 0.97 Arg; 0.94 Lys; 0.75 NMeTyr; 0.51 Ser; 1.03 3Pal; 1.09 4ClPhe; 0.97 Gly (Compound 107).

EXAMPLE 19

N-Shikimyl-Gly-D2Nal-D4ClPhe-D3Pal-Ser-NMeTyr-DLys(Shik)-Leu-Arg-Aze-DAlaNH$_2$ (Compound 108)

The title compound was prepared by the procedure described in Example 14 for N-Shikimyl-Gly-D2Nal-D4ClPhe-D3Pal-Ser-NMeTyr-DLys(Shik)-Leu-Arg-Pro-DAlaNH$_2$ was used but substituting BOC-Aze for BOC-Pro. After workup, lyophilization and HPLC purification N-Shikimyl-Gly-D2Nal-D4ClPhe-D3Pal-Ser-NMeTyr-DLys(Shik)-Leu-Arg-Aze-DAlaNH$_2$ was obtained; R$_t$=14.13 min; FAB Mass spec. m/e 1728 (M+H)$^+$. Amino Acid Analysis: 1.03 Ala; 0.96 Arg; 0.98 Leu; 0.99 Lys; 1.41 NMeTyr; 0.51 Ser; 0.95 3Pal; 1.00 4ClPhe; 1.05 Gly.

EXAMPLE 20

N-Shikimyl-Gly-D2Nal-D4ClPhe-D3Pal-Ser-NMeTyr-DLys(GlyGlyNic)-Leu-Arg-Pro-DAlaNH$_2$ (Compound 109)

The title compound was prepared by the procedure described in Example 15 for N-Shikimyl-Gly-D2Nal-D4ClPhe-D3Pal-Ser-NMeTyr-DLys(Gly-Nic)-Leu-Arg-Pro-DAlaNH$_2$ was used but coupling twice with BOC-Gly before the nicotinic acid coupling. After workup, lyophilization and HPLC purification N-Shikimyl-Gly-D 2Nal-D4ClPhe-D3Pal-Ser-NMeTyr-DLys(GlyGlyNic)-Leu-Arg-Pro-DAlaNH$_2$ was obtained; R$_t$=14.77 min; FAB Mass spec. m/e 1805 (M+H)$^+$. Amino Acid Analysis: 1.02 Ala; 1.00 Arg; 1.03 Leu; 1.02Lys; 1.10 NMeTyr; 0.47 Ser; 1.17 3Pal; 0.91 4ClPhe; 2.90 Gly.

EXAMPLE 21

N-(L-Gulonyl)-Gly-D2Nal-D4ClPhe-D3Pal-Ser-NMeTyr-DLys(Gly-L-Gulonyl)-Leu-Arg-Pro-DAlaNH$_2$ (Compound 110)

The title compound was prepared by the procedure described in Example 15 for N-Shikimyl-Gly-D2Nal-D4ClPhe-D3Pal-Ser-NMeTyr-DLys(Gly-Shik)-Leu-Arg-Pro-DAlaNH$_2$ was used to synthesize Boc-Gly-D2Nal-D4ClPhe-D3Pal-Ser-NMeTyr-DLys(Gly-Boc)-Leu-Arg-Pro-DAla-resin. The peptide was cleaved with HF/anisole and lyophylized leaving the free glycine amine residues at positions 0 and 6. The crude peptide (0.24 g, 0.17 mmol), and L-gulonic lactone (0.30 g, 1.7 mmol) were heated in DMF at 85° for 48 h. The solution was concentrated in vacuo and the residue was purified by HPLC to give N-(L-Gulonyl)-Gly-D2Nal-D4ClPhe-D3Pal-Ser-NMeTyr-DLys(Gly-L-Gulonyl)-Leu-Arg-Pro-DAlaNH$_2$ was obtained; R$_t$=17.16 min; FAB Mass spec. m/e 1843 (M+H)$^+$. Amino Acid Analysis: 1.14 Ala; 0.97 Pro; 1.00 Arg; 1.06 Leu; 0.96 Lys; 0.87 NMeTyr; 0.45 Ser; 0.69 3Pal; 0.75 4ClPhe; 1.85 Gly.

EXAMPLE 22

N-Nicotinyl-Gly-D2Nal-D4ClPhe-D3Pal-Ser-NMeTyr-DLys(Gly-Shik)-Leu-Arg-Pro-DAlaNH$_2$ (Compound 111)

The title compound was prepared by the procedure described in Example 15 for N-Shikimyl-Gly-D2Nal-D4ClPhe-D3Pal-Ser-NMeTyr-DLys(Gly-Shik)-Leu-Arg-Pro-DAlaNH$_2$ was used but substituting nicotinic for shikimic acid. After workup, lyophilization and HPLC purification N-Nicotinyl-Gly-D2Nal-D4ClPhe-D3Pal-Ser-NMeTyr-DLys(Gly-Shik)-Leu-Arg-Pro-DAlaNH$_2$ was obtained; R$_t$=23.82 min; FAB Mass spec. m/e 1748 (M+H)$^+$. Amino Acid Analysis: 1.03 Ala; 0.99 Pro; 0.94 Arg; 0.98 Leu; 1.01 Lys; 0.93 NMeTyr; 0.50 Ser; 1.06 3Pal; 1.13 4ClPhe; 2.08 Gly.

EXAMPLE 23

The following compounds were prepared by the procedure described in Example 14 was used but substituting BOC-Ile and BOC-NMeLeu, respectively, for BOC-Leu. After workup, lyophilization and HPLC purification the following compounds were obtained:

Example 23a N-Nicotinyl-Gly-D2Nal-D4ClPhe-D3Pal-Ser-NMeTyr-DLys(Shik)-Ile-Arg-Pro-DAlaNH$_2$ (Compound 112); R$_t$=14.27 min; FAB Mass spec. m/e 1691 (M+H)$^+$. Amino Acid Analysis: 1.04 Ala; 1.04 Pro; 1.00 Arg; 0.95 Ile; 0.96 Lys; 1.79 NMeTyr; 0.47 Ser; 0.99 D3Pal; 1.05 D4ClPhe; 1.01 Gly.

Example 23b N-Nicotinyl-Gly-D2Nal-D4ClPhe-D3Pal-Ser-NMeTyr-DLys(Shikimyl)-NMeLeu-Arg-Pro-DAlaNH$_2$ (Compound 113); R$_t$=15.15 min; FAB Mass spec. m/e 1705 (M+H)$^+$. Amino Acid Analysis: 1.08 Ala; 1.01 Pro; 0.97 Arg; 0.92 Lys; 1.33 NMeTyr; 0.47 Ser; 0.95 3Pal; 1.01 4ClPhe; 1.06 Gly.

EXAMPLE 24

N-Nicotinyl-Gly-D2Nal-D4ClPhe-D3Pal-Ser-NMeTyr-DLys(Shikimyl)-Leu-Arg-Aze-DAlaNH$_2$ (Compound 114)

The title compound was prepared by the procedure described in Example 19 was used but substituting BOC-Aze for BOC-Pro. After workup, lyophilization and HPLC purification Nicotinyl-Gly-D2Nal-D4ClPhe-D3Pal-Ser-NMeTyr-DLys(Shikimyl)-Leu-Arg-Aze-DAlaNH$_2$ was obtained; R$_t$=14.00 min; FAB Mass spec. m/e 1678 (M+H)$^+$. Amino Acid Analysis: 1.02 Ala; 1.00 Arg; 0.97 Lys; 0.46 Ser; 1.15 3Pal; 0.89 4ClPhe; 1.0 Gly.

EXAMPLE 25

The following compounds were prepared by the procedure described in Example 14 was used but substituting BOC-Harg(NO$_2$) for BOC-Arg(Tos). After workup, lyophilization and HPLC purification the following compounds were obtained:

Example 25a N-Nicotinyl-Gly-D2Nal-D4ClPhe-D3Pal-Ser-NMeTyr-DLys(Shik)-Leu-Harg-Pro-DAlaNH$_2$ (Compound 115); R$_t$=30.45 min; FAB Mass spec. m/e 1705 (M+H)$^+$. Amino Acid Analysis: 0.99 Ala; 1.00 Pro; 1.04 Leu; 0.96 Lys; 1.06 NMeTyr; 0.54 Ser; 1.13 3Pal; 1.20 4ClPhe; 1.02 Gly.

Example 25b N-Nicotinyl-DSer-D2Nal-D4ClPhe-D3Pal-Ser-NMeTyr-DLys(Shikimyl)-Leu-Harg-Pro-DAlaNH$_2$ (Compound 116); R$_t$=33.85 min; FAB Mass spec. m/e 1735 (M+H)$^+$. Amino Acid Analysis: 1.03 Ala; 0.99 Pro; 1.00 Leu; 0.98 Lys; 1.04 NMeTyr; 1.05 Ser; 0.97 3Pal; 1.04 4ClPhe.

Example 25c N-(2-Furoyl)-Gly-D2Nal-D4ClPhe-D3Pal-Ser-NMeTyr-DLys(Shik)-Leu-Harg-Pro-DAlaNH$_2$ (Compound 117); R$_t$=40.60 min; FAB Mass spec. m/e 1694 (M+H)$^+$. Amino Acid Analysis: 1.03 Ala; 1.03 Pro; 1.01 Leu; 0.93 Lys; 1.28 NMeTyr; 0.47 Ser; 0.97 3Pal; 1.04 4ClPhe; 0.88 Gly.

Example 25d N-Shikimyl-Gly-D2Nal-D4ClPhe-D3Pal-Ser-NMeTyr-DLys(Shik)-Leu-Harg-Pro-DAlaNH$_2$ (Compound 118); R$_t$=31.95 min; FAB Mass spec. m/e 1756 (M+H)$^+$. Amino Acid Analysis: 0.98 Ala; 1.03 Pro; 1.04 Leu; 0.94 Lys; 1.15 NMeTyr; 0.49 Ser; 1.15 3Pal; 1.20 4ClPhe; 0.97 Gly.

Example 25e N-Nicotinyl-Gly-D2Nal-D4ClPhe-D3Pal-Ser-NMeTyr-DLys(Gly-Shik)-Leu-Harg-Pro-DAlaNH$_2$ (Compound 119); R$_t$=30.27 min; FAB Mass spec. m/e 1762 (M+H)$^+$. Amino Acid Analysis: 1.07 Ala; 1.00 Pro; 0.99 Leu; 0.99 Lys; 1.14 NMeTyr; 0.50 Ser; 0.97 3Pal; 1.04 4 4ClPhe; 2.01 Gly.

Example 25f N-Nicotinyl-Gly-D2Nal-D4ClPhe-D3Pal-Ser-NMeTyr-DLys(Nicotinyl)-Leu-Harg-Pro-DAlaNH$_2$ (Compound 120); R$_t$=18.91 min; FAB Mass spec. m/e 1655 (M+H)$^+$. Amino Acid Analysis: 1.02 Ala; 1.00 Pro; 1.03 Leu; 0.99 Lys; 1.01 NMeTyr; 0.46 Ser; 1.04 3Pal; 1.10 4ClPhe; 0.96 Gly.

Example 25g N-(3-Quinolinylcarbonyl)-Gly-D2Nal-D4ClPhe-D3Pal-Ser-NMeTyr-DLys(Shikimyl)-Leu-Harg-Pro-DAlaNH$_2$ (Compound 124); R$_t$=17.77 min; FAB Mass spec. m/e 1755 (M+H)$^+$. Amino Acid Analysis: 1.01 Ala; 0.99, Pro; 0.98 Leu; 1.01 Lys; 1.41 NMeTyr; 0.49 Ser; 0.93 3Pal; 0.98 4ClPhe; 1.04 Gly.

EXAMPLE 26

The following compounds were prepared by the procedure described in Example 22 was used but substituting the appropriate BOC-amino acids at positions A and X and the appropriate BOC-amino acids for BOC-NMeTyr(O-2,6-diCl-Bzl). After workup, lyophilization and HPLC purification the following compounds were obtained:

Example 26a N-Nicotinyl-Gly-D2Nal-D4ClPhe-D3Pal-Ser-NMePhe-DLys(Shik)-Leu-Harg-Pro-DAlaNH$_2$ (Compound 121); R$_t$=16.79 min; FAB Mass spec. m/e 1689 (M+H)$^+$. Amino Acid Analysis: 1.00 Ala; 0.96 Pro; 0.96 Leu; 1.03 Lys; 0.54 Ser; 0.92 3Pal; 0.97 4ClPhe; 1.05 Gly.

Example 26b N-Nicotinyl-Gly-D2Nal-D4ClPhe-D3Pal-Ser-NMePhe(NO$_2$)-DLys(Shik)-Leu-Harg-Pro-DAlaNH$_2$ (Compound 122); R$_t$=17.83 min; FAB Mass spec. m/e 1736 (M+H)$^+$. Amino Acid Analysis: 1.07 Ala; 0.99 Pro; 1.00 Leu; 0.94 Lys; 0.40 Ser; 0.98 3Pal; 1.04 4ClPhe; 1.00 Gly.

Example 26c N-Shikimyl-Gly-D2Nal-D4ClPhe-D3Pal-Ser-NMePhe(NO$_2$)-DLys(Shik)-Leu-Harg-Pro-DAlaNH$_2$ (Compound 123); R$_t$=17.37 min; FAB Mass spec. m/e 1785 (M+H)$^+$. Amino Acid Analysis: 1.04 Ala; 0.99 Pro; 1.00 Leu; 0.97 Lys; 0.48 Ser; 0.99 3Pal; 1.03 4ClPhe; 0.99 Gly.

EXAMPLE 27

The following compounds were prepared by the procedure described in Example 14 was used but substituting the appropriate BOC-amino acids and acids at positions X, A, G and J. After workup, lyophilization and HPLC purification the following compounds were obtained:

Example 27a N-Nicotinyl-Gly-D2Nal-D4ClPhe-D3Pal-Ser-NMeTyr-DLys(Nic)-Leu-Arg-Pro-DAlaNH$_2$ (Compound 125); R$_t$=15.11 min; FAB Mass spec. m/e 1640 (M+H)$^+$. Amino Acid Analysis: 1.04 Ala; 0.99 Pro; 0.99 Leu; 1.00 Lys; 1.47 NMeTyr; 0.46 Ser; 0.99 3Pal; 1.06 4ClPhe; 1.02Gly.

Example 27b N-(R,S)-Tetrahydrofur-2oyl-Gly-D2Nal-D4ClPhe-D3Pal-Ser-NMeTyr-DLys(Gly-Nic)-Leu-Arg-Pro-DAlaNH$_2$ (Compound 126); R$_t$=18.27 min; FAB Mass spec. m/e 1690 (M+H)$^+$. Amino Acid Analysis: 1.07 Ala; 1.00 Pro; 1.01 Leu; 0.99 Lys; 1.40 NMeTyr; 0.39 Ser; 0.97 3Pal; 1.09 4ClPhe; 1.97Gly.

Example 27c N-Shikimyl-Gly-D2Nal-D4ClPhe-D3Pal-Ser-NMeTyr-DLys(Nic)-Leu-Arg-Aze-DAlaNH$_2$ (Compound 127); R$_t$=14.77 min; FAB Mass spec. m/e 1678 (M+H)$^+$. Amino Acid Analysis: 1.00 Ala; 1.02 Leu; 1.01 Lys; 1.07 NMeTyr; 0.43 Ser; 1.15 3Pal; 0.90 4ClPhe; 0.98.Gly.

Example 27d N-Nicotinyl-3-Aminopropionyl-D2Nal-D4ClPhe-D3Pal-Ser-NMeTyr-DLys(Shikimyl)-Leu-Arg-Pro-DAlaNH$_2$ (Compound 128); R$_t$=30.75 min; FAB Mass spec. m/e 1705 (M+H)$^+$. Amino Acid Analysis :1.01 Ala; .0.98 Pro; 0.95 Arg; 1.04 Leu; 0.96 Lys; 0.90 NMeTyr; 0.55 Ser; 1.13 3Pal; 1.19 4ClPhe.

Example 27e N-Shikimyl-3-Aminopropionyl-D2Nal-D4ClPhe-D3Pal-Ser-NMeTyr-DLys(Shik)-Leu-Arg-Pro-DAlaNH$_2$ (Compound 129); R$_t$=30.95 min; FAB Mass spec. m/e 1756 (M+H)$^+$. Amino Acid Analysis: 1.00 Ala;. 1.03 Pro; 0.99 Arg; 1.04 Leu; 0.95 Lys; 0.35 NMeTyr; 0.50 Ser; 1.12 3Pal; 1.18 4ClPhe.

EXAMPLE 28

N-Nicotinyl-3Aminopropionyl-D2Nal-D4ClPhe-D3Pal-Ser-NMeTyr-DLys(Shik)-Leu-Harg-Pro-DAlaNH$_2$ (Compound 132)

The title compound was prepared by the procedure described in Example 8 was used but substituting BOC-Harg(NO$_2$) instead of BOC-Arg(Tos). After workup, lyophilization and HPLC purification Nicotinyl-3Aminopropionyl-D2Nal-D 4ClPhe-D3Pal-Ser-NMeTyr-DLys(Shik)-Leu-Harg-Pro-DAlaNH$_2$; R$_t$=34.20 min; FAB Mass spec. m/e 1719 (M+H)$^+$. Amino Acid Analysis :1.01 Ala; 0.99 Pro; 0.99 Leu; 1.00 Lys; 1.02 NMeTyr; 0.57 Ser; 0.98 3Pal; 1.04 4ClPhe.

EXAMPLE 29

N-Shikimyl-D2Nal-D4ClPhe-D3Pal-Ser-NMeTyr-DLys(GlyNic)-Leu-Lys(Isp)-Pro-DAlaNH$_2$ (Compound 135)

The title compound was prepared using the method of Example 8 but substituting the appropriate BOC-amino acids and acids at positions 6 and 0. After workup, lyophilization and HPLC purification there was obtained N-Shikimyl-D 2Nal-D4ClPhe-D3Pal-Ser-NMeTyr-DLys-(GlyNic)-Leu-Lys(I sp)-Pro-DAlaNH$_2$; R$_t$=31.31 min; FAB Mass spec. m/e 1705 (M+H)$^+$. Amino Acid Analysis: 0.96

Ala; 1.00 Pro; 0.96 Lys(Isp); 1.00 Leu; 0.85 Lys; 1.08 Gly; 1.08 NMeTyr; 0.49 Ser; 1.13 3Pal; 1.15 4ClPhe (135).

EXAMPLE 30

The following compounds were prepared by the procedure described in Example 11 was used but substituting the appropriate BOC-amino acids and acids at positions 6 and 0. After workup, lyophilization and HPLC purification the following compounds were obtained:

Example 30a N-(R,S)-Tetrahydrofur-2-oyl-Gly-D2Nal-D4ClPhe-D3Pal-Ser-NMeTyr-DLys(Azagly- 2Fur)-Leu-Lys(Isp)-Pro-DAlaNH$_2$ (Compound 136); R$_t$=27.47 and 27.58 min; FAB Mass spec. m/e 1694 (M+H)$^+$. Amino Acid Analysis: 1.02 Ala; 1.02 Pro; 0.95 Lys(Isp); 1.01 Leu; 0.93 Lys; 1.07 NMeTyr; 0.47 Ser; 1.07 3Pal; 1.13 4ClPhe; 1.03 Gly.

Example 30b N-Shik-D2Nal-D4ClPhe-D3Pal-Ser-NMeTyr-DLys(Azagly-Nic)-Leu-Lys(Isp)-Pro-DAlaNH$_2$ (Compound 139); R$_t$=31.21 min; FAB Mass spec. m/e 1707 (M+H)$^+$. Amino Acid Analysis: 1.00 Ala; 1.02 Pro; 0.94 Lys(Isp); 1.02 Leu; 0.87 Lys; 0.87 NMeTyr; 0.5 Ser; 0.97 3Pal; 1.05 ClPhe.

Example 30c N-Shik-D2Nal-D4ClPhe-D3Pal-Ser-NMeTyr-DLys(Azagly-2Fur)-Leu-Lys(Isp)-Pro-DAlaNH$_2$ (Compound 140); R$_t$30.87 min; FAB Mass spec. m/e 1696 (M+H)$^+$. Amino Acid Analysis: 1.00 Ala; 1.03 Pro; 0.92 Lys(Isp); 1.01Leu; 0.96 Lys; 1.16 NMeTyr; 0.5 Ser; 1.05 3Pal; 1.06 ClPhe.

EXAMPLE 31

N-Nicotinyl-Azagly-D2Nal-D4ClPhe-D3Pal-Ser-NMeTyr-DLys(Azagly-Nic)-Leu-Lys(Isp)-Pro-DAlaNH$_2$ (Compound 141)

The title compound was prepared by the procedure described in Example 30 was used but substituting at position 0 NicAzagly using the same method described above for position 6. After workup, lyophilization and HPLC purification NicAzagly-D2Nal-D4ClPhe-D3Pal-Ser-NMeTyr-DLys(Azagly-Nic)-Leu-Lys(Isp)-Pro-DAlaNH$_2$; R$_t$=25.92 min; FAB Mass spec. m/e 1565 (M+H)$^+$. Amino Acid Analysis :1.02 Ala; 0.98 Pro; 0.91 Lys(Isp); 1.00 Leu; 1.00 Lys; 1.44 NMeTyr; 0.50 Ser; 1.01 3Pal; 1.0 4ClPhe.

EXAMPLE 32

N-Nicotinyl-Azagly-D4ClPhe-DBal-Ser-NMeTyr-DLys(Nic)-Leu-Lys(Isp)-Pro-DAlaNH$_2$ (Compound 142)

The title compound was prepared by the procedure described in Example 31 was used but substituting BOC-DLys(Nic) for BOC-DLys(FMOC), BOC-DBal for BOC-D3Pal and skipping the BOC-D2Nal couplings. After workup, lyophilization and HPLC purification Nic-Azagly-D4ClPhe-DBal-Ser-NMeTyr-DLys(Nic)-Leu-Lys(Isp)-Pro-DAlaNH$_2$; R$_t$=19.17 min; FAB Mass spec. m/e 1513 (M+H)$^+$. Amino Acid Analysis: 0.98 Ala; 1.03 Pro; 0.99 Leu; 1.57 Lys; 1.08 NMeTyr; 0.45 Ser.

EXAMPLE 33

The following compounds were prepared by the procedure described in Example 32 was used but substituting the appropriate BOC-amino acids and acids at positions 3 and 0. After workup, lyophilization and HPLC purification the following compounds were obtained:

Example 33a N-(2-Furoyl)-Azagly-D4ClPhe-DBal-Ser-NMeTyr-DLys(Nic)-Leu-Lys(Isp)-Pro-DAlaNH$_2$ (Compound 143); R$_t$=20.41 min; FAB Mass spec. m/e 1502 (M+H)$^+$. Amino Acid Analysis: 0.96 Ala; 1.02 Pro; 1.6 Lys(Isp); 1.02Leu; 0.94 Lys; 1.16 NMeTyr; 0.48 Ser.

Example 33b N-Isonicotinyl-Azagly-D4ClPhe-DBal-Ser-NMeTyr-DLys(Nic)-Leu-Lys(Isp)-Pro-DAlaNH$_2$ (Compound 145); R$_t$=17.23 min; FAB Mass spec. m/e 1513 (M+H)$^+$. Amino Acid Analysis: 1.04 Ala; 1.03 Pro; 0.88 Lys(Isp); 0.99 Leu; 0.94 Lys; 1.23 NMeTyr; 0.63 Ser; 0.86 4ClPhe.

Example 33c N-Nicotinyl-Azagly-D4ClPhe-D1Nal-Ser-NMeTyr-DLys(Nic)-Leu-Lys(Isp)-Pro-DAlaNH$_2$ (Compound 146); R$_t$=18.60 min; FAB Mass spec. m/e 1507 (M+H)$^+$. Amino Acid Analysis: 1.01Ala; 1.02 Pro; 0.95Lys(Isp); 1.00 Leu; 0.96 Lys; 1.09 NMeTyr; 0.41 Ser; 1.00 4ClPhe.

EXAMPLE 34

N-Nicotinyl-Sar-D4ClPhe-DBal-Ser-NMeTyr-DLys(Nic)-Leu-Lys(Isp)-Pro-DAlaNH$_2$ (Compound 147)

The title compound was prepared by the procedure described in Example 33 was used but, instead of introducing NicAzagly after the coupling with BOC-D4ClPhe, the peptide-resin was coupled with BOC-Sar followed by nicotinic acid. After workup, lyophilization and HPLC purification NicSar-D4ClPhe-DBal-Ser-NMeTyr-DLys(Nic)-Leu-Lys(Isp)-Pro-DAlaNH$_2$ was obtained; R$_t$=17.80 min; FAB Mass spec. m/e 1526 (M+H)$^+$. Amino Acid Analysis: 1.04 Ala; 1.01 Pro; 0.90 Lys(Isp); 0.99 Leu; 0.96 Lys; 1.22 NMeTyr; 0.41 Ser; 0.74 4ClPhe.

EXAMPLE 35

The following compounds were prepared by the procedure described in Example 34 was used but coupling with BOC-Gly and nicotinic acid after the coupling with BOC-Sar and substituting the appropriate BOC-amino acids at position 3. After workup, lyophilization and HPLC purification the following compounds were obtained:

Example 35a Nic-Gly-Sar-D4ClPhe-D1Nal-Ser-NMeTyr-DLys(Nic)-Leu-Lys(Isp)-Pro-DAlaNH$_2$ (Compound 148); R$_t$=17.25 min; FAB Mass spec. m/e 1578 (M+H)$^+$. Amino Acid Analysis: 0.99 Ala; 1.02 Pro; 0.88 Lys(Isp); 1.03 Leu; 1.05 Lys; 1.07 NMeTyr; 0.48 Ser; 1.15 4ClPhe; 0.92 Sar; 0.92 Gly.

Example 35b Nic-Gly-Sar-D4ClPhe-DBal-Ser-NMeTyr-DLys(Nic)-Leu-Lys(Isp)-Pro-DAlaNH$_2$ (Compound 149); R$_t$=16.30 min; FAB Mass spec. m/e 1584 (M+H)$^+$. Amino Acid Analysis: 1.10 Ala; 1.02 Pro; 0.94 Lys(Isp); 0.97 Leu; 0.96 Lys; 1.10 NMeTyr; 0.41 Ser; 1.03 Sar; 0.95 Gly.

EXAMPLE 36

The following compound was prepared by the procedure described in Example 2 but substituting BOC-3-aminopropanoic acid for BOC-Gly and BOC-D-Bal for BOC-D-3-Pal. After workup, lyophilization and HPLC purification there was obtained:

N-Nicotinyl-3-Aminopropionyl-D2Nal-D4ClPhe-DBal-Ser-NMeTyr-DLys(N-epsilon-Nicotinyl) -Leu-Lys(N-epsilon-Isopropyl)-Pro-DAlaNH$_2$ (Compound 151) was obtained; R$_t$=18.39 min; FAB Mass spec. m/e 1726 (M+H)$^+$.

Amino Acid Analysis: 0.92 Ala; 0.98 Pro; 1.01 Lys(Isp); 1.02 Leu; 1.08 Lys; 1.18 NMeTyr; 0.36 Ser; 1.04 4ClPhe.

EXAMPLE 37

The following compounds were prepared by the procedure described in Example 31 was used but substituting the appropriate BOC-amino adds and acid hydrazides. After workup, lyophilization and HPLC purification the following compounds were obtained:

Example 37a N-(2-Furoyl)-Azagly-D2Nal-D4ClPhe-D3Pal-Ser-NMeTyr-DLys(Nic)-Leu-Lys(Isp)-Pro-DAlaNH$_2$ (Compound 155); R$_t$=21.49 min; FAB Mass spec. m/e 1644 (M+H)$^+$. Amino Acid Analysis: 0.98 Ala; 1.02 Pro; 1.64 Lys; 1.01 Leu; 0.82 NMeTyr; 0.56 Ser.

Example 37b N-Nicotinyl-Azagly-D2Nal-D4ClPhe-D3Pal-Ser-NMeTyr-DLys(Nic)-Leu-Lys(Isp)-Pro-DAlaNH$_2$ (Compound 156); R$_t$=17.60 min; FAB Mass spec. m/e 1655 (M+H)$^+$. Amino Acid Analysis: 0.98 Ala; 1.03 Pro; 1.60 Lys; 1.01 Leu; 1.12 NMeTyr; 0.46 Ser.

Example 37c N-Salicyl-Azagly-D2Nal-D4ClPhe-D3Pal-Ser-NMeTyr-DLys(Nic)-Leu-Lys(Isp)-Pro-DAlaNH$_2$ (Compound 157); R$_t$=20.35 min; FAB Mass spec. m/e 1671 (M+H)$^+$. Amino Acid Analysis: 0.99 Ala; 1.01 Pro; 0.98 Lys; 1.01 Leu; 1.12 NMeTyr; 0.46 Ser.

Example 37d N-Isonicotinyl-Azagly-D2Nal-D4ClPhe-D3Pal-Ser-NMeTyr-DLys(Nic)-Leu-Lys(Isp)-Pro-DAlaNH$_2$ (Compound 158); R$_t$=19.30min; FAB Mass spec. m/e 1655 (M+H)$^+$. Amino Acid Analysis: 1.00 Ala; 1.02 Pro; 0.87 Lys(Isp); 1.04 Leu; 0.95 Lys; 1.04 NMeTyr; 0.46 Ser; 1.06 3Pal; 1.04 4ClPhe.

Example 37e N-Tosyl-Azagly-D2Nal-D4ClPhe-D3Pal-Ser-NMeTyr-DLys(Nic)-Leu-Lys(Isp)-Pro-DAlaNH$_2$ (Compound 160); R$_t$=21.17 min; FAB Mass spec. m/e 1704 (M+H)$^+$. Amino Acid Analysis: 1.07 Ala; 1.01 Pro; 0.90 Lys(Isp); 1.01Leu; 0.94 Lys; 1.04 NMeTyr; 0.51 Ser.

EXAMPLE 38

N-(R,S)-Tetrahydrofur-2-oyl-Gly-D2Nal-D4ClPhe-D3Pal-Ser-NMeTyr-DLys(Nicotinyl)-Leu-Lys(Isp)-Pro-SarNH$_2$ (Compound 165)

The title compound was prepared using the procedure described in Example 3 but substituting BOC-SarNH-resin for BOC-DAlaNH-resin. After workup, lyophilization and. HPLC purification (R,S) Tetrahydrofur-2-oyl-Gly-D2Nal-D 4ClPhe-D3Pal-Ser-NMeTyr-DLys(Nicotinyl)-Leu-Lys(Isp)-Pro-SarNH$_2$ (165) is obtained as the trifluoroacetic acid salt. R$_t$=17.03 and 18.04 min; FAB Mass spec. m/e 1646 (M+H)$^+$. Amino Acid Analysis: 1.01 Sar; 1.0 Pro; 1.23 Lys(Isp); 1.01 Leu; 1.02 Lys; 1.12 NMeTyr; 0.51 Ser; 1.13 3Pal; 1.31 4ClPhe.

EXAMPLE 39

N-(S)-Tetrahydrofur-2-oyl-Gly-D2Nal-D4ClPhe-D3Pal-Ser-NMeTyr-DLys(Nicotinyl)-Leu-Lys(Isp)-Pro-SarNH$_2$ (Compound 166)

The procedure described in Example 4 was used but substituting BOC-SarNH-resin for BOC-DAlaNH-resin. After work-up, lyophilization, and HPLC purification N-(S)-2-Tetrahydrofuroyl-Gly-D2Nal-D4ClPhe-D 3Pal-Ser-NMeTyr-DLys(Nic)-Leu-Lys(N-epsilon-Isopropyl)-Pro-SarNH$_2$ was obtained as the trifluoroacetate salt; R$_t$=19.75 min; FAB Mass spec. m/e 1647 (M+H)$^+$. Amino Acid Analysis: 0.90 Sar; 0.99 Pro; 1.0 Lys(Isp); 0.99 Leu; 0.99 Lys; 1.03 NMeTyr; 0.39 Ser; 0.97 D3Pal; 1.03 D4ClPhe; 1.02 Gly.

EXAMPLE 40

N-(R)-Tetrahydrofur-2-oyl-Gly-D2Nal-D4ClPhe-D3Pal-Ser-NMeTyr-DLys(Nicotinyl)-Leu-Lys(Isp)-Pro-SarNH$_2$ (Compound 167)

The procedure described in Example 5 is used but substituting BOC-SarNH-resin instead of BOC-DAlaNH-resin. After workup, lyophilization and HPLC purification (R)-Tetrahydrofur-2-ol-Gly-D2Nal-D4ClPhe-D3Pal-Ser-NMeTyr-DLys(Nicotinyl)-Leu-Lys(Isp)-Pro-SarNH$_2$ (167) is obtained as the trifluoroacetic acid salt.

EXAMPLE 41

N-(R,S)-Tetrahydrofur-2-oyl-Gly-D2Nal-D4ClPhe-D 3Pal-Ser-Tyr-DLys(Nicotinyl)-Leu-Lys(Isp)-Pro-SarNH$_2$ (Compound 168)

The procedure described in Example 1 is used but substituting the BOC-Tyr(O-2,6diClBzl) for BOC-NMe-Tyr(O-2,6Cl-Bzl). After workup, lyophilization and HPLC purification (R,S) Tetrahydrofur-2-oyl-Gly-D2Nal-D4ClPhe-D 3Pal-Ser-Tyr-DLys(Nicotinyl)-Leu-Lys(Isp)-Pro-SarNH$_2$ (168) is obtained as the trifluoroacetic acid salt.

EXAMPLE 42

N-(R,S)-Tetrahydrofur-2-oyl-Gly-D2Nal-D4ClPhe-D3Pal-Ser-Lys(Nic)-DLys(Nicotinyl)-Leu-Lys(Isp)-Pro-SarNH$_2$ (Compound 169)

The procedure described in Example 41 is used but substituting BOC-Lys(Nic) for BOC-Tyr(O-2,6Cl-Bzl). After workup, lyophilization and HPLC purification (R,S) Tetrahydrofur-2-oyl-Gly-D2Nal-D4ClPhe-D 3Pal-Ser-Lys-(Nic)-DLys(Nicotinyl)-Leu-Lys(Isp)-Pro-SarNH$_2$ (169) is obtained as the trifluoroacetic acid salt.

EXAMPLE 43

N-(R,S)-Tetrahydrofur-2-oyl-Gly-D2Nal-D4ClPhe-D3Pal-Ser-Tyr-DCit-Leu-Arg-Pro-SarNH$_2$ (Compound 170)

The procedure described in Example 41 is used but substituting BOC-DCit and BOC-Arg(Tos) for BOC-DLys-(Nic) and BOC-Lys(Cbz,Isp), respectively. After workup, lyophilization and HPLC purification (R,S) Tetrahydrofur-2-oyl-Gly-D 2Nal-D4ClPhe-D3Pal-Ser-Tyr-DCit-Leu-Arg-Pro-SarNH$_2$ (170) is obtained as the trifluoroacetic acid salt.

EXAMPLE 44

N-(R,S)-Tetrahydrofur-2-oyl-Gly-D2Nal-D4ClPhe-D3Pal-Ser-Tyr-DHcit-Leu-Arg-Pro-SarNH$_2$ (Compound 171)

The procedure described in Example 41 is used but substituting BOC-DHcit for BOC-DLys(Nic). After workup, lyophilization and HPLC purification (R,S) Tetrahydrofur-2-oyl-Gly-D2Nal-D4ClPhe-D3Pal-Ser-Tyr-DHcit-Leu-Arg-Pro-SarNH$_2$ (171) is obtained as the trifluoroacetic acid salt.

EXAMPLE 45

N-(R,S)-Tetrahydrofur-2-oyl-Gly-D2Nal-D4ClPhe-
D3Pal-Ser-Tyr-DHcit-Leu-Lys(Isp)-Pro-SarNH$_2$
(Compound 172)

The procedure described in Example 44 is used but substituting BOC-Lys(Isp,Cbz) for BOC-Arg(Tos). After workup, lyophilization and HPLC purification (R,S) Tetrahydrofur-2-oyl-Gly-D2Nal-D4ClPhe-D3Pal-Ser-Tyr-DHcit-Leu-Lys(Isp)-Pro-SarNH$_2$ (172) is obtained as the trifluoroacetic acid salt.

EXAMPLE 46

N-(R,S)-Tetrahydrofur-2-oyl-Gly-D2Nal
-D4ClPhe-D3Pal-Ser-Arg-D-4(pOMeBzol)Hala-Leu-
Arg-Pro-SarNH$_2$ (Compound 173)

The procedure described in Example 43 is used but substituting BOC-Arg(Tos) and BOC-D-4-(p-OMe-Benzoyl)Homoalanyl for BOC-Tyr(O-2,6-diClBzl) and BOC-DCit, respectively. After workup, lyophilization and HPLC purification (R,S) Tetrahydrofur-2-oyl-Gly-D2Nal-D4ClPhe-D3Pal-Ser-Arg-D4(pOMeBzol)-Leu-Arg-Pro-SarNH$_2$ (173) is obtained as the trifluoroacetic acid salt.

EXAMPLE 47

N-(R,S)-Tetrahydrofur-2-oyl-Gly-D2Nal-D4ClPhe-
D3Pal-Ser-Tyr-DHarg(Et$_2$)-Leu-Harg(Et$_2$)-Pro-SarNH$_2$ (Compound 174)

The procedure described in Example 43 is used but substituting BOC-DHarg(Et$_2$) and BOC-Harrg(Et$_2$) for BOC-DCit and BOC-Arg(Tos), respectively. After workup, lyophilization and HPLC purification (R,S) Tetrahydrofur-2-oyl-Gly-D2Nal-D4ClPhe-D 3Pal-Ser-Tyr-DHarg(Et$_2$)-Leu-Harg(Et$_2$)-Pro-SarNH$_2$ (174) is obtained as the trifluoroacetic acid salt.

EXAMPLE 48

N-(R,S)-Tetrahydrofur-2-oyl-Gly-D2
Nal-D4ClPhe-D3Pal-Ser-NMePhe(Atz)-DPhe(Atz)-
Leu-Lys(Isp)-Pro-SarNH$_2$ (Compound 175)

The procedure described in Example 38 is used but substituting BOC-NMePhe(4NFMOC) and BOC-DPhe(4NFMOC) for BOC-NMeTyr(O-2,6-ClBzl) and BOC-DLys(Nic). The peptide-resin was treated with 30% piperidine in DMF for 2 hr, then washed three times with (1:1) DMF/DCM, treated with a solution of diphenyl cyanocarbonimidate (0.43 g) in DMF (15 mL) and the mixture was bubbled for 16 hr. The resin was washed three times each with DCM/DMF, MeOH, and DCM, then treated with hydrazine (10 mL) for 8 hr. The resin was again washed as previously and dried in vacuo overnight over P$_2$O$_5$. After cleavage of the peptide from the resin with HF, workup, lyophilization and HPLC purification (R,S) Tetrahydrofur-2-oyl-Gly-D2Nal-D4ClPhe-D 3Pal-Ser-NMePhe(Atz)-DPhe(Atz)-Leu-Lys(Isp)-Pro-SarNH$_2$ (175) is obtained as the trifluoroacetic acid salt.

EXAMPLE 49

N-(R,S)-Tetrahydrofur-2-oyl-Gly-D2Nal-D4ClPhe-
D3Pal-Ser-Phe(Atz)-DPhe(Atz)-Leu-LyS(Isp)-Pro-
SarNH$_2$ (Compound 176)

The procedure described in Example 48 is used but substituting BOC-Phe(4NFMOC) for BOC-NMePhe(4NFMOC). After workup, lyophilization and HPLC purification (R,S) Tetrahydrofur-2-oyl-Gly-D2Nal-D4ClPhe-D3Pal-Ser-Phe(Atz)-DPhe(Atz)-Leu-Lys(Isp)-Pro-SarNH$_2$ (176) is obtained as the trifluoroacetic acid salt.

EXAMPLE 50

N-(R,S)-Tetrahydrofur-2-oyl-Gly-D2Nal-D4ClPhe-
D3Pal-Ser-NMePhe(Me-Atz)-DPhe(Me-Atz)-Leu-
Lys(Isp)-Pro-SarNH$_2$ (Compound 177)

The procedure described in Example 48 is used but substituting BOC-NMePhe(4Me-NFMOC) and BOC-DPhe(4Me-NFMOC) for BOC-NMePhe(4NFMOC) and BOC-DPhe(4NFMOC). After workup, lyophilization and HPLC purification (R,S) Tetrahydrofur-2-oyl-Gly-D2Nal-D4ClPhe-D3Pal-Ser-NMePhe(Me-Atz)-DPhe(Me-Atz)-Leu-Lys(Isp) -Pro-SarNH$_2$ (177) is obtained as the trifluoroacetic acid salt.

EXAMPLE 51

N-(R,S)-Tetrahydrofur-2-oyl-Gly-D2Nal-D4ClPhe-
D3Pal-Ser-Lys(Atz)-DLys(Atz)-Leu-Lys(Isp)-Pro-
SarNH$_2$ (Compound 178)

The procedure described in Example 48 is used but substituting BOC-Lys(FMOC) and BOC-DLys(NFMOC) for BOC-NMePhe(4N-FMOC) and BOC-DPhe(4NFMOC), respectively. After workup, lyophilization and HPLC purification (R,S) Tetrahydrofur-2-oyl-Gly-D2Nal-D4ClPhe-D3Pal-Ser-Lys(Atz)-DLys(Atz)-Leu-Lys(Isp)-Pro-SarNH$_2$ is obtained as the trifluoroacetic acid salt.

EXAMPLE 52

The procedures described in Examples 41–49 are used but substituting BOC-DAla-NH-resin for BOC-Sar-NH-resin. After workup, lyophilization and HPLC purification the following compounds are obtained as the trifluoroacetic acid salt:

Example 52a N-(R,S)-Tetrahydrofur-2-oyl-Gly-D2Nal-D4ClPhe-D3Pal-Ser-Tyr-DLys(Nicotinyl) -Leu-Lys(Isp)-Pro-DAlaNH$_2$ (Compound 179).

Example 52b N-(R,S)-Tetrahydrofur-2-oyl-Gly-D2Nal-D4ClPhe-D3Pal-Ser-Lys(Nic)-DLys(Nicotinyl) -Leu-Lys(Isp)-Pro-DAlaNH$_2$ (Compound 180).

Example 52c N-(R,S)-Tetrahydrofur-2-oyl-Gly-D2Nal-D4ClPhe-D3Pal-Ser-Tyr-DCit-Leu-Arg-Pro-DAlaNH$_2$ (Compound 181).

Example 52d N-(R,S)-Tetrahydrofur-2-oyl-Gly-D2Nal-D4ClPhe-D3Pal-Ser-Tyr-DHcit-Leu-Arg-Pro-DAlaNH$_2$ (Compound 182).

Example 52e N-(R,S)-Tetrahydrofur-2-oyl-Gly-D2Nal-D4ClPhe-D3Pal-Ser-Tyr-DHcit-Leu-Lys(Isp)-Pro-DAlaNH$_2$ (Compound 183).

Example 52f N-(R,S)-Tetrahydrofur-2-oyl-Gly-D2Nal-D4ClPhe-D3Pal-Ser-Arg-D 4(pOMeBzol)Hala-Leu-Arg-Pro-DAlaNH$_2$ (Compound 184).

Example 52g  N-(R,S)-Tetrahydrofur-2-oyl-Gly-D2Nal-D4ClPhe-D3Pal-Ser-Tyr-DHarg(Et$_2$)-Leu-Harg(Et$_2$)-Pro-DAlaNH$_2$ (Compound 185).

Example 52h  N-(R,S)-Tetrahydrofur-2-oyl-Gly-D2Nal-D4ClPhe-D3Pal-Ser-NMePhe(Atz)-DPhe(Atz)-Leu-Lys(Isp)-Pro-DAlaNH$_2$ (Compound 186).

Example 52i  N-(R,S)-Tetrahydrofur-2-oyl-Gly-D2Nal-D4ClPhe-D3Pal-Ser-Phe(Atz)-DPhe(Atz)-Leu-Lys(Isp)-Pro-DAlaNH$_2$ (Compound Compound 187).

Example 52j  N-(R,S)-Tetrahydrofur-2-oyl-Gly-D2Nal-D4ClPhe-D3Pal-Ser-NMePhe(Me-Atz)-DPhe(Me-Atz)-Leu-Lys(Isp)-Pro-DAlaNH$_2$ (Compound 188).

Example 52k  N-(R,S)-Tetrahydrofur-2-oyl-Gly-D2Nal-D4ClPhe-D3Pal-Ser-Lys(Atz)-DLys(Atz)-Leu-Lys(Isp)-Pro-DAlaNH$_2$ (Compound 189).

EXAMPLE 53

The procedure described in Example 31 is used but substituting BOC-SarNH-resin for BOC-DAlaNH-resin and substituting the appropriate amino acids and acids at position 6. After workup, lyophilization and HPLC purification the following compounds are obtained as the trifluoroacetic acid salt:

Example 53a  N-(R,S)-Tetrahydrofur-2-oyl-Gly-D2Nal-D4ClPhe-D3Pal-Ser-NMeTyr-DLys(Azgly-2Fur)-Leu-Lys(Isp)-Pro-SarNH$_2$ (Compound 190).

Example 53b  N-(R,S)-Tetrahydrofur-2-oyl-Gly-D2Nal-D4ClPhe-D3Pal-Ser-NMeTyr-DLys(Azgly-Nic)-Leu-Lys(Isp)-Pro-SarNH$_2$ (Compound 191).

Example 53c  N-(R,S)-Tetrahydrofur-2-oyl-Gly-D2Nal-D4ClPhe-D3Pal-Ser-NMeTyr-DLys(Gly-Nic)-Leu-Lys(Isp)-Pro-SarNH$_2$ (Compound 192).

EXAMPLE 54

N-Nicotinyl-Gly-D2Nal-D4ClPhe-D3Pal-Ser-NMeTyr-DLys(Shik)-Leu-Harg-Pro-SarNH$_2$
(Compound 193)

The procedure described in Example 1 is used but substituting the appropriate BOC-amino acids for BOC-Gly, BOC-DLys-FMOC for BOC-DCit, and BOC-Sar-NH-resin for BOC-DAla-NH-resin. After workup, lyophilization and HPLC purification Nic-Gly-D2Nal-D4ClPhe-D3Pal-Ser-NMeTyr-DLys(Shik)-Leu-Harg-Pro-SarNH$_2$ is obtained as the trifluoroacetate salt.

EXAMPLE 55

N-(R,S)-Tetrahydrofur-2-oyl-Gly-D2Nal-D4ClPhe-D3Pal-Ser-NMeTyr-DLys(Shik)-Leu-Harg-Pro-DAlaNH$_2$ (Compound 194)

The procedure described in Example 54 is used but substituting BOC-DAlaNH-resin for BOC-SarNH-resin. After workup, lyophilization and HPLC purification N-(R,S)4H2Fur-Gly-D2Nal-D4ClPhe-D3Pal-Ser-NMeTyr-DLys(Shik)-Leu-Harg-Pro-DAlaNH$_2$ is obtained as the trifluoroacetate salt.

EXAMPLE 56

N-(R,S)-Tetrahydrofur-2-oyl-Gly-D2Nal-D4ClPhe-D3Pal-Ser-NMeTyr-DLys(Shik)-Leu-Harg-Pro-SarNH$_2$ (Compound 195)

The procedure described in Example 55 is used but substituting (R,S)-tetrahydro-2-furoic acid for nicotinic acid. After workup, lyophilization and HPLC purification N-(R,S) 4H2Fur-Gly-D2Nal-D4ClPhe-D3Pal-Ser-NMeTyr-DLys(Shik)-Leu-Harg-Pro-SarNH$_2$ is obtained as the trifluoroacetate salt.

EXAMPLE 57

N-Shikimyl-Gly-D2Nal-D4ClPhe-D3Pal-Ser-NMeTyr-DLys(Shik)-Leu-Harg-Pro-SarNH$_2$
(Compound 196)

The procedure described in Example 54 is used but shikimic acid for nicotinic acid. After workup, lyophilization and HPLC purification Shik-Gly-D2Nal-D 4ClPhe-D3Pal-Ser-NMeTyr-DLys(Shik)-Leu-Harg-Pro-SarNH$_2$ is obtained as the trifluoroacetate salt.

EXAMPLE 58

N-Nicotinyl-Gly-D2Nal-D4ClPhe-D3Pal-Ser-NMePhe(4AmAtz)-DLys(Shik)-Leu-Harg-Pro-DAlaNH$_2$
(Compound 197)

The procedure described in Example 54 is used but substituting the appropriate BOC-amino acids and acids at positions 0, 6 and 8. After workup, lyophilization and HPLC purification Nic-Gly-D2Nal-D4ClPhe-D3Pal-Ser-NMePhe(4AmAtz)-DLys(Shik)-Leu-Harg-Pro-DAlaNH$_2$ is obtained as the trifluoroacetate salt.

EXAMPLE 59

N-Nicotinyl-Gly-D3Qal-D4ClPhe-D3Pal-Ser-NMeTyr-DLys(Shik)-Leu-Harg-Pro-DAlaNH$_2$
(Compound 198)

The procedure described in Example 14 is used but substituting BOC-3Qal for BOC-D2Nal. After workup, lyophilization and HPLC purification Nic-Gly-D3Qal-D 4ClPhe-D3Pal-Ser-NMeTyr-DLys(Shik)-Leu-Harg-Pro-DAlaNH$_2$ is obtained as the trifluoroacetate salt.

EXAMPLE 60

N-Nicotinyl-Gly-D2Nal-D4ClPhe-D3Pal-Ser-NMeTyr-DLys(COdiAmpropShik)-Leu-Harg-Pro-SarNH$_2$ (Compound 199)

The procedure described in Example 54 is used to obtain Nic-Gly-D2Nal-D 4ClPhe-D3Pal-Ser-NMeTyr-DLys(FMOC)-Leu-Harg-Pro-SarNH-resin. This was then treated with excess of 1,1'-N,N'-carbonyldiimidazole in DMF for 20 min. The resin was washed three times with (1:1) DMF/DCM and the treated with excess of diaminoproprane in DMF for 1 hr. The resin was again washed as previously described and reacted with shikimic acid in DMF using two couplings of 6 hr each. After workup, lyophilization and HPLC purification Nic-Gly-D2Nal-D4ClPhe-D3Pal-Ser-NMeTyr-DLys(COdiAmpropShik)-Leu-Harg-Pro-SarNH$_2$ is obtained as the trifluoroacetate salt.

EXAMPLE 61

(R,S)4H2Fur-Gly-D2Nal-D4ClPhe-D3Pal-Ser-NMeTyr-DLys(COdiAmpropShik)-Leu-Lys(Isp)-Pro-DAlaNH$_2$ (Compound 200)

The procedure described in Example 60 is used to obtain (R,S)-4H2Fur-Gly-D 2Nal-D4ClPhe-D3Pal-Ser-NMeTyr-DLys(FMOC)-Leu-Lys(Isp)-Pro-DAlaNH-resin. This was then treated with excess of 1,1'-N,N'-carbonyldiimidazole in DMF for 20 min. The resin was washed three times with (1:1) DMF/DCM and the treated with excess of diaminoproprane in DMF for 1 hr. The resin was again washed as previously described and reacted with shikimic acid in DMF using two couplings of 6 hr each. After workup, lyophilization and HPLC purification (R,S) 4H2Fur-Gly-D- 2Nal-D4ClPhe-D3Pal-Ser-NMeTyr-DLys(COdiAmpropShik)-Leu-Lys(Isp)-Pro-DAlaNH$_2$ is obtained as the trifluoroacetate salt.

EXAMPLE 62

N-(R,S)-Tetrahydrofur-2-oyl-Gly-D2Nal-D4ClPhe-D3Pal-Ser-NMeTyr-DLys(COdiAmpropShik)-Leu-Harg-Pro-SarNH$_2$ (Compound 201)

The procedure described in Example 61 is used but substituting SarNH-resin for BOC-DAlaNH-resin. After workup, lyophilization and HPLC purification (R,S) 4H-2Fur-Gly-D2Nal-D4ClPhe-D3Pal-Ser-NMeTyr-DLys(COdiAmpropShik)-Leu-Harg-Pro-SarNH$_2$ is obtained as the trifluoroacetate salt.

EXAMPLE 63

(R,S) 4H2Fur-Gly-D2Nal-D4ClPhe-D3Pal-Ser-NMeTyr-DLys(COdiAmpropNic)-Leu-Lys(Isp)-Pro-SarNH$_2$ (Compound 202)

The procedure described in Example 62 is used but substituting nicotinic acid for shikimic acid. After workup, lyophilization and HPLC purification (R,S) 4H2Fur-Gly-D2Nal-D4ClPhe-D3Pal-Ser-NMeTyr-DLys(COdiAmpropNic)-Leu-Lys(Isp)-Pro-SarNH$_2$ is obtained as the trifluoroacetate salt.

EXAMPLE 64

Nic-Gly-D3Qal-D4ClPhe-D3Pal-Ser-cis-Cha(4AmPrz)-DLys(Pic)-Leu-Arg-Pro-DAlaNH$_2$ (Compound 203)

The procedure described in Example 59 is used but substituting BOC-cis-Cha(4Am-Prz) for BOC-NMeTyr(O-2,6-Cl-Bzl) and picolinic acid for nicotinic acid. After workup, lyophilization and HPLC purification Nic-Gly-D3Qal-D4ClPhe-D3Pal-Ser-cis-Cha(4AmPrz)-DLys(Pic)-Leu-Arg-Pro-DAlaNH$_2$ is obtained as the trifluoroacetate salt.

EXAMPLE 65

The procedure described in Example 2 is used but substituting BOC-Sar-NH-resin for for BOC-DAla-NH-resin. After work-up, lyophilization, and HPLC purification the following compounds are obtained:

Example 65a NShikimyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$ (Compound 207).

Example 65b N-Dihydroshikimyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$ (Compound 208).

Example 65c N-2Furoyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$ (Compound 209).

Example 65d N-3Furoyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$ (Compound 210).

Example 65e N-Picolyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$ (Compound 211).

Example 65f N-Nicotinyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$ (Compound 212).

Example 65g N-Isonicotinyl-Gly-D2Nal-D4ClPhe-D3Pal-Ser-NMeTyr-DLys(N-epsilon-Nicotinyl) -Leu-Lys(N-epsilon-Isopropyl)-Pro-SarNH$_2$ (Compound 213).

EXAMPLE 66

N-Tosyl-D2Nal-D4ClPhe-D3Pal-Ser-NMeTyr-DCit-Leu-Arg-Pro-DAlaNH$_2$ (Compound 10c)

The procedure described in Example 1 was used but instead of coupling with acetic acid the resin-peptide was reacted with 10-fold excess of p-toluene sulfonyl chloride and 1-fold excess of pyridine in DMF overnight. After work-up, lyophilization, and HPLC purification N-Tosyl-D2Nal-D4ClPhe-D3Pal-Ser-NMeTyr-DCit-Leu-Arg-Pro-DAlaNH$_2$ was obtained; R$_t$=43.35 min; FAB Mass spec. m/e 1556 (M+H)$^+$. Amino Acid Analysis: 1.03 Ala; 1.00 Pro; 0.98 Arg; 0.99 Leu; 0.91 Cit; 1.01 NMeTyr; 0.50 Ser; 0.98 3Pal; 1.02 4ClPhe.

EXAMPLE 67

N-(S)-Tetrahydrofur-2-oyl-D2Nal-D4ClPhe-D3Pal-Ser-NMeTyr-DLys(Nic)-Leu-Lys(Isp)-Pro-DAlaNH$_2$ (Compound 12b)

The procedure described in Example 1 was used but substituting (S)-tetrahydro-2-furoic acid for BOC-DTyr(O-2,6-Cl-Bzl) and skipping the coupling with acetic acid. After work-up, lyophilization, and HPLC purification N-(S)-Tetrahydrofur-2-oyl-D 2Nal-D4ClPhe-D3Pal-Ser-NMeTyr-DLys(Nic)-Leu-Lys(Isp)-Pro-DAlaNH$_2$ was obtained; R$_t$=28.38 min; FAB Mass spec. m/e 1591 (M+H)$^+$. Amino Acid Analysis: 0.98 Ala; 1.00 Pro; 1.01 Leu; 1.69 Lys; 0.69 NMeTyr; 0.51 Ser.

EXAMPLE 68

N-(R)-Tetrahydrofur-2-oyl-D2Nal-D4ClPhe-D3Pal-Ser-NMeTyr-DLys(Nic)-Leu-Lys(Isp)-Pro-DAlaNH$_2$ (Compound 13b)

The procedure described in Example 67 was used but substituting (R)-tetrahydro-2-furoic acid for (S)-tetrahydro-2-furoic acid. After work-up, lyophilization, and HPLC purification N-(R)-Tetrahydrofur-2-oyl-D2Nal-D4ClPhe-D3Pal-Ser-NMeTyr-DLys(Nic)-Leu-Lys(Isp)-Pro-DAlaNH$_2$ was obtained; R$_t$=29.51 min; FAB Mass spec. m/e 1591 (M+H)$^+$. Amino Acid Analysis: 0.97 Ala; 1.01 Pro; 0.81 Leu; 1.66 Lys; 0.81 NMeTyr; 0.52 Ser.

EXAMPLE 69

N-(S)-Tetrahydrofur-3-oyl-D2Nal-D4ClPhe-D3Pal-Ser-NMeTyr-DLys(Nic)t-Leu-Lys(Isp)-Pro-DAlaNH$_2$ (Compound 14b)

The procedure described in Example 67 was used but substituting (S)-tetrahydro-3-furoic acid for (S)-tetrahydro-2-furoic acid. After work-up, lyophilization, and HPLC purification N-(S)-Tetrahydrofur-3-oyl-D2Nal-D4ClPhe-D3Pal-Ser-NMeTyr-DLys(Nic)-Leu-Lys(Isp)-Pro-DAlaNH$_2$ was obtained; R$_t$=26.41 min; FAB Mass spec. m/e 1591 (M+H)⁺. Amino Acid Analysis: 1.02 Ala; 0.99 Pro; 0.95 Lys(Isp); 1.0 Leu; 0.99 Lys; 0.86 NMeTyr; 0.50 Ser; 0.99 3Pal; 1.05 4ClPhe.

EXAMPLE 70

N-(R)-Tetrahydrofur-3-oyl-D2Nal-D4ClPhe-D3Pal-Ser-NMeTyr-DLys(Nic)-Leu-Lys(Isp)-Pro-DAlaNH$_2$ (Compound 15b)

The procedure described in Example 69 was used but substituting (R)-tetrahydro-3-furoic acid for (S)-tetrahydro-2-furoic acid. After work-up, lyophilization, and HPLC purification N-(R)-Tetrahydrofur-3-oyl-D2Nal-D4ClPhe-D3Pal-Ser-NMeTyr-DLys(Nic)-Leu-Lys(Isp)-Pro-DAlaNH$_2$ was obtained; R$_t$=26.88 min; FAB Mass spec. m/e 1591 (M+H)⁺. Amino Acid Analysis: 1.01Ala; 1.01 Pro; 0.93 Lys(Isp); 1.0 Leu; 1.00 Lys; 1.00 NMeTyr; 0.58 Ser; 1.03 3Pal; 1.05 4ClPhe.

EXAMPLE 71

N-Shikimyl-D2Nal-D4ClPhe-D3Pal-Ser-NMeTyr-DLys(Nic)-Leu-Lys(Isp)-Pro-DAlaNH$_2$ (Compound 16b)

The procedure described in Example 67 was used but substituting shikimic acid for (S)-tetrahydro-2-furoic acid. After work-up, lyophilization, and HPLC purification N-Shikimyl-D2Nal-D4ClPhe-D3Pal-Ser-NMeTyr-DLys(Nic)-Leu-Lys(Isp)-Pro-DAlaNH$_2$ was obtained; R$_t$=23.53 min; FAB Mass spec. m/e 1648 (M+H)⁺. Amino Acid Analysis: 0.99 Ala; 1.0 Pro; 0.81 Leu; 1.64 Lys; 0.76 NMeTyr; 0.56 Ser.

EXAMPLE 72

The procedure described in Example 71 was used but substituting the appropriate acids for shikimic acid. After work-up, lyophilization, and HPLC purification the following compounds were obtained:

Example 72a N-2-Furoyl-D2Nal-D4ClPhe-D3Pal-Ser-NMeTyr-DLys(Nic)-Leu-Lys(Isp)-Pro-DAlaNH$_2$ (Compound 17b) R$_t$=29.51 min; FAB Mass spec. m/e 1586 (M+H)⁺. Amino Acid Analysis: 0.98 Ala; 1.01 Pro; 1.01 Leu; 1.63 Lys; 0.89 NMeTyr; 0.53 Ser.

Example 72b N-3-Furoyl-D2Nal-D4ClPhe-D3Pal-Ser-NMeTyr-DLys(Nic)-Leu-Lys(Isp)-Pro-DAlaNH$_2$ (Compound 18b) R$_t$=30.75 min; FAB Mass spec. m/e 1586 (M+H)⁺. Amino Acid Analysis: 1.04 Ala; 0.97 Pro; 1.26 Lys(Isp); 1.05 Leu; 0.97 Lys; 1.04 NMeTyr; 0.53 Ser; 0.96 3Pal; 0.96 4ClPhe.

Example 72c N-Thienyl-2-carbonyl-D2Nal-D4ClPhe-D3Pal-Ser-NMeTyr-DLys(Nic)-Leu-Lys(Isp)-Pro-DAlaNH$_2$ (Compound 19b) R$_t$=31.01 min; FAB Mass spec. m/e 1602 (M+H)⁺. Amino Acid Analysis: 0.99 Ala; 0.99 Pro; 0.93 Lys(Isp); 1.01 Leu; 0.94 Lys; 0.97 NMeTyr; 0.50 Ser; 1.08 3Pal; 1.15 4ClPhe.

Example 72d N-Nicotinyl-D2Nal-D4ClPhe-D3Pal-Ser-NMeTyr-DLys(Nic)-Leu-Lys(Isp)-Pro-DAlaNH$_2$ (Compound 20b) R$_t$=23.63 min; FAB Mass spec. m/e 1597 (M+H)⁺. Amino Acid Analysis: 0.99 Ala; 1.01 Pro; 0.95 Lys(Isp); 1.02 Leu; 0.97 Lys; 1.06 NMeTyr; 0.48 Ser; 1.01 3Pal; 1.07 4ClPhe.

Example 72e N-Picolinoyl-D2Nal-D4ClPhe-D3Pal-Ser-NMeTyr-DLys(Nic)-Leu-Lys(Isp)-Pro-DAlaNH$_2$ (Compound 21bb) R$_t$=30.9 min; FAB Mass spec. m/e 1597 (M+H)⁺. Amino Acid Analysis: 1.01 Ala; 1.03 Pro; 0.94 Lys(Isp); 1.01Leu; 0.95 Lys; 1.07 NMeTyr; 0.50 Ser; 0.99 3Pal; 1.06 4ClPhe.

Example 72f N-(6-Hydroxy)nicotinyl-D2Nal-D4ClPhe-D3Pal-Ser-NMeTyr-DLys(Nic)-Leu-Lys(Isp)-Pro-DAlaNH$_2$ (Compound 22b) R$_t$=23.80 min; FAB Mass spec. m/e 1613 (M+H)⁺. Amino Acid Analysis: 1.01 Ala; 1.02 Pro; 0.95 Lys(Isp); 1.01 Leu; 0.96Lys; 0.98 NMeTyr; 0.51 Ser; 0.98 3Pal; 1.06 4ClPhe.

Example 72g N-Isonicotinyl-D2Nal-D4ClPhe-D3Pal-Ser-NMeTyr-DLys(Nic)-Leu-Lys(Isp)-Pro-DAlaNH$_2$ (Compound 23b) R$_t$=22.71min; FAB Mass spec. m/e 1597 (M+H)⁺. Amino Acid Analysis: 1.00 Ala; 1.01 Pro; 0.93 Lys(Isp); 1.02 Leu; 0.97 Lys; 1.10 NMeTyr; 0.42 Ser; 1.02 3Pal; 1.07 4ClPhe.

Example 72h N-(3-Pyridylacetyl)-D2Nal-D4ClPhe-D3Pal-Ser-NMeTyr-DLys(Nic)-Leu-Lys(Isp)-Pro-DAlaNH$_2$ (Compound 24b) R$_t$=22.71min; FAB Mass spec. m/e 1611 (M+H)⁺. Amino Acid Analysis: 0.99 Ala; 0.99 Pro; 0.92 Lys(Isp); 1.01Leu; 0.94Lys; 1.07 NMeTyr; 0.50 Ser; 1.08 3Pal; 1.13 4ClPhe.

EXAMPLE 73

N-Shikimyl-D2Nal-D4ClPhe-D3Pal-Ser-Lys(Nic)-DLys(Nic)-Leu-Lys(Isp)-Pro-DAlaNH$_2$ (Compound 31b)

The procedure described in Example 71 was used but substituting BOC-Lys(Nic) for BOC-NMeTyr(O-2,6-Cl-BzL). After work-up, lyophilization, and HPLC purification N-Shikimyl-D2Nal-D4ClPhe-D3Pal-Ser-Lys(Nic)-DLys(Nic)-Leu-Lys(Isp)-Pro-DAlaNH$_2$ was obtained; R$_t$=18.86 min; FAB Mass spec. m/e 1704 (M+H)⁺. Amino Acid Analysis: 1.00 Ala; 1.03 Pro; 0.94 Lys(Isp); 1.03 Leu; 1.97 Lys; 0.59 Ser; 0.97 3Pal; 1.00 4ClPhe.

EXAMPLE 74

N-Nicotinyl-D2Nal-D4ClPhe-D3Pal-Ser-Lys(Nic)-DLys(Nic)-Leu-Lys(Isp)-Pro-DAlaNH$_2$ (Compound 32b)

The procedure described in Example 71 was used but substituting BOC-Lys(Nic) for BOC-NMeTyr(O-2,6-Cl-BzL). After work-up, lyophilization, and HPLC purification N-Nicotinyl-D2Nal-D4ClPhe-D3Pal-Ser-Lys(Nic)-DLys(Nic)-Leu-Lys(Isp)-Pro-DAlaNH$_2$ was obtained; R$_t$=20.05 min; FAB Mass spec. m/e 1652 (M+H)⁺. Amino Acid Analysis: 1.01 Ala; 1.01 Pro; 1.08 Lys(Isp); 1.05Leu; 1.92 Lys; 0.56 Ser; 0.95 3Pal; 0.97 4ClPhe.

EXAMPLE 75

N-Shikimyl-D2Nal-D4ClPhe-D3Pal-Ser-Tyr-DLys(Nic)-Leu-Lys(Isp)-Pro-DAlaNH$_2$ (Compound 33b)

The procedure described in Example 73 was used but substituting BOC-Tyr(O-2,6-Cl-Bzl) for BOC-Lys(Nic). After work-up, lyophilization, and HPLC purification N-Shikimyl-D2Nal-D4ClPhe-D3Pal-Ser-Tyr-DLys(Nic)-Leu-Lys(Isp)-Pro-DAlaNH$_2$ was obtained; R$_t$=22.38 min; FAB Mass spec. m/e 1634 (M+H)⁺. Amino Acid Analysis:

1.01 Ala; 0.99 Pro; 1.04 Lys(Isp); 1.00 Leu; 1.00 Lys; 0.92 Tyr; 0.55 Ser; 0.97 3Pal; 0.97 4ClPhe.

EXAMPLE 76

N-(S)-Tetrahydofur-2-oyl-D2Nal-D4ClPhe-D3Pal-Ser-NMeTyr-DCit-Leu-Arg-Pro-DAlaNH$_2$ (Compound 41b)

The procedure described in Example 67 was used but substituting BOC-DCit for BOC-DLys(Nic) and BOC-Arg-(Tos) for BOC-Lys(Isp,Cbz). After work-up, lyophilization, and HPLC purification N-(S)-Tetrahydofur-2-oyl-D2Nal-D4ClPhe-D 3Pal-Ser-NMeTyr-DCit-Leu-Arg-Pro-DAlaNH$_2$ was obtained; R$_t$=37.15 min; FAB Mass spec. m/e 1501 (M+H)$^+$. Amino Acid Analysis: 1.05 Ala; 0.97 Pro; 0.98 Arg; 0.99 Leu; 1.05 Cit; 0.61 NMeTyr; 0.59 Ser; 1.00 3Pal; 0.98 4ClPhe.

EXAMPLE 77

N-(R)-Tetrahydofur-2-oyl-D2Nal-D4ClPhe-D3Pal-Ser-NMeTyr-DCit-Leu-Arg-Pro-DAlaNH$_2$ (Compound 42b)

The procedure described in Example 76 was used but substituting (R)-tetrahydro-2-furoic acid for (S)-tetrahydro-2-furoic acid. After work-up, lyophilization, and HPLC purification N-(R)-Tetrahydofur-2-oyl-D2Nal-D4ClPhe-D 3Pal-Ser-NMeTyr-DCit-Leu-Arg-Pro-DAlaNH$_2$ was obtained; R$_t$=38.20 min; FAB Mass spec. m/e 1501 (M+H)$^+$. Amino Acid Analysis: 1.01 Ala; 0.99 Pro; 0.99 Arg; 1.01 Leu; 1.04 Cit; 0.68 NMeTyr; 0.50 Ser; 1.05 3Pal; 1.03 4ClPhe.

EXAMPLE 78

The procedure described in Example 77 was used but substituting the appropriate acids for (R)-tetrahydro-2-furoic acid. After work-up, lyophilization, and HPLC purification the following compounds were obtained:

Example 78a  N-(R)-5-Oxo-tetrahydrofur-2-oyl-D2Nal-D4ClPhe-D3Pal-Ser-NMeTyr-DCit-Leu-Arg-Pro-DAlaNH$_2$ (Compound 43b) was obtained; R$_t$=37.40 min; FAB Mass spec. m/e 1514 (M+H)$^+$. Amino Acid Analysis: 1.02 Ala; 1.02 Pro; 0.97 Arg; 0.98 Leu; 0.94 Cit; 0.68 NMeTyr; 0.51 Ser; 1.00 3Pal; 1.05 4ClPhe.

Example 78b  N-(S)-5-Oxo-tetrahydrofur-2-oyl-D2Nal-D4ClPhe-D3Pal-Ser-NMeTyr-DCit-Leu-Arg-Pro-DAlaNH$_2$ (Compound 44b) was obtained; R$_t$=37.80 min; FAB Mass spec. m/e 1514 (M+H)$^+$. Amino Acid Analysis: 1.03 Ala; 1.02 Pro; 0.98 Arg; 0.99 Leu; 0.91 Cit; 0.57 NMeTyr; 0.48 Ser; 1.01 3Pal; 1.05 4ClPhe.

Example 78c  N-Shikimyl-D2Nal-D4ClPhe-D3Pal-Ser-NMeTyr-DCit-Leu-Arg-Pro-DAlaNH$_2$ (Compound 45b) was obtained; R$_t$=32.45 min; FAB Mass spec. m/e 1558 (M+H)$^+$. Amino Acid Analysis: 1.02 Ala; 1.03 Pro; 0.91 Arg; 1.04 Leu; 1.04 Cit; 0.94 NMeTyr; 0.52 Ser; 0.72 3Pal; 1.01 4ClPhe.

Example 78d  N-2-Furoyl-D2Nal-D4ClPhe-D3Pal-Ser-NMeTyr-DCit-Leu-Arg-Pro-DAlaNH$_2$ (Compound 46b) was obtained; R$_t$=38.30 min; FAB Mass spec. m/e 1498 (M+H)$^+$. Amino Acid Analysis: 1.01 Ala; 1.07 Pro; 0.97 Arg; 1.00 Leu; 0.93 Cit; 0.60 NMeTyr; 0.60 Ser; 0.93 3Pal; 0.94 4ClPhe.

Example 78e  N-Isonicotinyl-D2Nal-D4ClPhe-D3Pal-Ser-NMeTyr-DCit-Leu-Arg-Pro-DAlaNH$_2$ (Compound 47b) was obtained; R$_t$=32.80 min; FAB Mass spec. m/e 1507 (M+H)$^+$. Amino Acid Analysis: 1.02 Ala; 1.02 Pro; 0.96 Arg; 1.00 Leu; 0.99 Cit; 0.82 NMeTyr; 0.40 Ser; 1.04 3Pal; 1.09 4ClPhe.

Example 78f  N-Picolinoyl-D2Nal-D4ClPhe-D3Pal-Ser-NMeTyr-DCit-Leu-Arg-Pro-DAlaNH$_2$ (Compound 48b) was obtained; R$_t$39.55 min; FAB Mass spec. m/e 1507 (M+H)$^+$. Amino Acid Analysis: 1.01 Ala; 1.03 Pro; 0.93 Arg; 1.04 Leu; 1.03 Cit; 1.07 NMeTyr; 0.50 Ser; 0.68 3Pal; 0.95 4ClPhe.

Example 78g  N-Nicotinyl-D2Nal-D4ClPhe-D3Pal-Ser-NMeTyr-DCit-Leu-Arg-Pro-DAlaNH$_2$ (Compound 49b) was obtained; R$_t$=32.10 min; FAB Mass spec. m/e 1507 (M+H)$^+$. Amino Acid Analysis: 0.99 Ala; 1.00 Pro; 0.99 Arg; 1.01 Leu; 0.99 Cit; 1.00 NMeTyr; 0.45 Ser; 1.01 3Pal; 1.00 4ClPhe.

Example 78h  N-(3-Pyridylacetyl)-D2Nal-D4ClPhe-D3Pal-Ser-NMeTyr-DCit-Leu-Arg-Pro-DAlaNH$_2$ (Compound 50b) was obtained; R$_t$=32.0 min; FAB Mass spec. m/e 1521 (M+H)$^+$. Amino Acid Analysis: 0.99 Ala; 1.02 Pro; 0.96 Arg; 1.02 Leu; 0.98 Cit; 0.93 NMeTyr; 0.45 Ser; 1.14 3Pal; 1.19 4ClPhe.

EXAMPLE 79

N-Shikimyl-D2Nal-D4ClPhe-D3Pal-Ser-NMeTyr-DLys(Shik)-Leu-Harg-Pro-DAlaNH$_2$ (Compound 52b)

The procedure described in Example 78 was used but substituting shikimic acid for 5-oxo-tetrahydrofur-2-oyl acid, BOC-Harg(NO$_2$) for BOC-Arg(Tos), and BOC-DLys-(FMOC) for BOC-DCit. With the completion of the synthesis the resin was treated with 30% piperidine in DMF, washed and coupled with shikimic acid using two-two hours coupling protocol. After work-up, lyophilization, and HPLC purification N-Shikimyl-D2Nal-D4ClPhe-D3Pal-Ser-NMeTyr-DLys(Shik)-Leu-Harg-Pro-DAlaNH$_2$ was obtained: R$_t$=15.54 min; FAB Mass spec. m/e 1699 (M+H)$^+$. Amino Acid Analysis: 1.01 Ala; 0.99 Pro; 0.99 Leu; 1.00 Lys; 1.02 NMeTyr; 0.57 Ser; 0.98 3Pal; 1.04 4ClPhe.

EXAMPLE 80

N-(S)-2-Tetrahydrofuroyl-Gly-D2Nal-D4ClPhe-D3Pal-Ser-NMeTyr-DLys(N-epsilon-Nicotinyl)-Leu-Lys(N-epsilon-Isopropyl)-Pro-AlaH$_2$ (Compound 214)

The procedure described in Example 4 was used but substituting BOC-AlaNH-resin for BOC-DAlaNH-resin. After work-up, lyophilization, and HPLC purification N(S)-2-Tetrahydrofuroyl-Gly-D2Nal-D4ClPhe-D3Pal-Ser-NMeTyr-DLys(N-epsilon-Nicotinyl)-Leu-Lys(N-epsilon-Isopropyl)-Pro-AlaNH$_2$ was obtained as the trifluoroacetate salt; R$_t$=18.88 min; FAB Mass spec. m/e 1647 (M+H)$^+$. Amino Acid Analysis: 1.00 Ala; 0.98 Pro; 1.18 Lys(Isp); 1.01 Leu; 1.00 Lys; 0.99 NMeTyr; 0.44 Ser; 1.14 D3Pal; 1.24 D4ClPhe; 0.98 Gly.

EXAMPLE 81

N (S)-2-Tetrahydrofuroyl-Gly-2Nal-D4ClPhe-D3Pal-Ser-NMeTyr-DLys(N-epsilon-Nicotinyl)-Leu-Lys(N-epsilon-Isopropyl)-Pro-DAlaNH$_2$ (Compound 215)

The procedure described in Example 4 was used but substituting BOC-2Nal for BOC-D2Nal. After work-up, lyophilization, and HPLC purification N-(S)-2-Tetrahydrofuroyl-Gly- 2Nal-D4ClPhe-D3Pal-Ser-NMeTyr-DLys(N-epsilon-Nicotinyl) -Leu-Lys(N-epsilon-Isopropyl)-Pro-DAlaNH$_2$ was obtained as the trifluoroacetate salt; R$_t$=20.38 min; FAB Mass spec. m/e 1647 (M+H)$^+$. Amino Acid Analysis: 1.01 Ala; 1.00 Pro; 1.25 Lys(Isp); 1.02 Leu; 1.00 Lys; 1.01 NMeTyr; 0.39 Ser; 1.13 D3Pal; 1.22 D4ClPhe; 0.97 Gly.

EXAMPLE 82

N
(S)-2-Tetrahydrofuroyl-Gly-D2Nal-D4ClPhe-D3Pal-
DSer-NMeTyr-DLys(N-epsilon-Nicotinyl)
-Leu-Lys(N-epsilon-Isopropyl)-Pro-DAlaNH$_2$
(Compound 216)

The procedure described in Example 4 was used but substituting BOC-DSer(OBzl) for BOC-Ser(OBzl). After work-up, lyophilization, and HPLC purification N(S)-2-Tetrahydrofuroyl-Gly-D2Nal-D4ClPhe-D3Pal-DSer-NMeTyr-DLys(N-epsilon-Nicotinyl) -Leu-Lys(N-epsilon-Isopropyl)-Pro-DAlaNH$_2$ was obtained as the trifluoroacetate salt; R$_t$=20.035 min; FAB Mass spec. m/e 1647 (M+H)$^+$. Amino Acid Analysis: 1.00 Ala; 0.99Pro; 1.16 Lys(Isp); 1.01 Leu; 1.01 Lys; 0.98 NMeTyr; 0.48 Ser; 1.15 D3Pal; 1.23 D4ClPhe; 0.99 Gly.

EXAMPLE 83

N
(S)-2-Tetrahydrofuroyl-Gly-D2Nal-D4ClPhe-3Pal-
Ser-NMeTyr-DLys(N-epsilon-Nicotinyl)
-Leu-Lys(N-epsilon-Isopropyl)-Pro-DAlaNH$_2$
(Compound 217)

The procedure described in Example 4 was used but substituting BOC-3Pal for BOC-D3Pal. After work-up, lyophilization, and HPLC purification N-(S)-2-Tetrahydrofuroyl-Gly-D2Nal-D 4ClPhe-3Pal-Ser-NMeTyr-DLys(N-epsilon-Nicotinyl)-Leu-Lys(N-epsilon-Isopropyl)-Pro-DAlaNH$_2$ was obtained as the trifluoroacetate salt; R$_t$=20.24 min; FAB Mass spec. m/e 1647 (M+H)$^+$. Amino Acid Analysis: 1.00 Ala; 1.00 Pro; 1.23 Lys(Isp); 1.01 Leu; 1.01 Lys; 1.01 NMeTyr; 0.44 Ser; 1.14D3Pal; 1.24D4ClPhe; 0.98 Gly.

EXAMPLE 84

N
(S)-2-Tetrahydrofuroyl-Gly-D2Nal-D4ClPhe-D3Pal-
Ser-NMeTyr-DLys(N-epsilon-Nicotinyl)
-Leu-Lys(N-epsilon-Isopropyl)-Pro-DAlaOH
(Compound 218)

The procedure described in Example 4 was used but substituting BOC-DAla-O-resin (Merrifield) for BOC-DAla-NH-resin (benzhydralamine). After treatment with HF, work-up, lyophilization, and HPLC purification N-(S)-2-Tetrahydrofuroyl-Gly-D2Nal-D4ClPhe-D 3Pal-Ser-NMeTyr-DLys(N-epsilon-Nicotinyl)-Leu-Lys(N-epsilon-Isopropyl)-Pro-DAlaOH was obtained as the trifluoroacetate salt; R$_t$=19.92 min; FAB Mass spec. m/e 1647 (M+H)$^+$. Amino Acid Analysis: 1.01 Ala; 1.00 Pro; 1.26 Lys(Isp); 1.02 Leu; 1.01 Lys; 1.02 NMeTyr; 0.42 Ser; 1.14 D3Pal; 1.25 D4ClPhe; 0.97 Gly.

EXAMPLE 85

N
(S)-2-Tetrahydrofuroyl-Gly-D2Nal-D4ClPhe-D3Pal-
Ser-NMeTyr-Lys(N-epsilon-Nicotinyl)
-Leu-Lys(N-epsilon-Isopropyl)-Pro-DAlaNH$_2$
(Compound 219)

The procedure described in Example 4 was used but substituting BOC-Lys(Nic) for BOC-DLys(Nic). After work-up, lyophilization, and HPLC purification N-(S)-2-Tetrahydrofuroyl-Gly-D2Nal-D4ClPhe-D3Pal-Ser-NMeTyr-Lys(N-epsilon-Nicotinyl) -Leu-Lys(N-epsilon-Isopropyl)-Pro-DAlaNH$_2$ was obtained as the trifluoroacetate salt; R$_t$=19.60 min; FAB Mass spec. m/e 1647 (M+H)$^+$. Amino Acid Analysis: 1.00 Ala; 1.07 Pro; 1.25 Lys(Isp); 1.01 Leu; 1.01 Lys; 1.07 NMeTyr; 0.40 Ser; 1.13 D3Pal; 1.25 D4ClPhe; 0.96 Gly.

EXAMPLE 86

N
(S)-2-Tetrahydrofuroyl-Gly-D2Nal-4ClPhe-D3Pal-
Ser-NMeTyr-DLys(N-epsilon-Nicotinyl)
-Leu-Lys(N-epsilon-Isopropyl)-Pro-DAlaNH$_2$
(Compound 220)

The procedure described in Example 4 was used but substituting BOC-4ClPhe for BOC-D4ClPhe After work-up, lyophilization, and HPLC purification N-(S)-2-Tetrahydrofuroyl-Gly-D2Nal-4ClPhe- 3DPal-Ser-NMeTyr-DLys(N-epsilon-Nicotinyl)-Leu-Lys(N-epsilon-Isopropyl)-Pro-DAlaNH$_2$ was obtained as the trifluoroacetate salt; R$_t$=19.85 min; FAB Mass spec. m/e 1647 (M+H)$^+$. Amino Acid Analysis: 1.00 Ala; 1.01 Pro; 1.24 Lys(Isp); 1.01 Leu; 1.07 Lys; 1.06 NMeTyr; 0.42 Ser; 1.14 D3Pal; 1.27 D4ClPhe; 0.97 Gly.

EXAMPLE 87

N
(S)-2-Tetrahydrofuroyl-Gly-D2Nal-D4ClPhe-D3Pal-
Ser-NMeTyr-DLys(N-epsilon-Nicotinyl)
-DLeu-Lys(N-epsilon-Isopropyl)-Pro-DAlaNH$_2$
(Compound 221)

The procedure described in Example 4 was used but substituting BOC-DLeu for BOC-Leu. After work-up, lyophilization, and HPLC purification N-(S)-2-Tetrahydrofuroyl-Gly-D2Nal-D 4ClPhe-D3Pal-Ser-NMeTyr-DLys(N-epsilon-Nicotinyl) -DLeu-Lys(N-epsilon-Isopropyl)-Pro-DAlaNH$_2$ was obtained as the trifluoroacetate salt; R$_t$=19.96 min; FAB Mass spec. m/e 1647 (M+H)$^+$. Amino Acid Analysis: 1.00 Ala; 1.01 Pro; 1.24 Lys(Isp); 1.01 Leu; 1.01 Lys; 1.04 NMeTyr; 0.37 Ser; 1.13 D3Pal; 1.26 D4ClPhe; 0.97 Gly.

EXAMPLE 88

N
(S)-2-Tetrahydrofuroyl-Gly-D2Nal-D4ClPhe-D3Pal-
Ser-NMeTyr-DLys(N-epsilon-Nicotinyl)
-Leu-Lys(N-epsilon-Isopropyl)-DPro-DAlaNH$_2$
(Compound 222)

The procedure described in Example 4 was used but substituting BOC-DPro for BOC-Pro. After work-up, lyophilization, and HPLC purification N-(S)-2-Tetrahydrofuroyl-Gly-D2Nal-D 4ClPhe-D3Pal-Ser-NMeTyr-DLys(N- epsilon-Nicotinyl)-Leu-Lys(N-epsilon-Isopropyl)-DPro-DAlaNH$_2$ was obtained as the trifluoroacetate salt; R$_t$=19.71 min; FAB Mass spec. m/e 1647 (M+H)$^+$. Amino Acid Analysis: 0.99 Ala; 1.01 Pro; 1.23 Lys(Isp); 1.01 Leu; 1.01 DLys; 1.06 NMeTyr; 0.41 Ser; 1.14 D3Pal; 1.26 D4ClPhe; 0.98 Gly.

EXAMPLE 89

N
(S)-2-Tetrahydrofuroyl-Gly-D2Nal-D4ClPhe-D3Pal-Ser-NMeTyr-DLys(N-epsilon-Nicotinyl)
-Leu-DLys(N-epsilon-Isopropyl)-Pro-DAlaNH$_2$
(Compound 223)

The procedure described in Example 4 was used but substituting BOC-DLys(Isp,Cbz) for BOC-Lys(Isp,Cbz). After work-up, lyophilization, and HPLC purification N-(S)-2-Tetrahydrofuroyl-Gly-D2Nal-D4ClPhe-D3Pal-Ser-NMeTyr-DLys(N-epsilon-Nicotinyl) -Leu-DLys(N-epsilon-Isopropyl)-Pro-DAlaNH$_2$ was obtained as the trifluoroacetate salt; R$_t$=15.15 min; FAB Mass spec. m/e 1647 (M+H)$^+$. Amino Acid Analysis: 1.00 Ala; 0.99 Pro; 0.95 Lys(Isp); 1.01 Leu; 1.02 Lys; 1.00 NMeTyr; 0.42 Ser; 0.93 D3Pal; 1.10 D4ClPhe; 0.98 Gly.

EXAMPLE 90

N
(S)-2-Tetrahydrofuroyl-Gly-D2Nal-D4ClPhe-D3pal-Ser-DNMeTyr-DLys(N-epsilon-Nicotinyl)
-Leu-Lys(N-epsilon-Isopropyl)-pro-DAlaNH$_2$
(Compound 224)

The procedure described in Example 4 was used but substituting BOC-DNMeTyr(O-2,6ClBzl) for BOC-NMeTyr(O-2,6ClBzl). After work-up, lyophilization, and HPLC purification N-(S)-2-Tetrahydrofuroyl-Gly-D2Nal-D 4ClPhe-D3Pal-Ser-DNMeTyr-DLys(N-epsilon-Nicotinyl)-Leu-Lys(N-epsilon-Isopropyl)-Pro-DAlaNH$_2$ was obtained as the trifluoroacetate salt; R$_t$=19.60 min; FAB Mass spec. m/e 1647 (M+H)$^+$. Amino Acid Analysis: 1.03 Ala; 1.00 Pro; 0.64 Lys(Isp); 1.00 Leu; 1.00 Lys; 0.79 NMeTyr; 0.29 Ser; 0.98 D3Pal; 1.03 D4ClPhe; 0.96 Gly.

EXAMPLE 91

N
(R,S)-2-Tetrahydrofuroyl-Gly-D2Nal-D4ClPhe-D3Pal-Ser-Tyr-DLys(N-epsilon-Nicotinyl)
-Leu-Lys(N-epsilon-Isopropyl)-Pro-DAlaNH$_2$
(Compound 225)

The procedure described in Example 3 was used but substituting BOC-Tyr(O-2,6ClBzl) for BOC-NMeTyr(O-2,6ClBzl). After work-up, lyophilization, and HPLC purification N-(R,S)-2-Tetrahydrofuroyl-Gly-D2Nal-D4ClPhe-D3Pal-Ser-Tyr-DLys(N-epsilon-Nicotinyl) -Leu-Lys(N-epsilon-Isopropyl)-Pro-DAlaNH$_2$ was obtained as the trifluoroacetate salt; R$_t$=19.14 min; FAB Mass spec. m/e 1633 (M+H)$^+$. Amino Acid Analysis: 0.99 Ala; 1.00 Pro; 1.00 Lys(Isp); 1.00 Leu; 1.00 Lys; 1.02 Tyr; 0.46 Ser; 0.98 D3Pal; 1.02 D4ClPhe; 0.96 Gly.

EXAMPLE 92

N
(S)-2-Tetrahydrofuroyl-Gly-D2Nal-D4ClPhe-D3Pal-Ser-NMeTyr-DHcit-Leu-Lys(N-epsilon-Isopropyl)
-Pro-DAlaNH$_2$ (Compound 226)

The procedure described in Example 4 was used but substituting BOC-DHcit for BOC-DLys(Nic). After work-up, lyophilization, and HPLC purification N-(S)-2-Tetrahydrofuroyl-Gly-D2Nal-D 4ClPhe-D3Pal-Ser-NMeTyr-DHcit-Leu-Lys(N-epsilon-Isopropyl)-Pro-DAlaNH$_2$ was obtained as the trifluoroacetate salt; R$_t$=20.58 min; FAB Mass spec. m/e 1585 (M+H)$^+$. Amino Acid Analysis: 1.01 Ala; 1.01 Pro; 0.99 Lys(Isp); 1.01 Leu; 0.87 NMeTyr; 0.48 Ser; 0.99 D3Pal; 1.04 D4ClPhe; 0.98 Gly.

EXAMPLE 93

N
(S)-2-Tetrahydrofuroyl-Gly-D2Nal-D4ClPhe-D3Pal-Ser-Tyr-DHcit-Leu-Lys(N-epsilon-Isopropyl)-Pro-DAlaNH$_2$ (Compound 227)

The procedure described in Example 92 was used but substituting BOC-Tyr(O-2,6ClBzl) for BOC-NMeTyr(O-2,6ClBzl). After work-up, lyophilization, and HPLC purification N-(S)-2-Tetrahydrofuroyl-Gly-D2Nal-D4ClPhe-D3Pal-Ser-Tyr-DHcit-Leu-Lys(N-epsilon-Isopropyl) -Pro-DAlaNH$_2$ was obtained as the trifluoroacetate salt; R$_t$=19.73 min; FAB Mass spec. m/e 1571 (M+H)$^+$. Amino Acid Analysis: 1.00 Ala; 0.98 Pro; 0.87 Lys(Isp); 1.01 Leu; 0.99 Tyr; 0.52 Ser; 0.91 D3Pal; 1.02 D4ClPhe; 0.98 Gly.

EXAMPLE 94

N
(S)-2-Tetrahydrofuroyl-Gly-D2Nal-DPhe-D3Pal-Ser-NMeTyr-DLys(Nic)-Leu-Lys(N-epsilon-Isopropyl)-Pro-DAlaNH$_2$ (Compound 228)

The procedure described in Example 4 was used but substituting BOC-DPhe for BOC-D4ClPhe. After work-up, lyophilization, and HPLC purification N-(S)-2-Tetrahydrofuroyl-Gly-D2Nal-DPhe-D 3Pal-Ser-NMeTyr-DLys(Nic)-Leu-Lys(N-epsilon-Isopropyl)-Pro-DAlaNH$_2$ was obtained as the trifluoroacetate salt; R$_t$=17.61 min; FAB Mass spec. m/e 1613 (M+H)$^+$. Amino Acid Analysis: 0.98 Ala; 0.98 Pro; 0.87 Lys(Isp); 1.00 Leu; 0.97 NMeTyr; 1.02 Lys(Nic); 0.43 Ser; 0.89 D3Pal; 1.05 Phe; 0.95 Gly.

EXAMPLE 95

N-(S)-2-Tetrahydrofuroyl-Gly-D2Nal-D4ClPhe-D3Pal-Ser-Tyr-DHcit-Leu-Arg-Pro-DAlaNH$_2$
(Compound 230)

The procedure described in Example 4 was used but substituting BOC-Tyr(O-2,6ClBzl), BOC-DHcit and BOC-Arg(NO$_2$) for BOC-NMeTyr(O-2,6ClBzl), DLys(Nic) and BOC-Lys(Isp,Cbz), respectively. After work-up, lyophilization, and HPLC purification N-(S)-2-Tetrahydrofuroyl-Gly-D2Nal-D4ClPhe-D3Pal-Ser-Tyr-DHcit-Leu-Arg-Pro-DAlaNH$_2$ was obtained as the trifluoroacetate salt; R$_t$=19.61 min; FAB Mass spec. m/e 1557 (M+H)$^+$. Amino Acid Analysis: 1.01 Ala; 1.04 Pro; 0.96 Arg; 1.04 Leu; 0.93 Tyr; 0.5 Ser; 1.01 D3Pal; 1.08 D4ClPhe; 1.01 Gly; 1.01 Hcit.

EXAMPLE 96

N
(S)-2-Tetrahydrofuroyl-Bala-D2Nal-D4ClPhe-D3Pal-
Ser-NMeTyr-DLys(Nic)-Leu-Lys(Isp)-Pro-DAlaNH$_2$
(Compound 231)

The procedure described in Example 4 was used but substituting BOC-Bala for BOC-Gly. After work-up, lyophilization, and HPLC purification N-(S)-2-Tetrahydrofuroyl-Bala-D2Nal-D4ClPhe-D 3Pal-Ser-NMeTyr-DLys-(Nic)-Leu-Lys(Isp)-Pro-DAlaNH$_2$ was obtained as the trifluoroacetate salt; R$_t$=19.37 min; FAB Mass spec. m/e 1661 (M+H)$^+$. Amino Acid Analysis: 0.98 Ala; 1.00 Pro; 0.89 Lys(Isp); 1.01 Leu; 1.01 Lys; 1.05 NMeTyr; 0.40 Ser; 0.99 D3Pal; 1.09 D4ClPhe.

EXAMPLE 97

N
(S)-2-Tetrahydrofuroyl-Gaba-D2Nal-D4ClPhe-D3Pal-
Ser-NMeTyr-DLys(Nic)-Leu-Lys(Isp)-Pro-DAlaNH$_2$
(Compound 232)

The procedure described in Example 96 was used but substituting BOC-Gaba for BOC-Bala. After work-up, lyophilization, and HPLC purification N-(S)-2-Tetrahydrofuroyl-Gaba-D2Nal-D4ClPhe-D 3Pal-Ser-NMeTyr-DLys-(Nic)-Leu-Lys(Isp)-Pro-DAlaNH$_2$ was obtained as the trifluoroacetate salt; R$_t$=20.02 min; FAB Mass spec. m/e 1675 (M+H)$^+$. Amino Acid Analysis: 0.97 Ala; 1.00 Pro; 0.90 Lys(Isp); 1.01 Leu; 1.05 NMeTyr; 0.37 Ser; 0.98 D3Pal; 1.08 D4ClPhe.

EXAMPLE 98

N
(S)-2-Tetrahydrofuroyl-Aha-D2Nal-D4ClPhe-D3Pal-
Ser-NMeTyr-DLys(Nic)-Leu-Lys(Isp)-Pro-DAlaNH$_2$
(Compound 233)

The procedure described in Example 96 was used but substituting BOC-Aha for BOC-Bala. After work-up, lyophilization, and HPLC purification N-(S)-2-Tetrahydrofuroyl-Aha-D2Nal-D4ClPhe-D 3Pal-Ser-NMeTyr-DLys(Nic)-Leu-Lys(Isp)-Pro-DAlaNH$_2$ was obtained as the trifluoroacetate salt; R$_t$=22.11 min; FAB Mass spec. m/e 1717 (M+H)$^+$. Amino Acid Analysis: 0.98 Ala; 1.00 Pro; 0.91 Lys(Isp); 1.01 Leu; 1.01 Lys;1.06 NMeTyr; 0.38 Ser; 0.98. D3Pal; 1.08 D4ClPhe.

EXAMPLE 99

N
(S)-2-Tetrahydrofuroyl-Sar-D2Nal-D4ClPhe-D3Pal-
Ser-NMeTyr-DLys(Nic),Leu-Lys(Isp)-Pro-DAlaNH$_2$
(Compound 234)

The procedure described in Example 96 was used but substituting BOC-Sar for BOC-Bala. After work-up, lyophilization, and HPLC purification N-(S)-2-Tetrahydrofuroyl-Sar-D2Nal-D 4ClPhe-D3Pal-Ser-NMeTyr-DLys(Nic)-Leu-Lys(Isp)-Pro-DAlaNH$_2$ was obtained as the trifluoroacetate salt; R$_t$=20.266 min; FAB Mass spec. m/e 1661 (M+H)$^+$. Amino Acid Analysis: 0.98 Ala; 1.00 Pro; 0.87 Lys(Isp); 1.00 Leu; 1.01 Lys; 1.02 NMeTyr; .0.42 Ser; 1.00 D3Pal; 1.08 D4ClPhe; 0.89 Sar.

EXAMPLE 100

N
(S)-2-Tetrahydrofuroyl-Gly-DAla-D4ClPhe-D3Pal-
Ser-NMeTyr-DLys(Nic)-Leu-Lys(Isp)-Pro-DAlaNH$_2$
(Compound 235)

The procedure described in Example 4 was used but substituting BOC-DAla for BOC-D2Nal. After work-up, lyophilization, and HPLC purification N-(S)-2-Tetrahydrofuroyl-Gly-DAla-D4ClPhe-D 3Pal-Ser-NMeTyr-DLys-(Nic)-Leu-Lys(Isp)-Pro-DAlaNH$_2$ was obtained as the trifluoroacetate salt; R$_t$=10.94 min; FAB Mass spec. m/e 1521 (M+H)$^+$. Amino Acid Analysis: 1.96 Ala; 1.01 Pro; 0.91Lys(Isp); 1.02 Leu; 1.02 Lys; 1.10 NMeTyr; 0.38 Ser; 0.99 D3Pal; 1.09 D4ClPhe; 1.00 Gly.

EXAMPLE 101

N
(S)-2-Tetrahydrofuroyl-Gly-Sar-D4ClPhe-D3Pal-Ser-
NMeTyr-DLys(Nic)-Leu-Lys(Isp)-Pro-DAlaNH$_2$
(Compound 236)

The procedure described in Example 4 was used but substituting BOC-Sar for BOC-D2Nal. After work-up, lyophilization, and HPLC purification N-(S)-2-Tetrahydrofuroyl-Gly-Sar-D4ClPhe-D 3Pal-Ser-NMeTyr-DLys(Nic)-Leu-Lys(Isp)-Pro-DAlaNH$_2$ was obtained as the trifluoroacetate salt; R$_t$=11.49 min; FAB Mass spec. m/e 1521 (M+H)$^+$. Amino Acid Analysis: 0.98 Ala; 1.01 Pro; 0.91Lys(Isp); 1.02 Leu; 1.01 Lys; 1.09 NMeTyr; 0.36 Ser; 0.99 D3Pal; 1.09 D4ClPhe; 0.93 Sar; 0.99 Gly.

EXAMPLE 102

N
(S)-2-Tetrahydrofuroyl-Aca-D2Nal-D4ClPhe-D3Pal-
Ser-NMeTyr-DLys(Nic)-Leu-Lys(Isp)-Pro-DAlaNH$_2$
(Compound 237)

The procedure described in Example 4 was used but substituting BOC-Aca for BOC-Gly. After work-up, lyophilization, and HPLC purification N-(S)-2-Tetrahydrofuroyl-Aca-D2Nal-D 4ClPhe-D3Pal-Ser-NMeTyr-DLys(Nic)-Leu-Lys(Isp)-Pro-DAlaNH$_2$ was obtained as the trifluoroacetate salt; R$_t$=20.45 min; FAB Mass spec. m/e 1703 (M+H)$^+$. Amino Acid Analysis: 0.97 Ala; 1.00 Pro; 0.89 Lys(Isp); 1.01 Leu; 1.01 Lys; 1.07 NMeTyr; 0.44 Ser; 1.11 D3Pal; 1.08 D4ClPhe; 1.01 Aca.

What is claimed is:

1. A peptide having structure I or pharmaceutically acceptable salt thereof

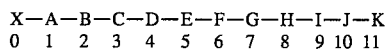

wherein
X is an acyl group selected from the group consisting of
(a) dihydroshikimyl,
(b) 2-furoyl,
(c) 3-furoyl,
(d) tetrahyrofuro-2-yl,
(e) tetrahydrofuro-3-yl,
(f) (thien-2-yl)carbonyl,
(g) (thien-3-yl)carbonyl,
(h) (tetrahydrothien-2-yl)carbonyl,
(i) (tetrahydrothien-3-yl)carbonyl, (j) pyrrol-2-yl)carbonyl,
(k) (pyrrol-3-yl)carbonyl,
(l) prolyl,
(m) N-acetyl-prolyl,
(n) 3-(indolin-3-yl)propionyl,
(o) (indolin-3-yl)acetyl,
(p) (indolin-2-yl)carbonyl,
(q) (indolin-3-yl)carbonyl,
(r) benzo[b]fur-2-yl)carbonyl,
(s) (dihydrobenzo[b]fur-2-yl)carbonyl,
(t) (tetrahydropyran-2-yl)carbonyl,
(u) (tetrahydropyran-3-yl)carbonyl,
(v) (piperidin-3-yl)carbonyl,
(w) (N-acetylpiperidin-3-yl)carbonyl,
(x) nicotinyl, optionally substituted with alkyl of from one to six carbon atoms, alkoxy of from one to six carbon atoms, halogen, or hydroxy,
(y) isonicotinyl, optionally substituted with alkyl of from one to six carbon atoms, alkoxy of from one to six carbon atoms, halogen, or hydroxy,
(z) picolinoyl,
(aa) 2-, 3- or 4-quinolinecarbonyl, optionally substituted with alkyl of from one to six carbon atoms, alkoxy of from one to six carbon atoms, halogen, or hydroxy;
(bb) salicyl,
(cc) shikimyl, and
(dd) p-toluenesulfonyl;

A is absent or is an aminoacyl residue selected from the group consisting of
D-alanyl,
3-aminopropionyl,
4-aminobutyryl,
5-aminovaleryl,
6-amino-hexanoyl,
7-aminoheptanoyl,
8-aminooctanoyl,
11-aminoundecanoyl,
azaglycyl,
glycyl,
sarcosyl, and
D-seryl;

B is an aminoacyl residue selected from the group consisting of
D-phenylalanyl,
D-3-(4-chlorophenyl)alanyl,
D-3-(4-fluorophenyl)alanyl,
D-3-(quinolin-3-yl)alanyl,
sarcosyl,
glycyl,
azaglycyl,
D-3,3-diphenylalanyl,
$N^\alpha$-methyl-D-3-(naphth-2-yl)alanyl, and
D-3-(naphth-2-yl)alanyl;

C is an aminoacyl residue selected from the group consisting of
D-3-(4-chlorophenyl)alanyl,
D-3,3-diphenylalanyl,
D-3-(4-fluorophenyl)alanyl,
D-3-(naphth-2-yl)alanyl,
D-phenylalanyl, and
D-3-(quinolin-3-yl)alanyl;

D is an aminoacyl residue selected from the group consisting of
D-alanyl,
D-3-(benzo[b]thien-2-yl)alanyl,
glycyl,
D-3-(naphth-1-yl)alanyl,
D-3-(pyrid-3-yl)alanyl,
D-3-(quinolin-3-yl)alanyl, and
D-3-(thiazol-2-yl)alanyl;

E is an aminoacyl residue selected from the group consisting of
glycyl,
L-seryl,
L-homoseryl,
L-seryl(O-benzyl), and
$N^\alpha$(R1)-L seryl where R1 is alkyl of from one to four carbon atoms;

F is an aminoacyl residue selected from the group consisting of
$N^\alpha$(R1)-alanyl,
$N^\alpha$(R1)-(3-(4-(3-amino-1,2,4-triazol-5-yl)amino)phenyl)alanyl,
$N^\alpha$(R1)-(3-(4-((3-amino-1,2,4-triazol-5-amino) methyl)phenyl)alanyl,
$N^\alpha$(R1)-(3-(4-(3-amino-1,2,4-triazol-5-yl)amino)cyclohexyl)alanyl,
$N^\alpha$(R1)-(3-(4-(nicotinyl)amino)cyclohexyll)alanyl,
$N^\alpha$(R1)-(N-e-nicotinyl)lysyl,
$N^\alpha$(R1)-(N-e-(3-amino-1,2,4-triazol-5-yl)lysyl,
$N^\alpha$(R1)-3-(4-nitrophenyl)alanyl,
$N^\alpha$(R1)-3-(4-aminophenyl)alanyl,
$N^\alpha$(R1)-3-(4-aminocyclohexyl)alanyl,
$N^\alpha$(R1)-tyrosyl,
$N^\alpha$(R1)-tyrosyl(O-methyl),
$N^\alpha$(R1)-phenylalanyl,
$N^\alpha$(R1)-cyclohexylalanyl,
$N^\alpha$(R1)-glycyl,
$N^\alpha$(R1)-arginyl,
$N^\alpha$(R1)-histidyl, and
$N^\alpha$(R1)-homoarginyl; where R1 is hydrogen or alkyl of from one to four carbon atoms;

G is an aminoacyl residue selected from the group consisting of
glycyl,
D-citrullyl,
D-homocitrullyl,
β-alanyl,
D-lysyl(N-epsilon glycyl nicotinyl),
D-lysyl(N-epsilon azaglycyl nicotinyl),
D-lysyl(N-epsilon shikimyl),
D-lysyl(N-epsilon glycyl shikimyl),
D-lysyl(N-epsilon azaglycyl shikimyl),
D-lysyl(N-epsilon dihydroshikimyl),
D-lysyl(N-epsilon glycyl dihydroshikimyl),
D-lysyl(N-epsilon azaglycyl dihydroshikimyl),
D-lysyl(N-epsilon fur-2-oyl), D-lysyl(N-epsilon glycyl fur-2-oyl),
D-lysyl(N-epsilon azaglycyl fur-2-oyl),
D-lysyl(N-epsilon tetrahydrofur-2-oyl),
D-lysyl(N-epsilon glycyl tetrahydrofur-2-oyl),
D-lysyl(N-epsilon azaglycyl tetrahydrofur-2-oyl),
D-lysyl(N-epsilon-(3-amino-1,2,4-triazol-5-yl)amino), and
D-3-(4-(3-amino-1,2,4-triazol-5-yl)amino)phenylalanyl;

H is an aminoacyl residue selected from the group consisting of
L-leucyl;
$N^\alpha(R^1)$-L-leucyl;
glycyl;
sarcosyl;
prolyl;
L-valyl;
L-cyclohexylalanyl; and
$N^\alpha(R^1)$-L-cyclohexylalanyl;
where $R^1$ is hydrogen or alkyl of from one to six carbon atoms;

I is an aminoacyl residue selected from the group consisting of
L-citrullyl;
L-homocitrullyl;
L-histidyl;
L-(N-ε-isopropyl)lysyl;
L-arginyl;
$N^\alpha(R^1)$-L-arginyl;
L-homoarginyl;
L-2-amino-6-$N^g$-ethylguanidinohexanoyl; and
L-2-amino-6-$N^g$,$N^g$-diethylguanidinohexanoyl;

J is an aminoacyl residue selected from the group consisting of
L-prolyl;
4-hydroxy-L-prolyl;
L-pipecolyl;
L-azetidinyl;
L-2,8-tetrahydroisoquinoline-2-carbonyl,
$N^\alpha(R^1)$-L-leucyl;
sarcosyl; glycyl; and
N(R1)-L-alanyl;
where $R^1$ is hydrogen or alkyl of from one to six carbon atoms; and K is —NH(CH2CH3) or is an aminoacyl residue selected from the group consisting of
D-alanylamide,
D-alanyl(OH),
D-glutamyl(OH),
L-glutamyl(OH),
$N^\alpha(R^1)$-L-alanylamide,
$N^\alpha(R^1)$)-D-alanylamide,
sarcosamide,
D-serylamide,
azaglycylamide, and
glycylamide,
where $R^1$ is as defined above and with the proviso that when K is —NH(CH$_2$CH$_3$) then J is L-prolyl.

2. A peptide or pharmaceutically acceptable salt thereof as defined by claim 1 wherein X is selected from the group consisting of tetrahydrofur-2-oyl,
tetrahydrofur-3-oyl,
fur-2-oyl,
nicotinyl,
isonicotinyl,
shikimyl,
dihydroshikimyl,
(tetrahydrothien-2-yl)carbonyl,
(pyrrol-2-yl)carbonyl,
prolyl,
(indol-2-yl)carbonyl,
3-(indol-3-yl) propionyl,
(dihydrobenzo[b]fur-2-yl)carbonyl, and
(tetrahydropyran-2-yl)carbonyl.

3. A peptide or pharmaceutically acceptable salt thereof having the structure

X-Gly-D2Nal-D4ClPhe-D3Pal-Ser-AA$^6$-AA$^7$-Leu-AA$^9$Pro-AA$^{11}$ wherein
X is an acyl group selected from the group consisting of
tetrahydrofur-2-oyl,
tetrahydrofur-3-oyl,
fur-2-oyl,
nicotinyl,
isonicotinyl,
shikimyl,
dihydroshikimyl,
(tetrahydrothien-2-yl)carbonyl,
(pyrrol-2-yl)carbonyl,
prolyl,
(indolin-2-yl)carbonyl,
3-(indolin-3-yl) propionyl,
(dihydrobenzo[b]fur-2-yl)carbonyl, and
(tetrahydropyran-2-yl)carbonyl;

AA6 is an aminoacyl residue selected from the group consisting of
tyrosyl,
arginyl,
$N^\alpha$-methyltyrosyl,
lysyl(N-epsilon-(3'-amino-1H-1',2',4'-triazol-5-yl)), and
$N^\alpha$-methyl-3-(4-(3'-amino-1H-1',2',4'-triazol-5-ylmethyl)phenyl)alanyl;

AA7 is an aminoacyl residue selected from the group consisting of
D-citrullyl,
D-lysyl(N-epsilon nicotinyl),
D-lysyl(N-epsilon glycyl nicotinyl),
D-lysyl(N-epsilon azaglycyl nicotinyl),
D-lysyl(N-epsilon shikimyl),
D-lysyl(N-epsilon glycyl shikimyl),
D-lysyl(N-epsilon azaglycyl shikimyl),
D-lysyl(N-epsilon dihydroshikimyl),
D-lysyl(N-epsilon glycyl dihydroshikimyl),
D-lysyl(N-epsilon azaglycyl dihydroshikimyl),
D-lysyl(N-epsilon fur-2-oyl),
D-lysyl(N-epsilon glycyl fur-2-oyl),
D-lysyl(N-epsilon azaglycyl fur-2-oyl),
D-lysyl(N-epsilon tetrahydrofur-2-oyl), D-lysyl(N-epsilon glycyl tetrahydrofur-2-oyl), and D-lysyl(N-epsilon azaglycyl tetrahydrofur-2-oyl);

AA$^9$ is an aminoacyl group selected from the group consisting of lysyl(N-epsilon isopropyl), arginyl, L-(N$^g$,N$^g$-diethyl)homoarginyl, and homoarginyl;

AA$^{11}$ is an aminoacyl residue selected from the group consisting of

D-alanylamide, and D-sarcosamide.

4. A compound as defined by claim 2 or pharmaceutically acceptable salt thereof selected from the group consisting of N-Shikimyl-Gly-D2Nal-D4ClPhe-D3Pal-Ser-NMeTyr-DLys(N-epsilon-Nicotinyl) -Leu-Lys(N-epsilon-Isopropyl)-Pro-DAlaNH$_2$;

N-(R,S)-Tetrahydrofur-2-oyl-Gly-D2Nal-D4ClPhe-D3Pal-Ser-NMeTyr-DLys(Azagly-Nicotinyl) -Leu-Lys(N-epsilon-Isopropyl)-Pro-DAlaNH$_2$;

N-(R,S)-Tetrahydrofur-2-oyl -D2Nal-D4ClPhe-D3Pal-Ser-NMeTyr-DLys(Gly-Nicotinyl) -Leu-Lys(N-epsilon-Isopropyl)-Pro-DAlaNH$_2$;

N-(R,S)-Tetrahydro-Fur-2-oyl-Gly-D2Nal-D4ClPhe-D3Pal-Ser-NMeTyr-DCit-Leu-Arg-Pro-DAlaNH$_2$;

N-Shikimyl-Gly-D2Nal-D4ClPhe-D3Pal-Ser-NMeTyr-DCit-Leu-Arg-Pro-DAlaNH$_2$;

N-Shikimyl-Gly-D2Nal-D4ClPhe-D3Pal-Ser-NMeTyr-DLys(Shik)-Leu-Arg-Pro-DAlaNH$_2$;

N-Nicotinyl-Gly-D2Nal-D4ClPhe-D3Pal-Ser-NMeTyr-DLys(Shik)-Leu-Harg-Pro-DAlaNH$_2$;

N-(R,S)-Tetrahydrofur-2-oyl-Gly-D2Nal-D4ClPhe-D3Pal-Ser-NMeTyr-DLys(Azagly- 2Fur)-Leu-Lys(Isp)-Pro-DAlaNH$_2$;

N-Shik-D2Nal-D4ClPhe-D3Pal-Ser-NMeTyr-DLys(Azagly-Nic)-Leu-Lys(Isp)-Pro-DAlaNH$_2$;

N-Shik-D2Nal-D4ClPhe-D3Pal-Ser-NMeTyr-DLys(Azagly-2Fur)-Leu-Lys(Isp)-Pro-DAlaNH$_2$;

N-(2-Furoyl)-Azagly-D2Nal-D4ClPhe-D3Pal-Ser-NMeTyr-DLys(Nic)-Leu-Lys(Isp)-Pro-DAlaNH$_2$;

N-(R,S) Tetrahydrofur-2-oyl-Gly-D2Nal-D4ClPhe-D3Pal-Ser-NMeTyr-DLys(Nic)-Leu-Lys(Isp)-Pro-SarNH$_2$;

N-(S)-Tetrahydrofur-2-oyl-Gly-D2Nal-D4ClPhe-D3Pal-Ser-NMeTyr-DLys(Nic)-Leu-Lys(Isp)-Pro-SarNH$_2$;

N-(R)-Tetrahydrofur-2-oyl-Gly-D2Nal-D4ClPhe-D3Pal-Ser-NMeTyr-DLys(Nic)-Leu-Lys(Isp)-Pro-SarNH$_2$;

N-(R,S)-Tetrahydrofur-2-oyl-Gly-D2Nal-D4ClPhe-D3Pal-Ser-NMe Phe(Me-Atz)-DPhe(Me-Atz)-Leu-Lys(Isp)-Pro-SarNH$_2$;

N-(R,S)-Tetrahydrofur-2-oyl-Gly-D2Nal-D4ClPhe-D3Pal-Ser-Lys(Atz)-DLys(Atz)-Leu-Lys(Isp)-Pro-SarNH$_2$;

N-(R,S)-Tetrahydrofur-2-oyl-Gly-D2Nal-D4ClPhe-D3Pal-Ser-Tyr-DLys(Nicotinyl) -Leu-Lys(Isp)-Pro-DAlaNH$_2$;

N-(R,S)-Tetrahydrofur-2-oyl-Gly-D2Nal-D4ClPhe-D3Pal-Ser-Lys(Nic)-DLys(Nic)-Leu-Lys(Isp)-Pro-DAlaNH$_2$;

N-(R,S)-Tetrahydrofur-2-oyl-Gly-D2Nal-D4ClPhe-D3Pal-Ser-Tyr-DCit-Leu-Arg-Pro-DAlaNH$_2$;

N-(R,S)-Tetrahydrofur-2-oyl-Gly-D2Nal-D4ClPhe-D3Pal-Ser-Tyr-DHcit-Leu-Arg-Pro-DAlaNH$_2$;

N-(R,S) Tetrahydrofur-2-oyl-Gly-D2Nal-D4ClPhe-D3Pal-Ser-Tyr-DHcit-Leu-Lys(Isp)-Pro-DAlaNH$_2$;

N-(R,S)-Tetrahydrofur-2-oyl-Gly-D2Nal-D4ClPhe-D3Pal-Ser-Tyr-DHarg(Et$_2$)-Leu-Harg(Et$_2$)-Pro-DAlaNH$_2$;

N-(R,S)-Tetrahydrofur-2-oyl-Gly-D2Nal-D4ClPhe-D3Pal-Ser-NMePhe(Atz)-DPhe(Atz)-Leu-Lys(Isp)-Pro-DAlaNH$_2$;

N-(R,S)-Tetrahydrofur-2-oyl-Gly-D2Nal-D4ClPhe-D3Pal-Ser-Phe(Atz)-DPhe(Atz)-Leu-Lys(Isp)-Pro-DAlaNH$_2$;

N-(R,S)-Tetrahydrofur-2-oyl-Gly-D2Nal-D4ClPhe-D3Pal-Ser-NMePhe(Me-Atz)-DPhe(Me-Atz)-Leu-Lys(Isp)-Pro-DAlaNH$_2$; and N-(R,S)-Tetrahydrofur-2-oyl-Gly-D2Nal-D4ClPhe-D3Pal-Ser-Lys(Atz)-DLys(Atz)-Leu-Lys(Isp)-Pro-DAlaNH$_2$.

5. An undecapeptide or pharmaceutically acceptable salt thereof having LHRH antagonist activity having the structure $$X\text{-Gly-D2Nal-D4ClPhe-D3Pal-Ser-N}^\alpha\text{MeTyr-AA}^7\text{-Leu-Lys(Isp)-Pro-AA}^{11}$$

wherein

X is an acyl group selected from the group consisting of tetrahydrofur-2-oyl, fur-2-oyl, nicotinyl, isonicotinyl, shikimyl, and dihydroshikimyl;

AA7 is an aminoacyl residue selected from the group consisting of

D-citrullyl,

D-homocitrullyl,

D-lysyl(N-epsilon nicotinyl),

D-lysyl(N-epsilon glycyl nicotinyl),

D-lysyl(N-epsilon azaglycyl nicotinyl),

D-lysyl(N-epsilon shikimyl),

D-lysyl(N-epsilon glycyl shikimyl),

D-lysyl(N-epsilon azaglycyl shikimyl),

D-lysyl(N-epsilon dihydroshikimyl),

D-lysyl(N-epsilon glycyl dihydroshikimyl),

D-lysyl(N-epsilon azaglycyl dihydroshikimyl),

D-lysyl(N-epsilon fur-2-oyl),

D-lysyl(N-epsilon glycyl fur-2-oyl),

D-lysyl(N-epsilon azaglycyl fur-2-oyl),

D-lysyl(N-epsilon tetrahydrofur-2-oyl),

D-lysyl(N-epsilon glycyl tetrahydrofur-2-oyl), and

D-lysyl(N-epsilon azaglycyl tetrahydrofur-2-oyl); and

AA$^{11}$ is an aminoacyl residue selected from the group consisting of

D-alanylamide, and D-sarcosamide.

6. A compound or pharmaceutically acceptable salt thereof as defined by claim 4 selected from the group consisting of N[(R,S)-Tetrahydrofur-2-oyl]-Gly-D2Nal-D4ClPhe-D3Pal-Ser-N$^{\alpha}$MeTyr-DLys(Nicotinyl)-Leu-Lys(N-epsilon-Isopropyl)-Pro-DAlaNH$_2$;

N[(S)-Tetrahydrofur-2-oyl]-Gly-D2Nal-D4ClPhe-D3Pal-Ser-N$^{\alpha}$MeTyr-DLys(Nicotinyl)-Leu-Lys(N-epsilon-Isopropyl)-Pro-DAlaNH$_2$; and N[(R) Tetrahydrofur-2-oyl]-Gly-D2Nal-D4ClPhe-D3Pal-Ser-N$^{\alpha}$MeTyr-DLys(Nicotinyl)-Leu-Lys(N-epsilon-Isopropyl)-Pro-DAlaNH$_2$.

7. A pharmaceutical composition for suppressing LH levels in a mammal comprising a therapeutically effective amount of a compound as defined by claim 1 in combination with a pharmaceutically acceptable carrier.

8. A method of suppressing LH levels in a mammal comprising administering a therapeutically effective amount of a compound as defined by claim 1.

* * * * *

UNITED STATES PATENT AND TRADEMARK OFFICE
CERTIFICATE OF CORRECTION

PATENT NO. : 5,502,035
DATED : March 26, 1996
INVENTOR(S) : F. Haviv, et al.

It is certified that error appears in the above-indentified patent and that said Letters Patent is hereby corrected as shown below:

Column 58, between lines 56 and 57, please insert --D-lysyl (N-epsilon nicotinyl),--.

Signed and Sealed this

Eighth Day of October, 1996

BRUCE LEHMAN

*Attest:*

*Attesting Officer*          *Commissioner of Patents and Trademarks*